United States Patent [19]
Christopherson et al.

[11] Patent Number: 6,021,352
[45] Date of Patent: Feb. 1, 2000

[54] DIAGNOSTIC TESTING METHODS AND APPARATUS FOR IMPLANTABLE THERAPY DEVICES

[75] Inventors: Mark A. Christopherson; Johann J. Neisz, both of Coon Rapids; Shahram Malek, Plymouth; Todd Goblish, Maple Grove, all of Minn.

[73] Assignee: Medtronic, Inc,, Minneapolis, Minn.

[21] Appl. No.: 08/673,717

[22] Filed: Jun. 26, 1996

[51] Int. Cl.⁷ .................................................. A61N 1/36
[52] U.S. Cl. ............................................. 607/42; 600/529
[58] Field of Search .................................. 607/5, 27, 30, 607/42; 128/716; 600/529

[56] References Cited

U.S. PATENT DOCUMENTS

| | | | |
|---|---|---|---|
| H1347 | 8/1994 | Greeninger et al. | 607/30 |
| 4,236,524 | 12/1980 | Powell et al. | 128/419 |
| 4,250,884 | 2/1981 | Hartlaub et al. | 128/419 |
| 4,305,397 | 12/1981 | Weisbrod et al. | 128/419 |
| 4,323,074 | 4/1982 | Nelms | 128/419 |
| 4,407,296 | 10/1983 | Anderson | 128/675 |
| 4,432,360 | 2/1984 | Mumford et al. | 128/419 |
| 4,445,512 | 5/1984 | Krupka et al. . | |
| 4,485,813 | 12/1984 | Anderson et al. | 128/675 |
| 4,539,993 | 9/1985 | Stanton | 607/43 |
| 4,830,008 | 5/1989 | Meer | 128/421 |
| 4,979,506 | 12/1990 | Silvian | 128/903 |
| 5,097,830 | 3/1992 | Eikefjord et al. . | |
| 5,123,425 | 6/1992 | Shannon, Jr. et al. | 128/848 |
| 5,174,287 | 12/1992 | Kallock et al. | 128/419 |
| 5,178,156 | 1/1993 | Takishima et al. | 128/724 |
| 5,190,053 | 3/1993 | Meer | 128/787 |
| 5,211,173 | 5/1993 | Kallok et al. | 128/419 |
| 5,215,082 | 6/1993 | Kallok et al. | 128/419 |
| 5,233,986 | 8/1993 | Robson | 607/27 |
| 5,335,657 | 8/1994 | Terry et al. . | |
| 5,417,718 | 5/1995 | Kleks et al. | 607/27 |
| 5,483,969 | 1/1996 | Testerman et al. | 128/716 |
| 5,522,862 | 6/1996 | Testerman et al. | 607/42 |
| 5,540,731 | 7/1996 | Testerman . | |
| 5,579,234 | 11/1996 | Wiley et al. . | |
| 5,591,213 | 1/1997 | Morgan . | |
| 5,720,770 | 2/1998 | Nappholz et al. . | |
| 5,724,985 | 3/1998 | Snell et al. . | |

FOREIGN PATENT DOCUMENTS 9427674  12/1994  WIPO ..................................... 607/5

OTHER PUBLICATIONS

M. Broniatowski et al., "Laryngeal Pacemaker. II. Electronic Pacing of Reinnervated Posterior Cricoarytenoid Muscles in the Canine", *Laryngoscope 95*, 1194–1198 (Oct. 1985).

N.J. Douglas et al., "Respiration during sleep in normal man", *Thorax*, 37, 840–844 (1982).

W.L. Glenn, "Diaphragm Pacing: Present Status", *PACE*, 1, 357–370 (Jul.–Sep. 1978).

D.W. Hudgel et al., "Mechanics of the respiratory system and breathing pattern during sleep in normal humans", *J. Appl. Physiol.; Respirat. Environ. Exercise Physiol.*, 56, 133–137 (1984).

(List continued on next page.)

*Primary Examiner*—William E. Kamm
*Assistant Examiner*—Carl H. Layno
*Attorney, Agent, or Firm*—Harold R. Patton; Peter Forrest

[57] ABSTRACT

A testing method for use with a patient stimulation system includes providing a stimulation system including a patient control unit. The patient control unit initiates and terminates treatment periods. At least one period of stimulation to stimulate the patient is automatically provided upon initiating a treatment period. Another method includes a system test method for use with a therapy system. The method includes providing a therapy system having a plurality of components; the therapy system physiologically interacting with a patient. A diagnostic self test of a component of the therapy system is performed internally to the system to determine if the component is functioning properly at a time when the therapy system is not interacting physiologically with the patient. Apparatus for using such methods are also provided.

19 Claims, 31 Drawing Sheets

OTHER PUBLICATIONS

D.W. Hudgel, "Mechanisms of Obstructive Sleep Apnea", *Chest,* 101, 541–549 (Feb. 1992).

C. Iber et al., "A Possible Mechanism for Mixed Apnea in Obstructive Sleep Apnea", *Chest,* 89, 800–805 (Jun. 1986).

J. Krieger et al., "Breathing During Sleep in Normal Middle–Aged Subjects", *Sleep,* 13, 143–154 (1990).

J.E. Remmers et al., "Respiratory Disturbances During Sleep", *Clinics in Chest Medicine,* 1, 57–71 (Jan. 1980).

T. Young et al., "The Occurrence of Sleep–Disordered Breathing Among Middle–Aged Adults", *N. Engl. J. Med.,* 328, 1230–1235 (Apr. 29, 1993).

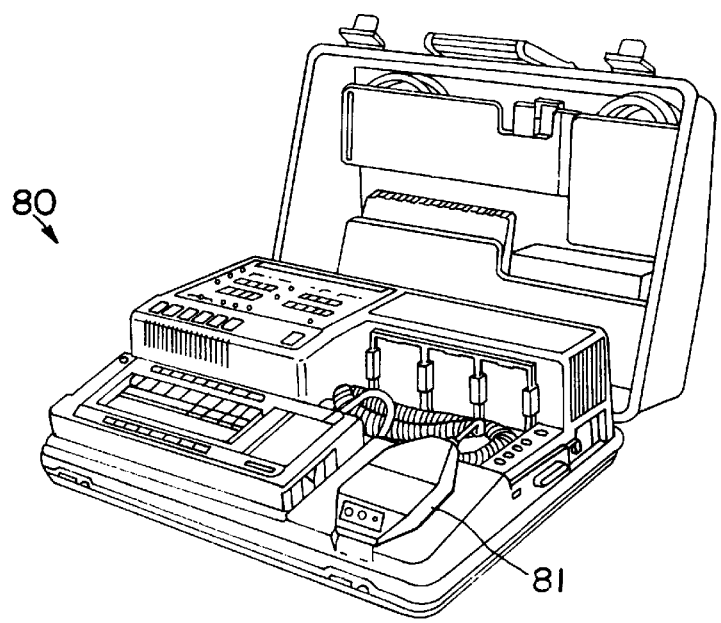
FIG. 7
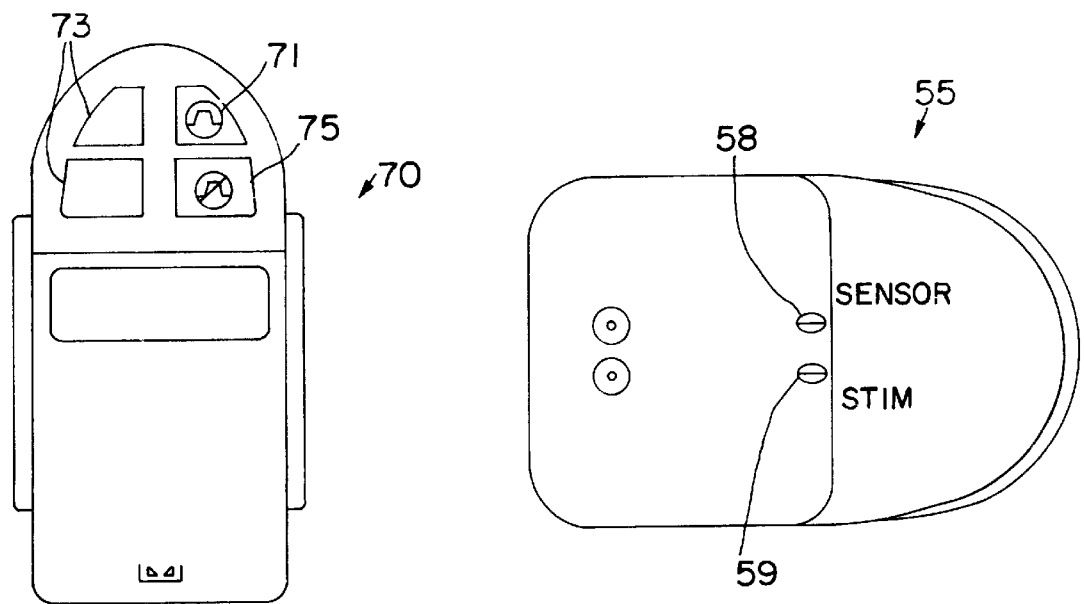
FIG. 8
FIG. 9

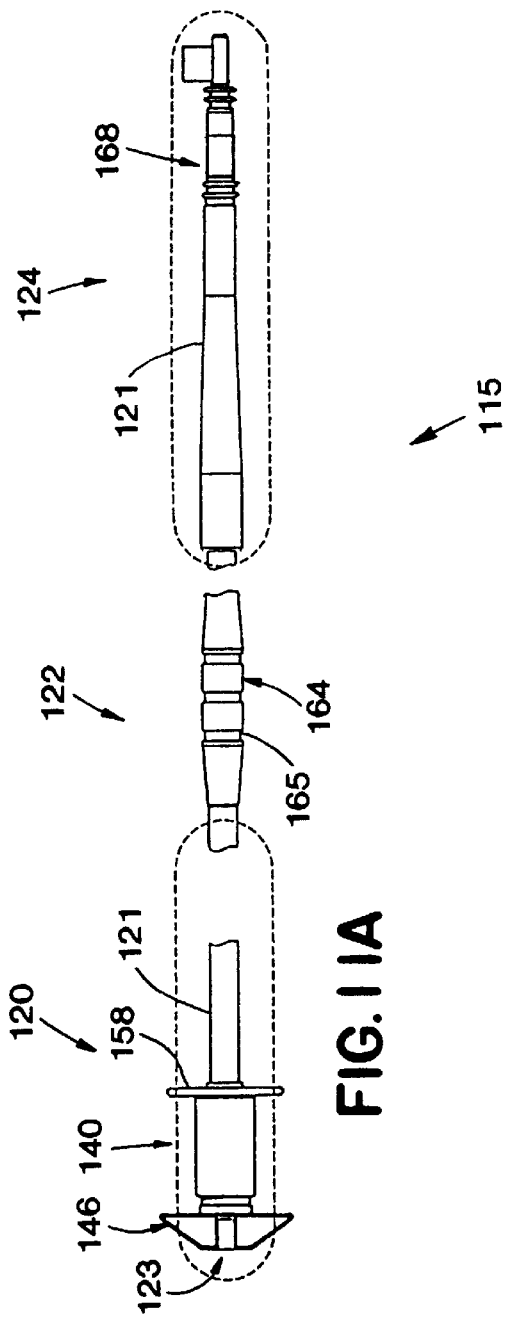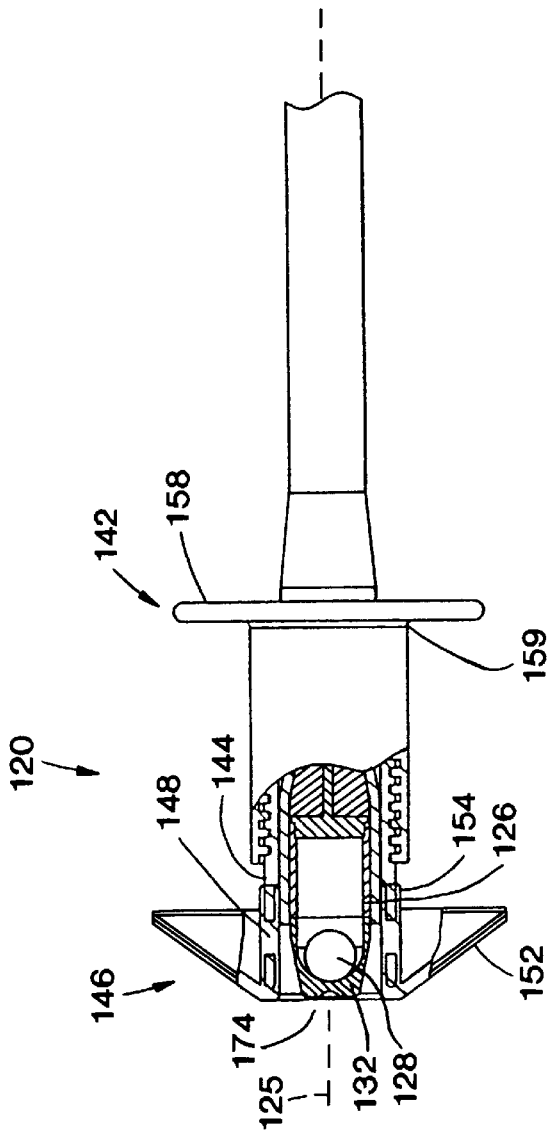

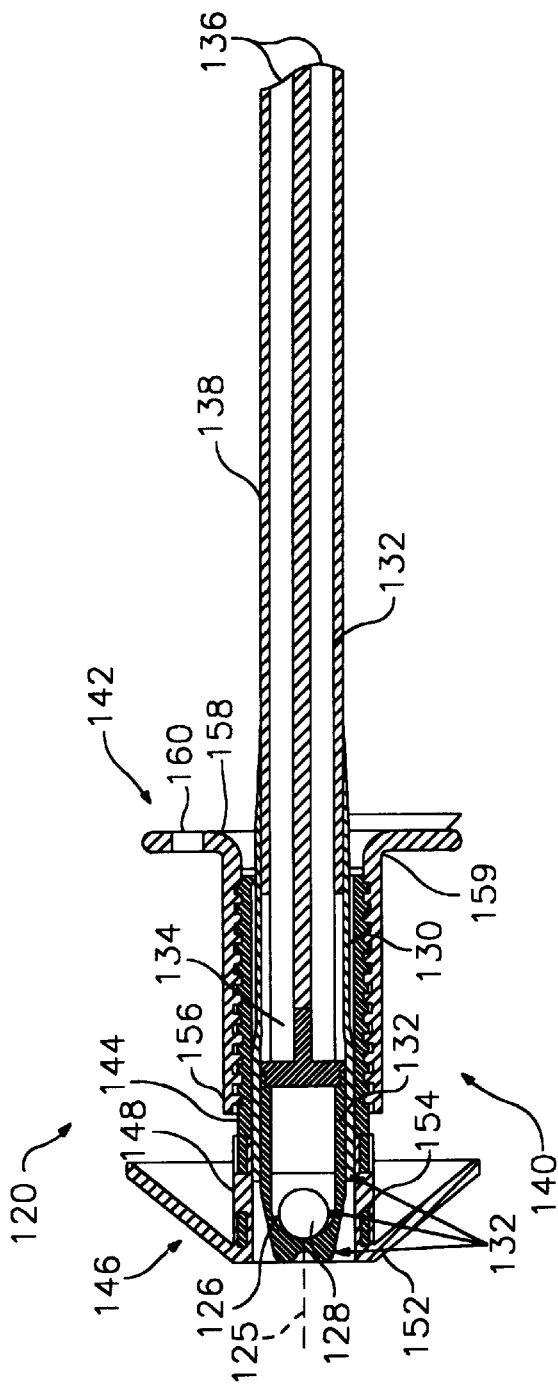
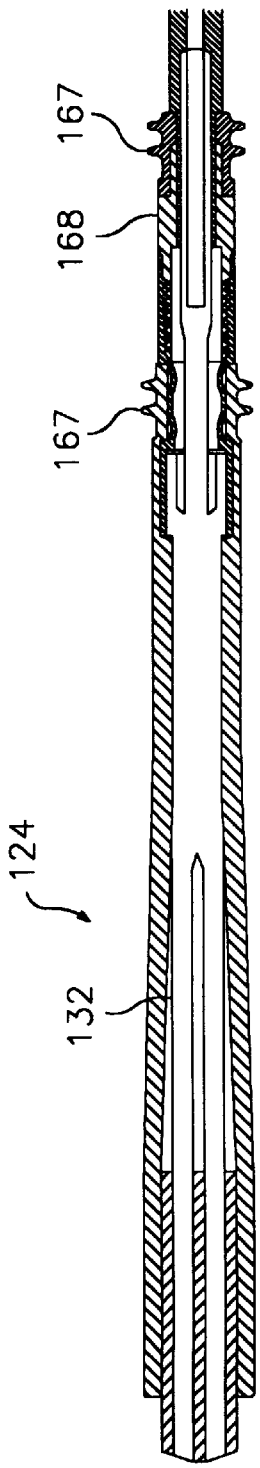

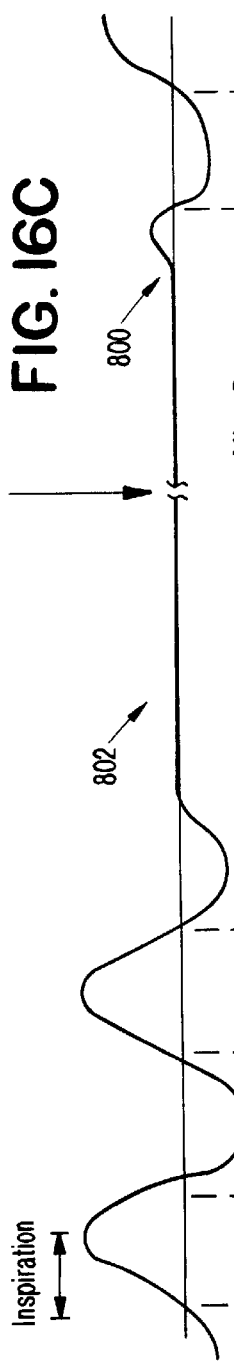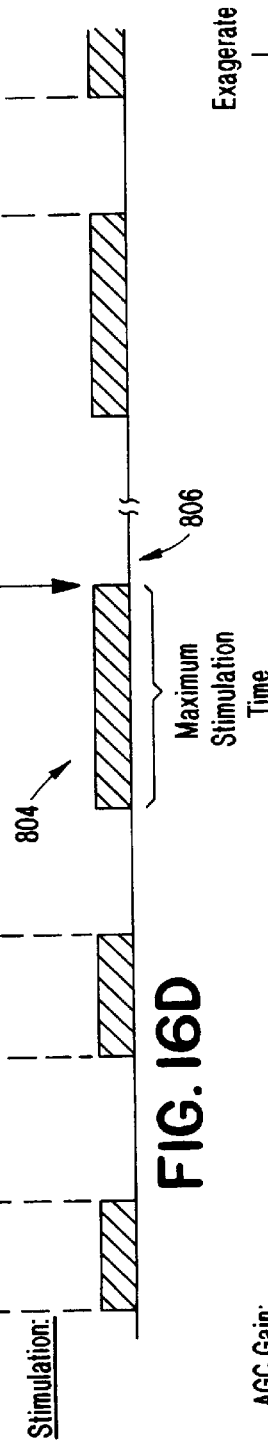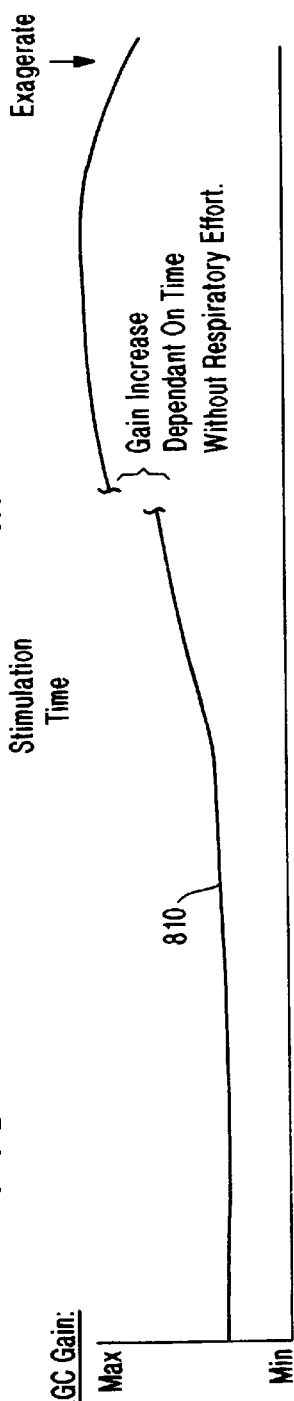

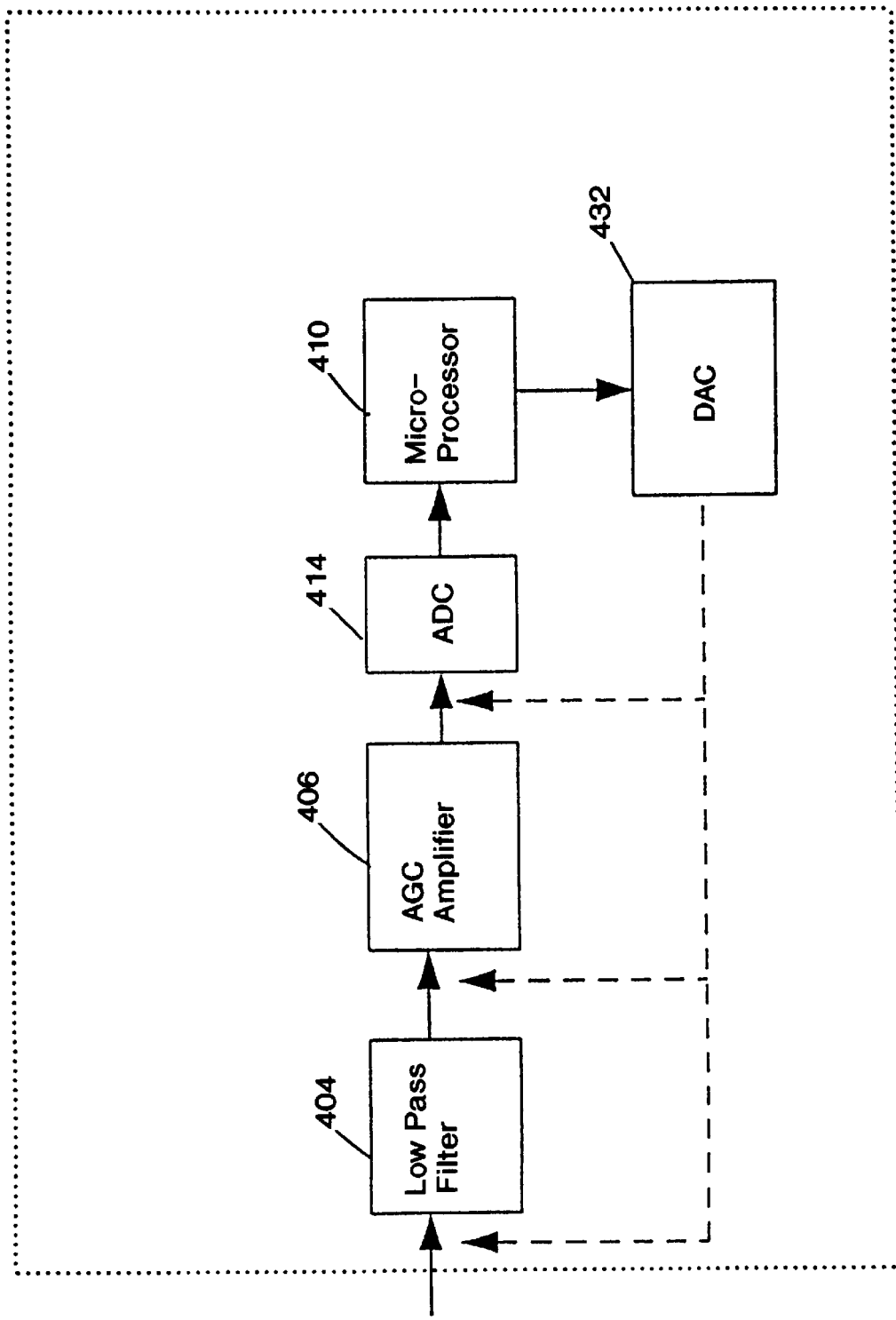

DIAGNOSTIC TESTING METHODS AND APPARATUS FOR IMPLANTABLE THERAPY DEVICES

FIELD OF THE INVENTION

The present invention relates generally to medical devices and methods of testing such devices. More particularly, the present invention pertains to self diagnostic testing methods for use with therapy devices and systems.

BACKGROUND OF THE INVENTION

Sleep apnea, an airway disorder, has been known for some time as a medical syndrome in two generally recognized forms. The first is central sleep apnea, which is associated with the failure of the body to automatically generate the neuromuscular stimulation necessary to initiate and control a respiratory cycle at the proper time. Work associated with employing electrical stimulation to treat this condition is discussed in Glenn, "Diaphragm Pacing: Present Status", Pace, V.I, pp 357–370 (July-September 1978).

The second sleep apnea syndrome is known as obstructive sleep apnea. Ordinarily, the contraction of the dilator muscles of the upper airways (nose and pharynx) allows their patency at the time of inspiration. In obstructive sleep apnea, the obstruction of the airways results in a disequilibrium between the forces which tend to collapse airways (negative inspiratory transpharyngeal pressure gradient) and those which contribute to their opening (muscle contraction). The mechanisms which underlie the triggering of obstructive apnea include a reduction in the size of the superior airways, an increase in their compliance, and a reduction in the activity of the muscle dilator. The muscle dilators are intimately linked to the respiratory muscles and these muscles respond in a similar manner to a stimulation or a depression of the respiratory center. The ventilatory fluctuations observed during sleep (alternately hyper and hypo ventilation of periodic respiration) thus favors an instability of the superior airways and the occurrence of oropharyngeal obstruction. In sleep apnea the respiratory activation of the genioglossus muscle has been particularly noted to be ineffective during sleep. The cardiovascular consequences of apnea include disorders of cardiac rhythm (bradycardia, auriculoventricular block, ventricular extrasystoles) and hemodynamic (pulmonary and systemic hypertension). This results in a stimulatory metabolic and mechanical effect on the autonomic nervous system. The syndrome is therefore associated with an increased morbidity (the consequence of diurnal hypersomnolence and cardiovascular complications).

A method for treatment of sleep-apnea syndrome is to generate electrical signals to stimulate those nerves which activate the patient's upper airway muscles in order to maintain upper airway patency. For example, in U.S. Pat. No. 4,830,008 to Meer, inspiratory effort is monitored and electrical signals are directed to upper airway muscles in response to the monitored inspiratory effort. Or, for example, in U.S. Pat. No. 5,123,425 to Shannon, Jr. et al., a collar contains a sensor to monitor respiratory functioning to detect an apnea episode and an electronics module which generates electrical bursts to electrodes located on the collar. The electrical bursts are transferred transcutaneously from the electrodes to the nerves innervating the upper airway muscles. Or, for example, in U.S. Pat. No. 5,174,287 issued to Kallok, sensors monitor the electrical activity associated with contractions of the diaphragm and also the pressure within the thorax and the upper airway. Whenever electrical activity of the diaphragm suggests that an inspiration cycle is in progress and the pressure sensors show an abnormal pressure differential across the airway, the presence of sleep apnea is assumed and electrical stimulation is applied to the musculature of the upper airway. Or, for example, in U.S. Pat. No. 5,178,156 issued to Wataru et al., respiration sensing includes sensors for sensing breathing through left and right nostrils and through the mouth which identifies an apnea event and thereby triggers electrical stimulation of genioglossus muscle. Or, for example, in U.S. Pat. No. 5,190,053 issued to Meer, an intra-oral, sublingual electrode is used for the electrical stimulation of the genioglossus muscle to maintain the patency of an upper airway. Or, for example, in U.S. Pat. No. 5,211,173 issued to Kallok et al., sensors are used to determine the effectiveness of the stimulation of the upper airway and the amplitude and pulse width of the stimulation are modified in response to the measurements from the sensors. Or, for example, in U.S. Pat. No. 5,215,082 issued to Kallok et al., upon sensing of the onset of an apnea event, a stimulation generator provides a signal for stimulating the muscles of the upper airway at a varying intensity such that the intensity is gradually increased during the course of the stimulation. Or, for example, in U.S. Pat. No. 5,483,969 issued to Testerman et al., stimulation of an upper airway muscle is synchronized with the inspiratory phase of a patient's respiratory cycle using a digitized respiratory effort waveform. A fully implantable stimulation system is described in Testerman et al. with a sensor implanted in a position which has pressure continuity with the intrapleural space such as the suprasternal notch, the space between the trachea and esophagus or an intercostal placement.

However, even with these modes of respiratory disorder treatment, there remain many practical difficulties for implementing them and other therapy treatments in medically useful systems. In particular, it is important that therapy systems, for example, systems including neuromuscular stimulators such as used in treating respiratory disorders, and other systems used for various therapy applications, be reliably operated. Various testing devices for medical devices, such as stimulators, and various fault indicating devices are available. However, such devices typically do not provide for diagnostic or operability testing on a regular basis. For example, if an implantable stimulator for treatment of respiratory disorders is utilized, particularly when such a system is operated when a patient is asleep, operability of the device should be tested regularly to determine if the system is performing its desired function. For example, it should be regularly verified and the patient given feedback that appropriate sensing upon which treatment is based is being performed. Further, for example, with respect to a patient undergoing respiratory disorder treatment, the patient should be comfortable that the amplitude of stimulation is adequate for performing the treatment associated with such stimulation. Thus, there is a need in the art for providing such diagnostic self testing for various therapy systems, including systems for treating respiratory disorders.

SUMMARY OF THE INVENTION

A testing method for use with a patient stimulation system in accordance with the present invention includes providing a stimulation system including a patient control unit. The patient control unit initiates and terminates treatment periods. The method further includes automatically providing at least one period of stimulation to stimulate the patient upon initiating a treatment period.

In one embodiment, the stimulation system is for providing stimulation to treat respiratory disorders. Further, after the automatic provision of the period of stimulation, the system does not permit patient stimulation for a predetermined period of time. In another embodiment, the stimulation system is an implantable system and the patient control unit uses telemetry to initiate the system.

A stimulation system in accordance with the present invention includes stimulation means for providing stimulation of a patient during a treatment period. A patient control unit initiates and terminates treatment periods and the stimulation means automatically provides at least one period of stimulation to stimulate the patient upon initiation of a treatment period.

A system test method for use with a therapy system in accordance with the present invention includes providing a therapy system having a plurality of components; the therapy system physiologically interacting with a patient. The method further includes performing, internally to the system, a diagnostic self test of a component of the therapy system to determine if the component is functioning properly at a time when the therapy system is not interacting physiologically with the patient.

In one embodiment of this method, the therapy system includes a patient control unit for initiating therapy to the patient during a treatment period. Further, the diagnostic self test of the component is automatically performed upon initiation of the treatment period by the patient.

In another embodiment of this method, the therapy system includes an input circuit for receiving a sensed signal characteristic of a physiological parameter of the patient and an output circuit for generating a therapy output for physiological treatment of the patient. A feedback signal from the output to the input is used to perform the self test of the component.

In another embodiment of this method, the therapy system includes an input circuit for receiving a sensed signal characteristic of a physiological parameter of the patient and an output circuit for generating a therapy output for providing therapy to the patient. A therapy output is generated for providing therapy to the patient. An effect of the therapy on the patient due to the therapy output is measured using the sensed signal and the effect resulting from the therapy output is verified.

A system for use in testing a therapy system in accordance with the present invention is also provided. The system includes a therapy system having a plurality of components; the therapy system for physiologically interacting with a patient. The system further includes means for performing, internally to the system, a diagnostic self test of a component of the therapy system to determine if the component is functioning properly at a time when the therapy system is not interacting physiologically with the patient.

BRIEF DESCRIPTION OF THE DRAWINGS

FIG. 2a shows a respiratory effort waveform and indicated phases of the respiratory effort waveform. FIG. 2b shows a graph of a respiratory airflow waveform with FIG. 2c showing the corresponding respiratory effort waveform.

FIG. 7 is a diagram of one embodiment of the physician programming unit shown in block form in FIG. 6.

FIG. 8 is a diagram of one embodiment of the patient programming unit shown in block form in FIG. 6.

FIG. 9 is a diagram showing one embodiment of the IPG/stimulator shown in block form in FIG. 6.

FIGS. 11a–11d are various views of one embodiment of the sensor shown in block form in FIG. 6. FIG. 11a is a side view of the sensor, FIG. 11b is a cutaway view showing the sensing element portion of the sensor with the sleeve subassembly of the sensor cut partially away, FIG. 11c is a cross-section view of the sensing element portion of the sensor, and FIG. 11d is a cross-section view of the connector portion of the sensor.

FIG. 13b is a flow diagram of the IPG-ON block of the flow diagram of FIG. 13a.

FIG. 13c is a flow diagram of the Onset Detection block of the flow diagram of FIG. 13a.

FIG. 13d is a flow diagram of the Offset Detection During Stimulation block of the flow diagram of FIG. 13a.

FIG. 13f is a flow diagram of the Suspension, Artifact, Therapy Delay block of the flow diagram of FIG. 13a.

FIG. 13g is a flow diagram of the AGC Adjust block of the flow diagram of FIG. 13a.

FIG. 16c shows a central sleep apnea occurring between cycles of respiratory effort.

FIG. 16d illustrates stimulation periods for treatment of the central sleep apnea occuring in FIG. 16c.

FIG. 16e shows AGC gain for the respiratory signal shown in FIG. 16c during the central sleep apnea.

FIGS. 20a–d are block diagrams of various internal diagnostic self tests for the system shown in FIG. 18.

DETAILED DESCRIPTION OF THE EMBODIMENTS

The following description relates generally to therapy systems including implantable therapy and stimulation systems. Although many portions of this description are particularly applicable to the treatment of respiratory disorders, such as sleep apnea, by administering stimulation of musculature in synchrony with detected periodic events of the respiratory cycle, many portions of the system are equally applicable to other therapy systems. For example, automatic gain control, diagnostic testing, and methods for conserving energy are applicable to one or more other therapy systems such as, for example, drug delivery systems, blink stimulation systems, and cardiac related systems.

Figure 1:
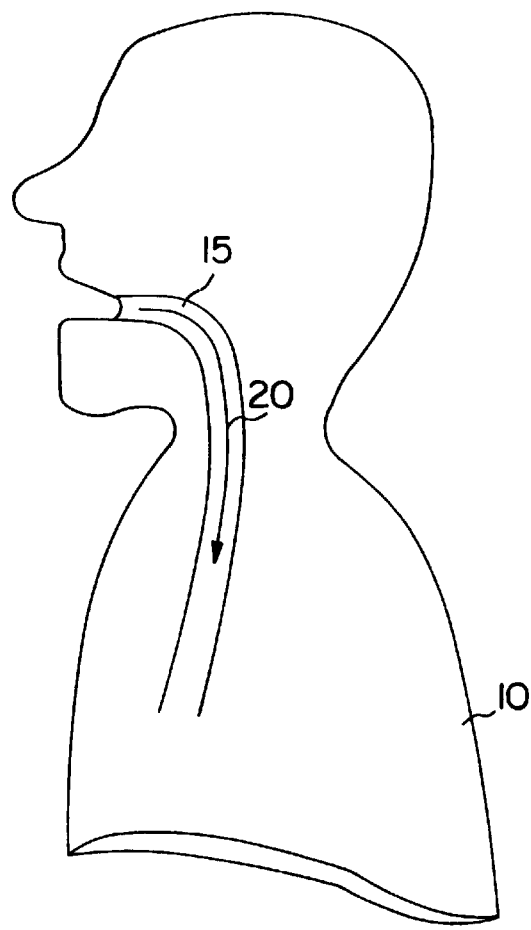
FIG. 1 is a side sectional diagram of a patient having normal respiratory activity.
Figure 2A:
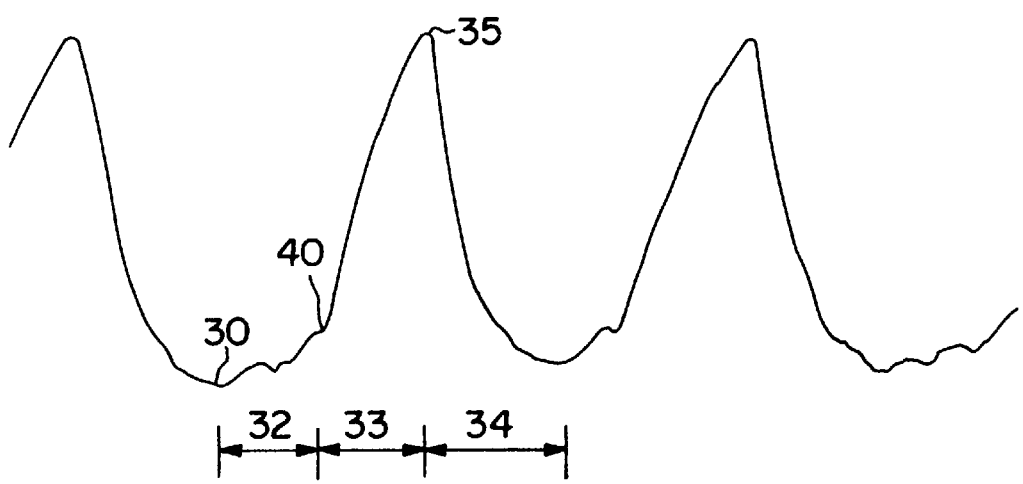
FIGS. 2a–c are graphs of normal respiratory waveforms (shown with full normal inspiration at the peak).
Figure 2B:
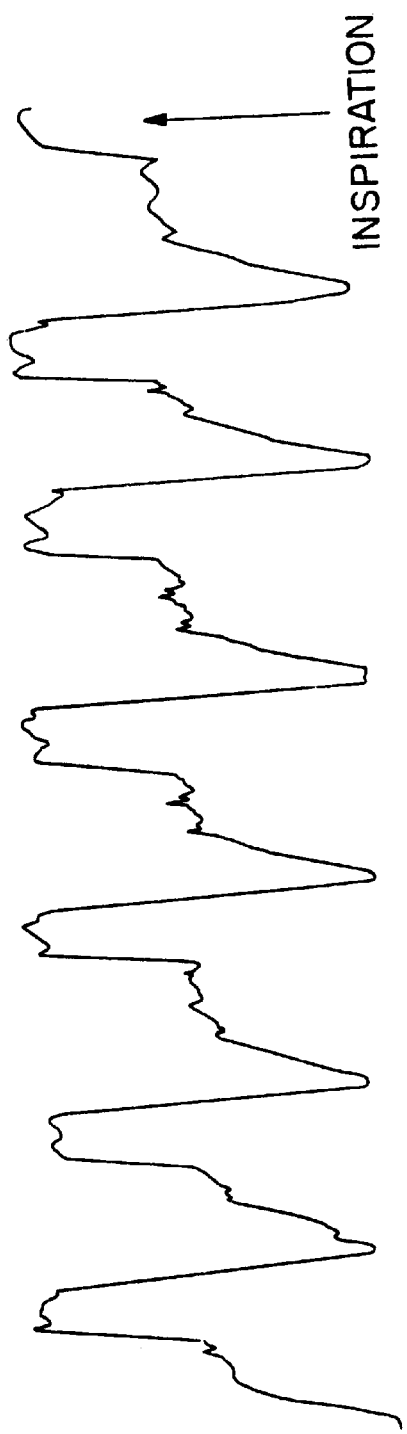
Figure 2C:
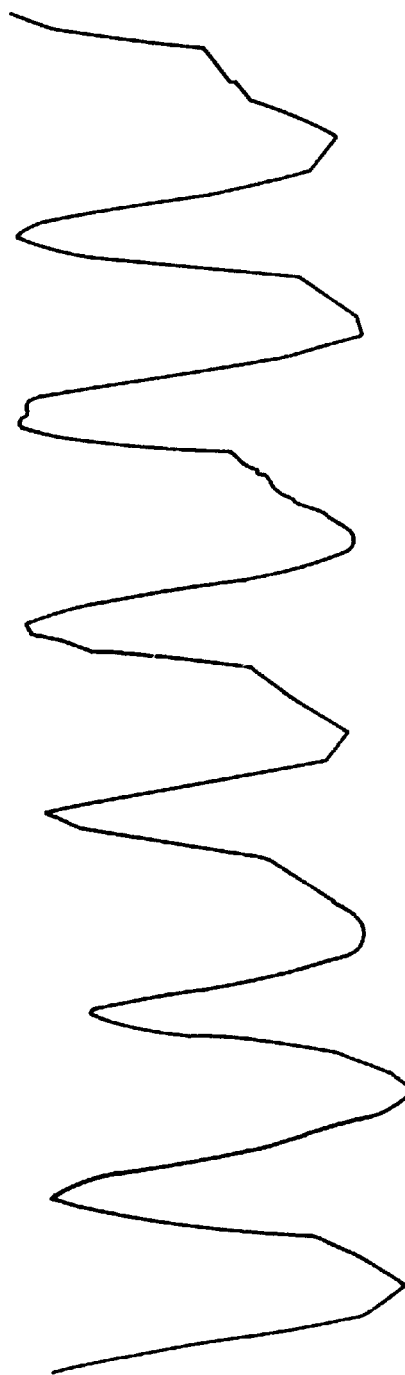

With respect to the synchronization of stimulation to the respiratory cycle of a patient to treat respiratory disorders, such synchronized stimulation requires a suitable respiratory sensor, proper placement of the respiratory sensor, and signal processing capability for converting the sensed respiratory effort signal from the sensor to a stimulation signal for use in stimulating the patient. In FIG. 1 and FIGS. 2a–c, normal respiratory activity is depicted. In FIG. 1, a patient 10 has an airway 15 which remains patent during inspiration of air 20. FIG. 2a shows a typical respiratory effort waveform for two complete respiratory cycles. This analog waveform can be generated by various transducers such as, for example, a belt transducer worn snugly about the chest of the patient as used for detection and analysis of sleep apnea in sleep laboratories, an implanted pressure sensor such as that described in detail below, or any other transducer that provides a respiratory effort signal adequate for analysis to detect critical points thereof for use in the treatment of respiratory disorders, such as sleep apnea. Each wave of the waveform is characterized by a negative peak 30 on completion of expiration, a positive peak 35 on completion of inspiration (i.e. inspiration offset) and a turning point 40 which indicates the onset of inspiration (i.e. inspiration onset). Each wave of the waveform can therefore be separated into a period of respiratory pause 32, an inspiratory phase 33 and an expiratory phase 34. Respiratory effort waveforms having similar identifiable characteristics can be provided by monitoring other physiological signals such as intrathoracic pressure, intrathoracic impedance or electromyographic potentials. Other characteristics of the waveform could also be identified in connection with tracking and analyzing the respiratory waveform to monitor respiratory activity in sleep apnea treatment. In normal respiration, the respiratory effort waveform is related to airflow as set forth in FIGS. 2b and 2c. In FIG. 2b a trace of normal respiratory airflow from a flow transducer is shown while FIG. 2c shows the corresponding trace of the normal respiratory effort which produces the airflow.

Figure 3:
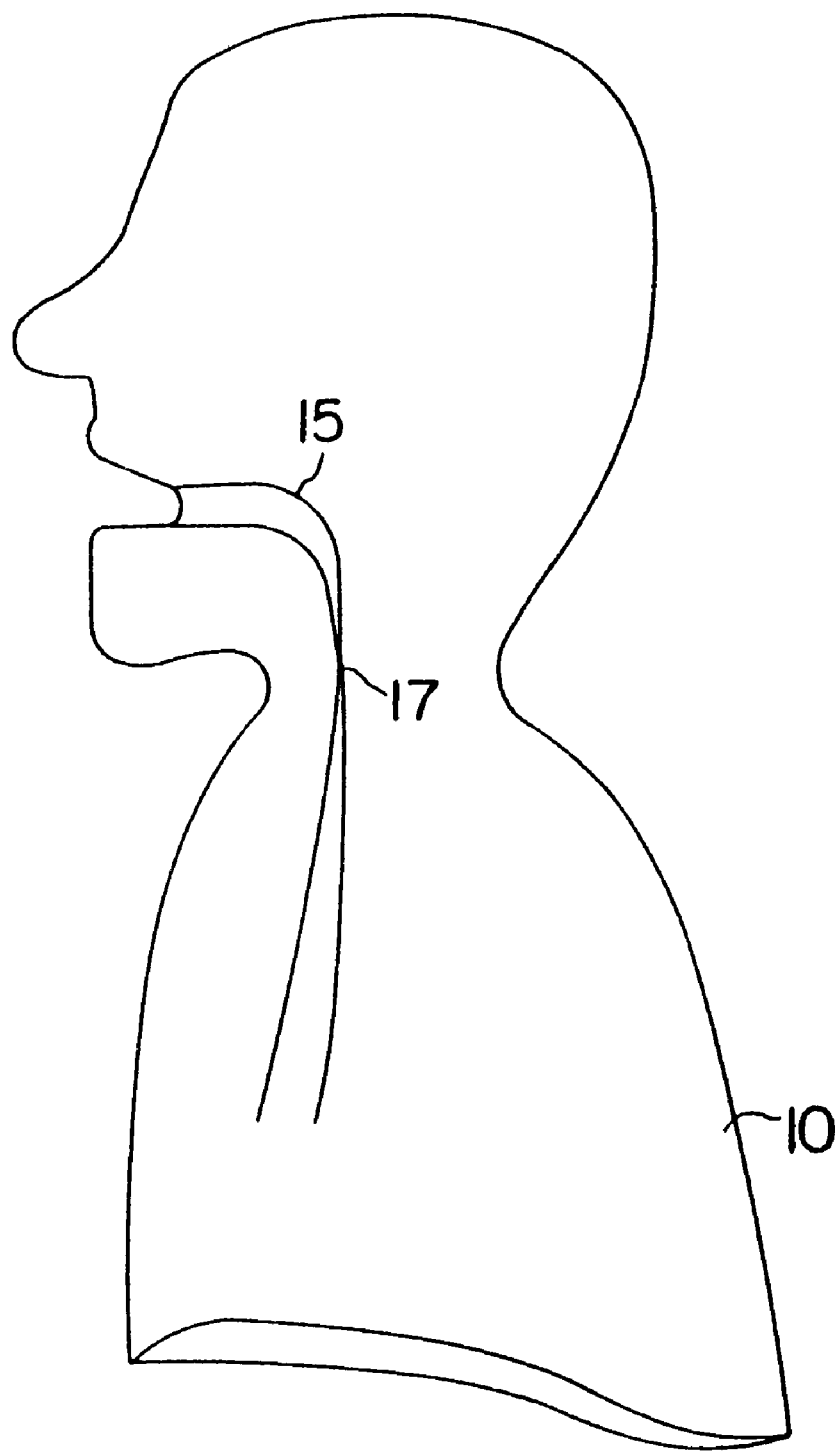
FIG. 3 is a side sectional diagram of the patient of FIG. 1 at the onset of obstructive apnea.
Figure 4A:
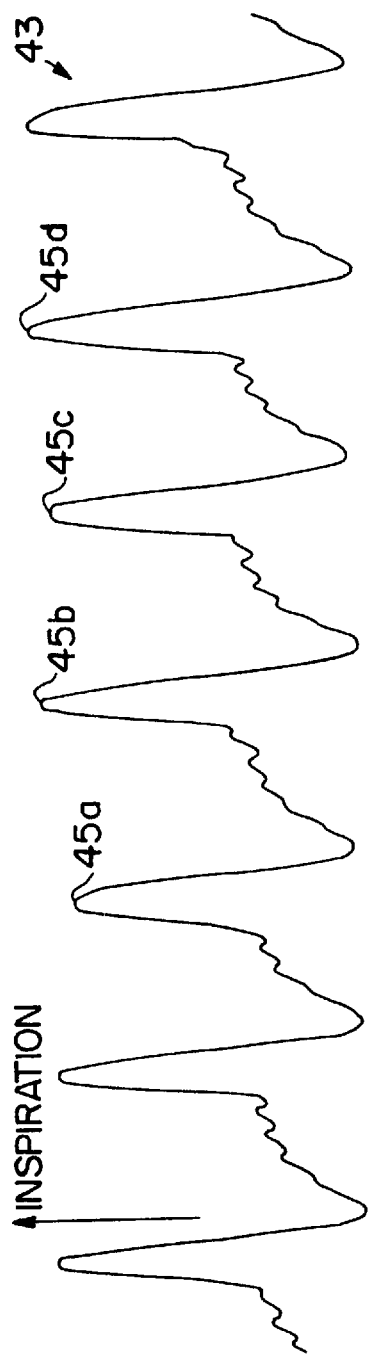
FIGS. 4a and 4b are respiratory waveforms of inspiratory effort showing normal inspiratory effort (FIG. 4a) and the change in normal inspiratory effort at the onset of an apnea event (FIG. 4b).
Figure 4B:
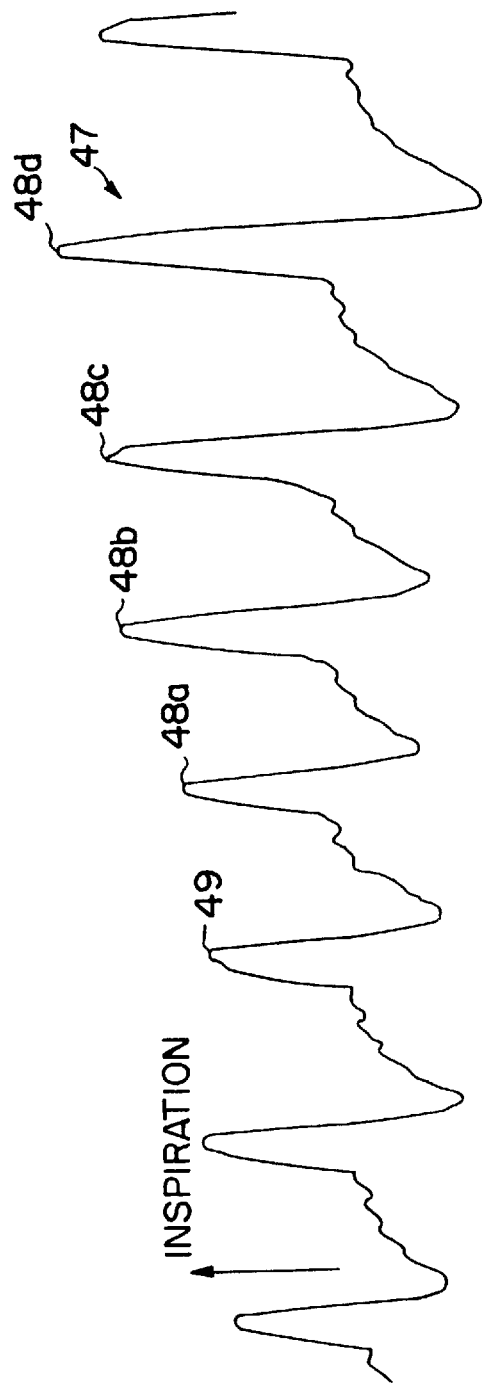

In FIGS. 3 and 4b, respiration in the same patient at the onset of an obstructive sleep apnea event is depicted. FIG. 3 shows the patient 10 and airway 15 with an airway obstruction 17 that is characteristic of an obstructive apnea event. FIG. 4a shows that in a normal respiratory effort waveform 43, the inspiratory peaks 45a–d are of approximately the same amplitude. By comparison in FIG. 4b, in a waveform 47, the inspiratory peaks 48a–d become significantly greater in amplitude at the onset of obstructive apnea than the immediately preceding inspiratory peak 49. This is reflective of the increased inspiratory effort undertaken by the patient in response to the difficulty of breathing through the obstructed airway.

Figure 4C:
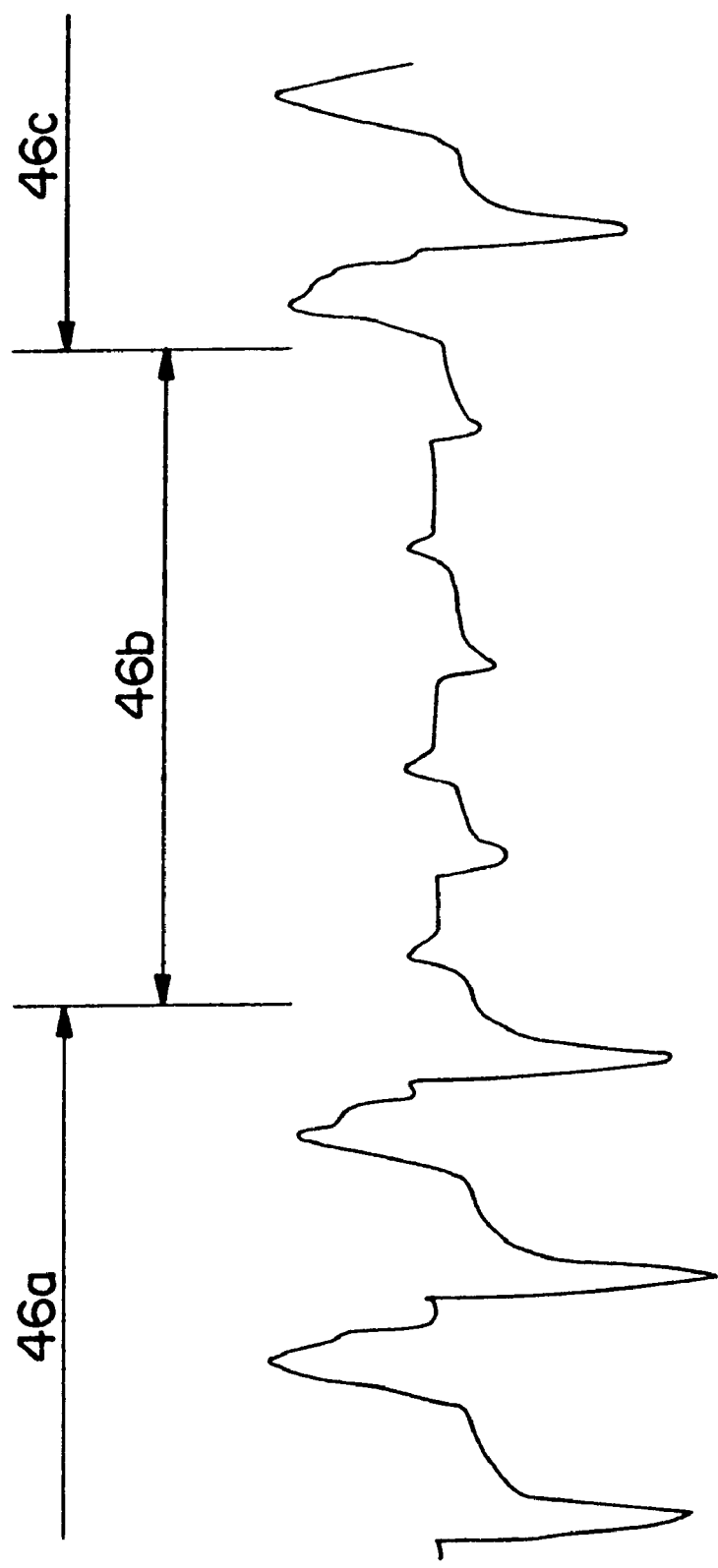
FIG. 4c is a respiratory waveform showing respiratory airflow (as opposed to the respiratory effort waveform shown in FIGS. 4a and 4b) in a patient during an apnea event.

In treatment of sleep apnea, the increased respiratory effort is avoided by synchronized stimulation of a muscle which holds the airway open during the inspiratory phase. Preferably, the muscle stimulated is an upper airway muscle, such as the genioglossus muscle stimulated by a cuff electrode placed around the hypoglossal nerve. However, there may be other upper airway muscles or nerves which can be used for stimulation to perform the same function and also other nerves or muscles apart from the upper airway which may be stimulated, such as the diaphragm, to treat respiratory disorders, such as, for example, sleep apnea. The effect of this stimulation on obstructive sleep apnea can be seen in the airflow trace of FIG. 4c. During a first period indicated as 46a, stimulation is enabled producing a normal respiratory airflow. During a second period indicated as 46b, stimulation is disabled causing obstruction of the airway and reduction in airflow volume (apnea). During a third period indicated as 46c, stimulation is resumed, restoring patency to the airway and increasing airflow volume.

Figure 5:
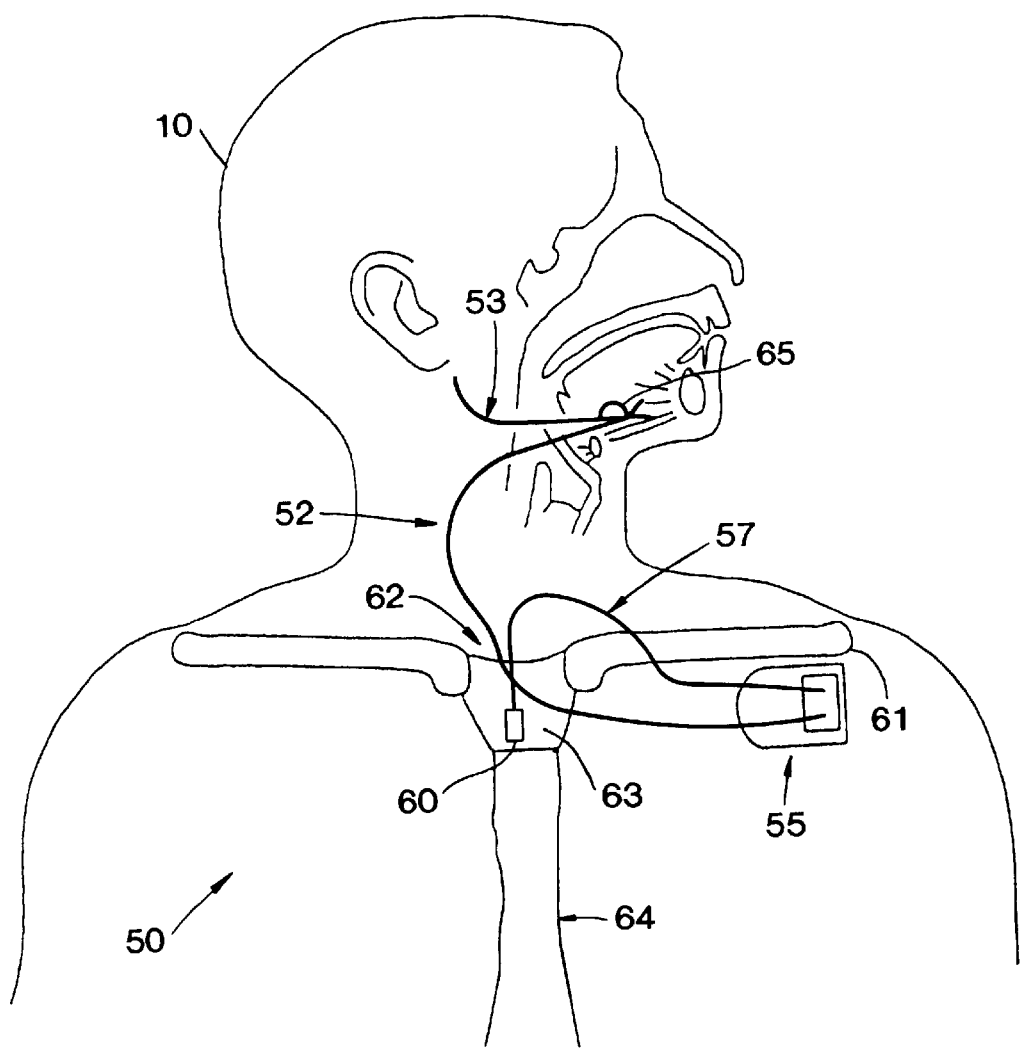
FIG. 5 is a front sectional diagram of a patient showing the implantable components of the stimulation system in accordance with the present invention.
Figure 6:
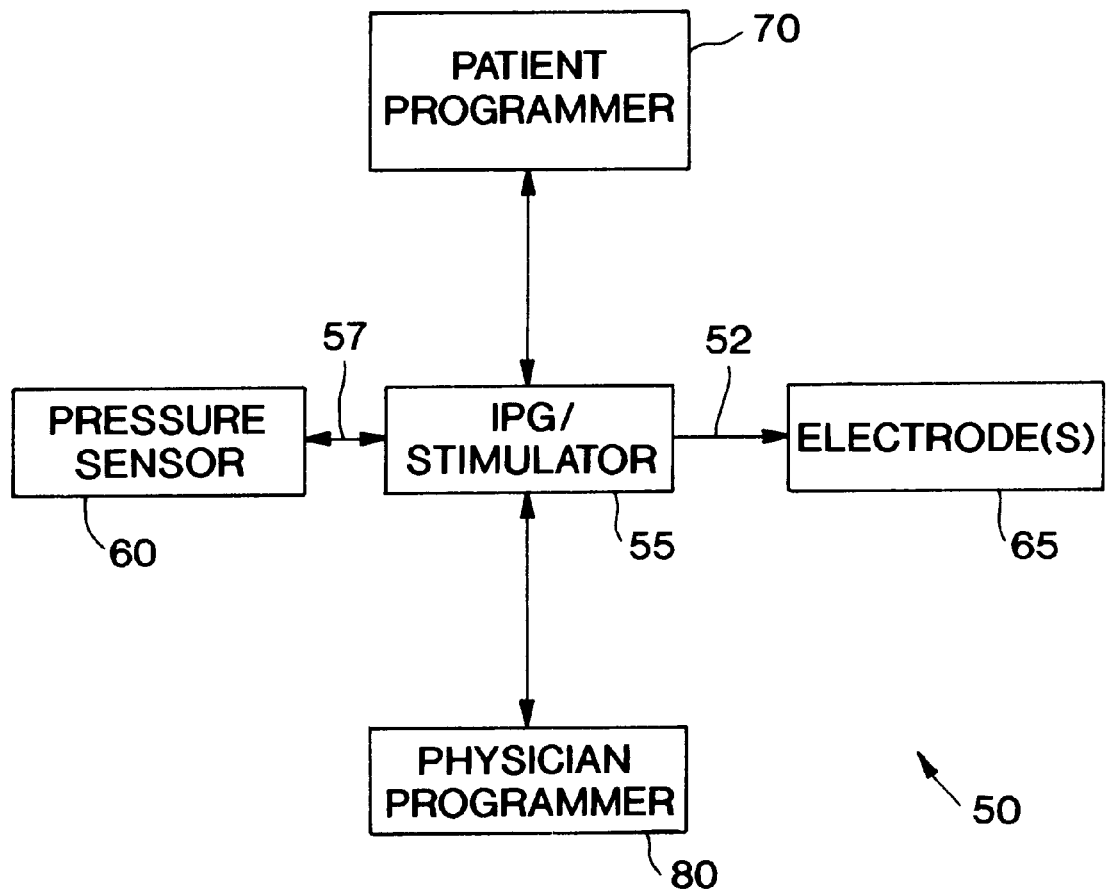
FIG. 6 is a block diagram of the stimulation system shown in FIG. 5 further including physician and patient programming units.

Components, and one implantable configuration, of an implantable stimulation system 50 for providing inspiration synchronous stimulation treatment of sleep apnea are shown in FIG. 5. A block diagram of these components and other associated programming components of the system 50 for treating sleep apnea is shown in FIG. 6. As shown in FIG. 5, inspiration synchronous stimulation is controlled by the implantable pulse generator (IPG)/stimulator 55. IPG 55, also shown in FIG. 9, provides inspiration synchronized stimulation, e.g. one or more stimulation pulses, through stimulation lead 52 to an electrode or electrode system 65 placed around the hypoglossal nerve 53 for stimulation of the genioglossus muscle of the upper airway. The electrode or electrode system 65 may be positioned with respect to any other respiratory nerve, or other nerve or muscle that provides the desired stimulation result for the respiratory disorder treated. The IPG 55, i.e. stimulator/controller, receives respiratory effort waveform information via a sensor lead 57 from a respiratory sensor or transducer 60 sensing the respiratory effort of a patient 10.

One associated component of system 50 includes a physician programmer 80, such as a laptop computer having programming software and communication capabilities for communicating with the IPG 55, and which is capable of programming the IPG 55 with various parameters in order to adapt the system for treatment of a particular patient. The system 50 of FIG. 5, is therefore adapted to be programmed using the physician programmer 80 as shown in FIG. 7 by telemetry via transmitting/receiving element 81 electrically coupled to the processor based programmer 80. Thereafter, the system 50 is used each night by the patient to prevent the closure of the upper airway during the inspiratory phase of the respiration cycle.

It will be apparent to those skilled in the art that such a system must be made to be easy to use by the patient and since it is used without constant medical supervision, it must be able to adapt to many different operating conditions. Therefore, the system 50 includes another associated component, i.e. patient programmer 70, as shown in FIG. 8. The patient programmer 70 gives the patient the capability to turn the stimulator ON/OFF, adjust the stimulation amplitude within preset limits programmed by the physician and adjust any other stimulation parameters or parameters of the IPG 55 as may be allowed by the physician, such as, for example, stimulation pulse rate, pulse width, dose time, therapy delay time. The patient programmer 70 provides both a visual and audio confirmation of communication with the stimulator and further may include other patient control elements for controlling parameters of the treatment of sleep apnea. In addition, as described further below, the patient turning the power on for initiation of the treatment using the patient programmer 70 starts an automatic self stimulation test and/or an automatic diagnostic self test of the components of the system 50. Such a diagnostic self test may be performed at any time, in addition to the initiation of the treatment period by the patient. Further, such self stimulation test and diagnostic tests are equally applicable to other therapy systems in addition to the treatment of respiratory disorders, such as sleep apnea.

The pressure sensor or respiratory transducer 60, may be a dynamic relative pressure sensor such as that disclosed in U.S. Pat. No. 4,407,296 to Anderson or U.S. Pat. No. 4,485,813 issued to Anderson et al which are incorporated herein by reference in their entirety. The pressure sensor 60 is surgically implanted in a region that has pressure continuity with the intrapleural space such as the suprasternal notch, the space between the trachea and esophagus or attached to either of the trachea or esophagus, an intercostal placement, or secured as shown in FIGS. 10a–10e in a position for sensing pressure at the posterior side of the manubrium as described in further detail below. The suprasternal notch 62 and manubrium 63 of sternum 64 as shown in FIG. 5, are well known structures on the upper chest that are in anatomical continuity with the intrapleural space. It is also well known that changes in intrapleural pressure provide a characteristic respiratory effort waveform. The location for placement of the sensor is, at least in part, chosen as a function of delay, i.e. propagation time of a pressure waveform characteristic of respiratory effort propagating from the respiratory point of origin to the sensor position and as a function of the amount of filtering necessary to achieve a usable sensed signal at a particular location, i.e. filtering necessary to remove waveforms other than the waveform of the sensed characteristic, such as cardiac waveform activity.

Preferably, the pressure sensor 60 utilized is a pressure sensor assembly or sensor lead 115 similar to the sensor lead sold under the trade designation of Medtronic Model 4321, available from Medtronic, Inc., Mpls., Minn. as modified and represented in FIGS. 11a–11d. The pressure sensor assembly 115 includes a sensing section 120, a lead anchoring section 122, and a connector section 124. A flexible lead body 121 forms a part of each section. The sensing section 120 includes, as shown in the detail views of FIGS. 11b and 11c, a relative pressure sensing element 126 which is mounted at an open distal end 123 of assembly 115 opposite the connector section 124. The relative pressure sensing element 126 senses respiration pressures through the use of piezo-electric crystals attached to a sensor diaphragm lying perpendicular to a longitudinal axis 125 extending through assembly 115. Pressures are transmitted to the diaphragm through the portholes 128 on both sides of the sensing element 126. Pressure transmits from the portholes 128 to the diaphragm via a medical adhesive 132, such as silicone rubber, which fills the nose cavity of the pressure sensing element 126. The sensor is driven, for example, with a fixed bias current on which the AC pressure signal is coupled onto. Such a fixed sensor bias can range from about 8 $\mu$A to about 100 $\mu$A. Such a sensor has a nominal output of about 3 mV/mmHg over the usable bandwidth of about 0.1 to about 100 Hz.

The sensing element 126 has coil leads 136 electrically connected thereto. The coil leads 136 are provided within bilumen tubing 138. The bilumen tubing 138 at the sensor section end and the sensing element 126 are positioned in a flexible tube 130 by medical adhesive 132 which also fills the cone of the sensing element 126 and covers the outer portions of the sensing element 126. There is no exposed metal surface of the sensing element 126 and the sensor is electrically isolated from the patient.

As shown in FIG. 11d, a connector assembly 168, such as, for example, a bipolar IS-1 compatible connector assembly, is electrically connected to the lead body 121, such as by crimping, to coil leads 136 in connector section 124 of the sensor assembly 115. Any connector assembly may be utilized that is compatible with a connector port of the IPG 55. The connector includes sealing rings 167 to ensure that body fluids do not disrupt the sensor assembly 115 and IPG 55 connection.

A sleeve attachment subassembly 140 has the sensing element 126 and a portion of the lead body 121 positioned therein. The sleeve subassembly extends from a distal surface 174 of the sensing element 126 at the open distal end 123 to beyond the interface between the lead body 121 and sensing element 126. The sleeve attachment subassembly 140 includes an outer threaded sleeve 142, an inner threaded sleeve 144, and a soft umbrella ring 146. The sleeve attachment subassembly 140 is mounted on the outer surface of the flexible tube 130 with medical adhesive 132. The inner surface of the inner threaded sleeve 144 is abraded to provide adhesion with the medical adhesive 132 to stably mount the sensing element 126 in the subassembly 140. The inner threaded sleeve 144 has holes 148 about the longitudinal axis therethrough for molding a flexible element, i.e. soft umbrella ring 146, about the distal open end of the inner threaded sleeve 144.

The soft umbrella ring 146 may be formed of silicone rubber and includes a flexible outer umbrella portion 152 that extends outward relative to the longitudinal axis and rearwardly relative to the distal open end of the inner threaded sleeve 144 and a fixed portion 154 of the umbrella ring 146. The flexible outer umbrella ring 152 performs the function of preventing tissue and bone growth over the distal open end 123 of the sensor assembly 115 when implanted. The soft umbrella ring 146 is preferably formed of a radio opaque material so that it can be seen in imaging processes throughout implantation and explanation. Further, the umbrella ring 146 may include a treatment to prevent tissue and bone overgrowth of the sensor 126. Such treatment may include treatment with a steroid, such as heparin, chemical coatings, surface roughening, or any other treatment that reduces such tissue and bone overgrowth.

The flexible element, i.e. umbrella ring 146, may be of any configuration that prevents bone and tissue overgrowth. Further, if the sensor is implanted into a drill hole in the manubrium as described below, the flexible element must be capable of being inserted and removed through the drilled hole. For example, the flexible element may be a donut shape or a simple flange extending outward relative to the longitudinal axis 125 at the distal open end of inner threaded sleeve 144.

The outer threaded sleeve 142 includes a threaded portion 156 and an unthreaded flange portion 158 extending substantially perpendicular to and outward relative to the longitudinal axis 125 of the sensor assembly 115. The outer and inner threaded sleeves 142 and 144 are utilized for adjusting the length of the subassembly 140 along the longitudinal axis 125. Further, they provide for anchoring the sleeve subassembly, i.e. securing the sensor, in the manubrium as described further below with the unthreaded flange portion 158 of the outer threaded sleeve 142 providing means for direct or indirect contact at the anterior side of the manubrium and with the flexible element 146 providing for direct or indirect contact at the posterior side of the manubrium. The adjustability is important as the thickness of the manubrium varies from patient to patient. One or more holes 160 in the flange portion 158 are available for anchoring the sensor section 120 by suture to tissue or by bone screw to the anterior side of the manubrium. The outer threaded sleeve 142 and the inner threaded sleeve 144 are preferably formed of stainless steel, but can be any biocompatible material, preferably a rigid biocompatible material.

In alternative configurations, the flange portion 158 may include a soft cover thereabout or may be formed of a different shape as long as it still performs the function of direct or indirect contact with the manubrium to hold the sensing element 126 in position and/or includes means for attachment by a bone screw, suture, or other securing means. For example, the flange portion 158 may be a tab structure or multiple tabs extending away from and substantially perpendicular to the longitudinal axis 125 from the end 159 of threaded portion 156.

Further, the adjustability function of the inner and outer sleeves 142 and 144 may be provided by any structure that allows a length of the sleeve to be adjusted and then capable of being fixed at a particular length. For example, two telescoping members or sliding members may be used with, for example, a ratchet technique coupling the two and providing fixation at a particular length.

The anchoring section 122 includes lead body anchoring sleeve 164 slidably mounted on the lead body 121 and having suture grooves 165 for the anchoring of the lead body 121 when implanted. The lead body 121 is flexible such that it can make a sharp right angle from the sleeve subassembly 140 at the anterior region of the manubrium when the sensor assembly 115 is implanted to avoid skin erosion and bulge thereat. For example, the lead body 121 may include pentifilar conductor coils 136 in a bilumen silicon tubing.

Alternatively, the lead body 121 may include a right angle attachment at the anterior region of the manubrium 63 for providing direction to the lead body as it extends from the drilled hole at the anterior of the manubrium 63.

One skilled in the art will recognize that various connection techniques for connecting the sensing element 26 to the IPG 55 may be utilized. For example, fiber optic connection may be used, RF techniques may be used, and also techniques using the body mass itself to propagate a signal between components may be used. With use of at least some of these connection techniques, a lead extending from the anterior of the manubrium would not be present. Without the need for a lead, the sleeve subassembly 140 for positioning and anchoring the sensor in the drilled hole of the manubrium 63 could take the form of any mounting element having an adjustable length. The mounting element would no longer need to have an opening therethrough, such as a sleeve, but could take the form of, for example, a spring loaded elongated member with one open end for holding the sensor. In other words, the mounting elements used to mount the sensing element may take any elongated form with an adjustable length and elements for securing it in the manubrium hole by direct or indirect contact with the anterior and posterior surfaces of the manubrium.

Figure 10A:
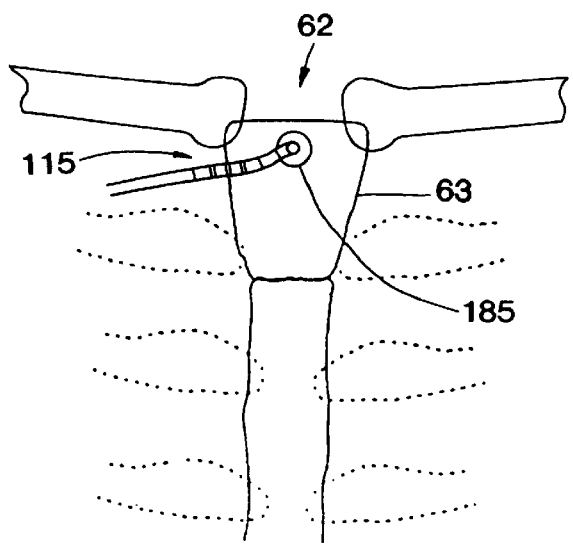
FIGS. 10a–10e are illustrations showing various positions or configurations for mounting the sensor shown in block form in FIG. 6 for sensing respiratory effort at a position in proximity to the posterior surface of the manubrium.
Figure 10B:
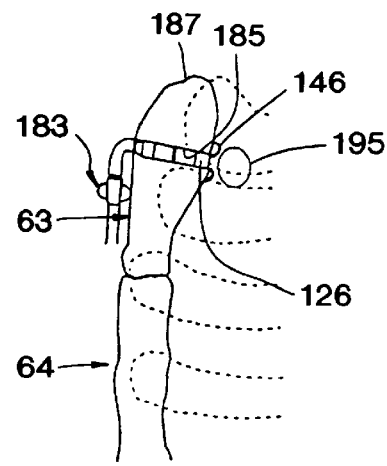

The pressure sensor 60, such as pressure sensor assembly 115, or any other suitable sensor for providing a signal characteristic of respiratory effort, may be implanted in various positions, such as those previously mentioned and further including attachment to the esophagus or trachea or in a position therebetween, or to any other soft tissue in the suprasternal notch. Various positions for the sensor are described in U.S. patent Ser. No. 08/310,177 entitled "Method and Apparatus For Detecting and Treating Obstructive Airway Disorders" incorporated herein by reference in its entirety. Further, the sensor 60 may be positioned as shown in the FIGS. 10a–10e. Preferably, the pressure sensor assembly 115 is implanted through a drilled hole in the manubrium 63 as shown in FIGS. 10a and 10b. However, the sensor assembly 115 could be implanted through the sternum 64 at any location thereof or through any other bone such that the sensing element 126 is in communication with the intrathoracic region or a region with pressure changes characteristic of respiratory effort.

As shown in FIG. 10b, the brachiocephalic vein 195, also known as the inominant vein, is located in a region on the posterior side of the manubrium 63 and erosion of the vein is to be avoided. The present invention is configured to allow sensing in the region where this vein is located. The pressure sensor 60 is positioned in proximity to the vein, however, the term in proximity to the vein means that the sensing element is positioned in the region of the vein but is configured and/or positioned such that erosion of the vein is avoided.

To implant the pressure sensor assembly 115, a small pocket posterior to the manubrium 63 via the suprasternal notch 62 is created, such as by blunt dissection. A hole 185 is drilled perpendicularly through the superior aspect of the manubrium 63 and at the midline of the manubrium 63. It is desired that the sensor element 126, be placed near the top 187 of the manubrium 63 so that the pocket created on the posterior side of the manubrium 63 is minimized lessening surgical excavation risk and lessening the effects of cardiac signals which are stronger at lower portions. Further, by implanting the sensor assembly 115 toward the top of the manubrium 63, the implanter can see the position of the umbrella ring 146 easily, especially with mirrors. During drilling, a retractor is placed on the posterior side of the manubrium 63 to protect intrathoracic structures. Although placement of the sensing element 126 near the top 187 of the manubrium is preferred, the sensing element may be positioned anywhere along the length of the sternum 64, although the manubrium is preferred. More preferably, the sensing element is positioned about 0.5 cm to about 3 cm from the top 187 of the manubrium.

When implanting the sensor, the length of the sensor section 120 of the pressure sensor assembly 115 (i.e. length of subassembly 140) is maximized by turning the outer threaded sleeve 142 with respect to the inner threaded sleeve 144 of the sleeve attachment subassembly 140. The sleeve attachment subassembly 140 of the sensing section 120 is then inserted in the drilled hole 185 and the sensor section length is adjusted such that the soft umbrella ring 146 is in direct or indirect contact with the posterior surface of the manubrium 63. When the sensor section 120 is inserted into the drilled hole 185, the umbrella ring 146 collapses or is compressed against the side of the sleeve subassembly 140 and will spring outward upon protruding into the posterior side of the manubrium 63. The umbrella ring portion 152 will act as an anchor and will prevent bone and tissue growth over the sensor opening. The implanter can utilize a finger to make sure the umbrella ring 146 is flush with the posterior surface and to stabilize the sensor while the outer threaded sleeve 142 is turned to adjust the length of the sleeve attachment subassembly 140 of the sensor section 120 to the thickness of the patient's manubrium 63. The distal tip 174 of the sensing element 126 should protrude in the range of about 1 mm to about 3 mm posteriorly from the manubrium 63. A position less than 1 mm results in a greater chance of tissue or bone overgrowth of the sensing element 126. The distal tip 174 of the sensing element 126 is flush with the open end of the inner threaded sleeve 144. The sensor assembly 115 can then be anchored on the anterior side of the manubrium by a suture or bone screw through the hole 160 of the unthreaded flange 158 of the outer threaded sleeve 142. The lead body 121 can be anchored with use of suture grooves 165 on the anchoring sleeve 164.

With the IPG 55 implanted in a position on the upper chest, such as just below the clavicle 61 as shown in FIG. 5, the lead body 121 of the pressure sensor assembly 115 is inserted in a tunnel created from the manubrium 63 to a pocket created for implanting the IPG 55. When the IPG 55 is implanted, the connector section 124 of the pressure sensor assembly 115 is connected to sensor port 58 of the IPG 55.

Figure 10C:
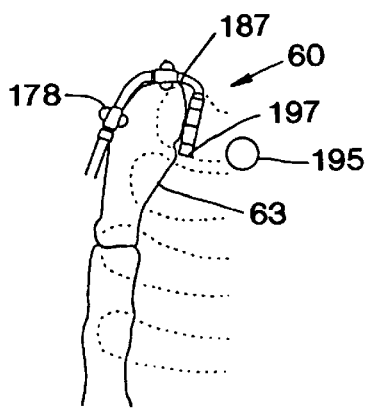
Figure 10D:
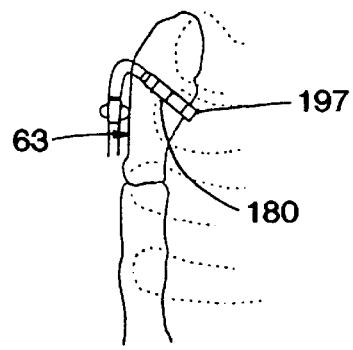
Figure 10E:
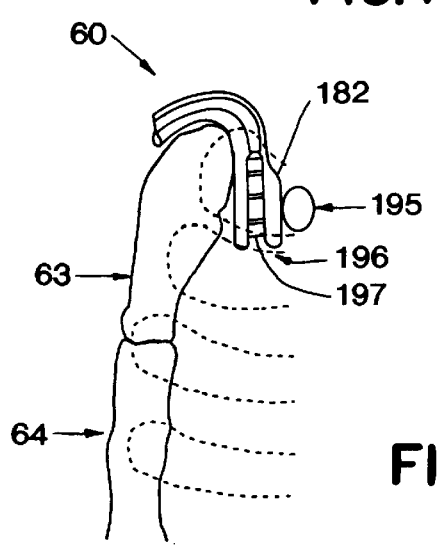

FIGS. 10c–10e show alternative configurations for implanting the pressure sensor 60 of the implantable stimulation system 50. As shown in FIG. 10c, a pressure sensor 60 has a sensing element 197 positioned posterior to the manubrium 63 with the lead body extending over the top 187 of the manubrium 63. The lead is then brought down the anterior portion of the manubrium 63. Various anchors 178 are utilized to hold the sensing element 197 in place behind the manubrium 63.

As shown in FIG. 10d, the sensor 60 is positioned in a manner similar to that shown with respect to the drill through technique described with reference to FIGS. 10a and 10b. However, in this configuration, the drill hole 180 is made at an angle through the manubrium 63.

As shown in FIG. 10e, the sensor 60 is positioned substantially as described in FIG. 10c. However, in order to protect against erosion of fragile veins posterior of the manubrium, the sensing element 197 and a portion of the lead body extending therefrom are covered with a soft guard 182. The guard 182 may serve the function of anchoring the sensor 60 as well as preventing any erosion of the brachiocephalic vein 195. The distal end 196 of the guard is open.

As demonstrated by the various configurations shown, many various positions for implant of the sensor 60 are possible behind the manubrium yet while avoiding the fragile veins. The present invention contemplates the positioning and securing of various sensing elements with respect to the manubrium 63 to sense pressure or any other characteristic for obtaining a respiratory effort waveform at a region posterior of the manubrium 63. The sensing elements are preferably placed in close proximity to the posterior surface of the manubrium 63.

The electrode or electrode system 65 of the implantable stimulation system 50 may be any conventional electrode system for stimulation of muscles to treat respiratory disorders, such as sleep apnea. As previously described, although various respiratory muscles may be stimulated, stimulation of the genioglossus muscle is utilized herein for treatment of sleep apnea. For example, the electrode system 65 utilized may be a Model 3990B Half Cuff Nerve Electrode available from Medtronic, Inc., Mpls., Minn.

This electrode and other suitable electrode configurations are described in U.S. Pat. No. 5,344,438 to Testerman et al., entitled "Cuff Electrode" and incorporated entirely by reference herein. This electrode is utilized for placement around a respiratory motor nerve, such as the hypoglossal nerve 53, with the stimulation lead 52 for connection to the stimulation port 59 of IPG 55 as shown in FIGS. 5 and 9. One or more stimulation pulses are delivered to the electrode 65 by the IPG 55 and transferred to the nerve resulting in opening of the airway during respiration. It should be readily apparent to one skilled in the art that any suitable electrode for stimulating the desired muscle may be utilized with the stimulation system 50 according to the present invention. For example, the electrode may be a full cuff electrode or any other electrode configuration for capturing a respiratory motor nerve, such as the hypoglossal nerve. Further, with respect to any other neuromuscular stimulation systems which may benefit from the present inventions described herein, the electrode(s) may include any electrode(s) that provide the desired stimulation for such systems.

Figure 12A:
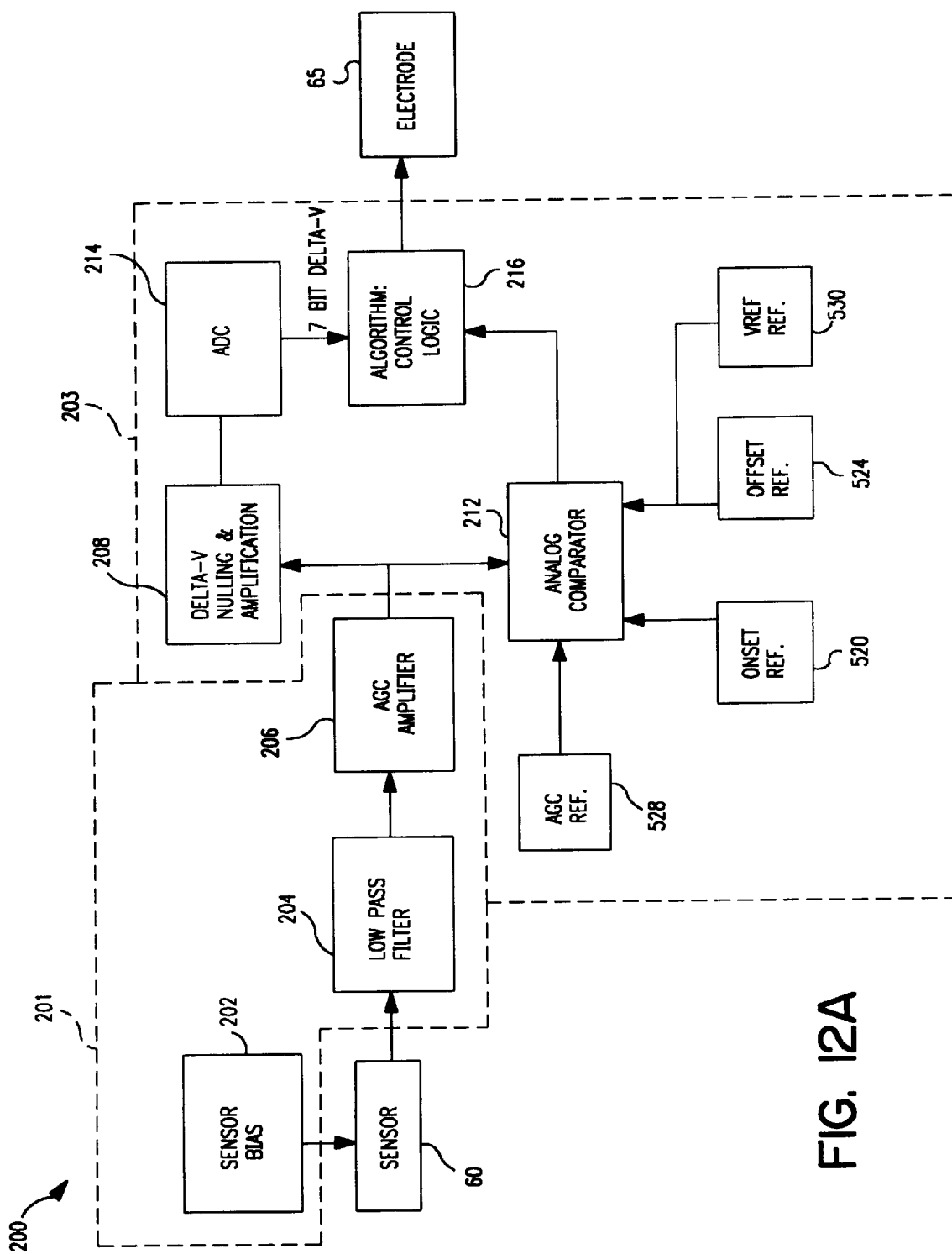
FIG. 12a is a first embodiment of a block diagram of the signal processing circuitry of the IPG/stimulator shown in block form in FIG. 6, implemented in logic, for receiving the respiratory effort signal from the sensor and providing an inspiration synchronized stimulation signal to the electrode in accordance with the present invention.

The IPG 55 includes signal processing circuitry 200, including detection algorithm or control logic 216, as shown in block diagram form in FIG. 12a, respectively, and functionally shown in the flow diagrams of FIGS. 13a–13g. The signal processing circuitry 200 processes the respiratory effort signal provided by the pressure sensor 60, such as pressure sensor assembly 115, and provides inspiration synchronized stimulation via electrode or electrode system 65 for the treatment of respiratory disorders.

To achieve adequate treatment of sleep apnea, the stimulation is initiated by detection of inspiration onset, for example, within a predetermined time of the actual physiological onset, for example 200 ms. Sensing onset 200 ms early (i.e. 'predictive') is desired. Stimulation is terminated as a function of a detected inspiration offset. Slight errors of approximately 300 ms or less in timing causing early offsets, late offsets, or early onsets are typically permitted by the treatment system. Late onsets, however, are preferably no later than, for example, 200 ms. The requirement that detection of onsets be no later than, for example, 200 ms, is necessary to avoid airway obstruction prior to stimulation. The timing to recruit a muscle to overcome obstructions which occur prior to stimulation force such a requirement. The present invention provides means for predictively detecting onsets to meet this requirement. In addition to rigid timing requirements, the detection algorithm operates reliably in the presence of cardiac artifacts and motion artifacts.

The description herein is set forth in a manner such that stimulation for treatment of sleep apnea occurs substantially continuously and synchronous with inspiration throughout the treatment period, except for time of nonstimulation such as suspension, dose, therapy delay, etc. as determined by the algorithm described below. The treatment period is the time period from when the treatment is turned on to when the treatment is turned off. However, many of the concepts described herein are equally applicable to sleep apnea treatment systems wherein the onset of apnea is detected in some manner and stimulation only performed after such detection of apnea. For example, waveform analysis could be performed to determine when an apnea is about to occur and then treatment by stimulation could be initiated using concepts described herein. Such detection of the onset of sleep apnea is described in U.S. Pat. No. 5,483,969 to Testerman et al. which is incorporated herein by reference in its entirety.

Figure 14:
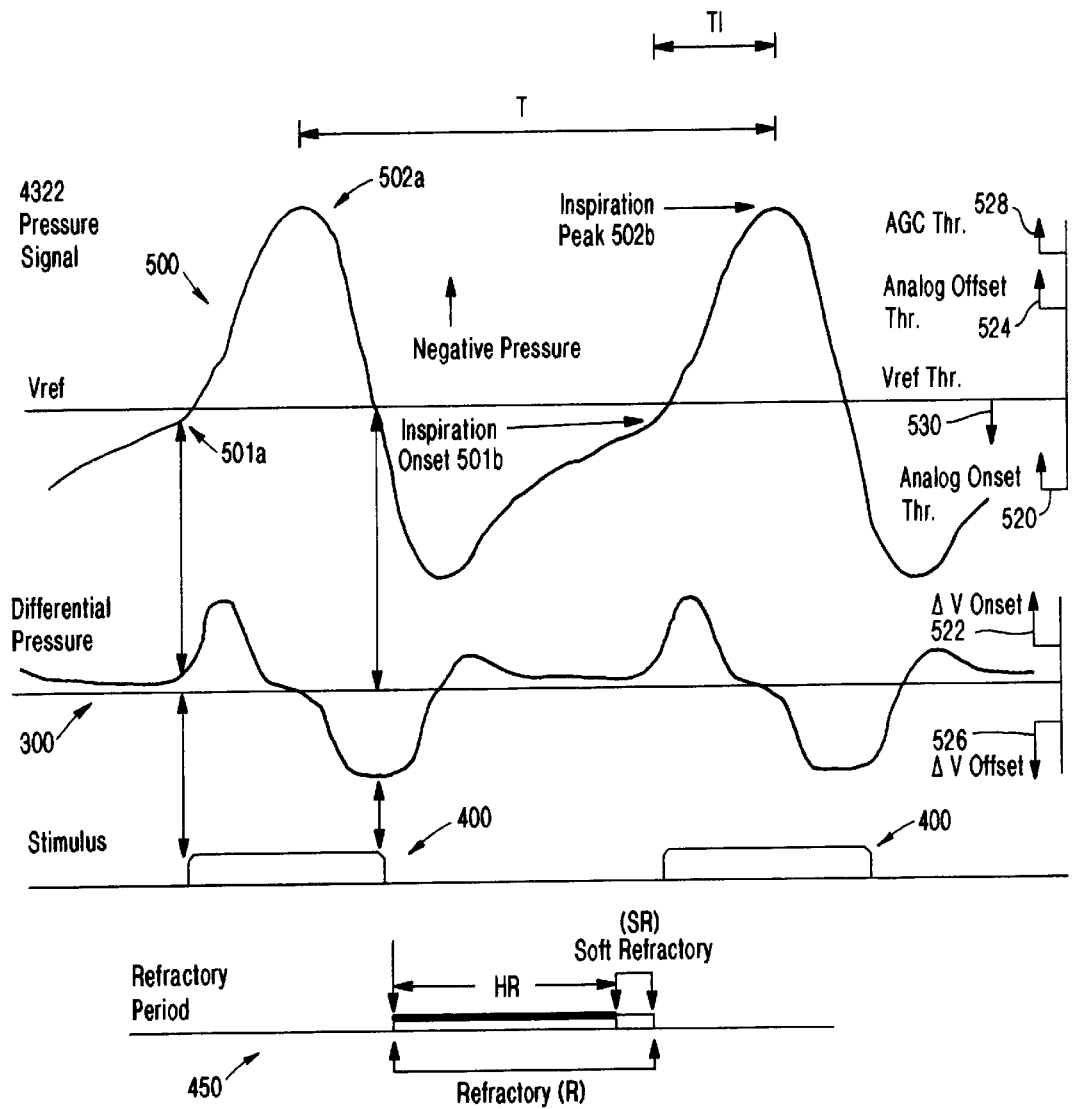
FIG. 14 is a graph showing a normal respiratory effort waveform indicating various critical points detected in accordance with the present invention, various thresholds used in such detection, a normal differential pressure signal, a stimulus signal synchronously applied based on the critical points detected with respect to the respiratory effort waveform, and an illustration showing the definition of a refractory period, all in accordance with the present invention.

The detection algorithm or control logic 216 of the signal processing circuitry 200, which will be described in detail below, makes significant reference to FIG. 14. Therefore, a brief description of FIG. 14 is appropriate at this point to introduce the elements thereof and provide a brief description of some of the functionality of the control logic 216. FIG. 14 includes a normal respiratory effort waveform 500 characteristic of the signal sensed by the pressure sensor 60, a differential pressure signal 300, an illustrative stimulus window 400 during which one or more pulses are generated for treatment of airway disorders synchronized with inspiration onset 501a and inspiration offset 502a, and a refractory period illustration wherein a refractory period (R) is defined during at least a part of the expiratory and pause periods 34 and 32 (FIG. 2a) of the respiratory cycle.

Further, FIG. 14 shows the respiratory period (T) which is represented as the period from inspiration offset 502a to inspiration offset 502b, the time of inspiration (TI) which is shown as the time from inspiration onset 501b to inspiration offset 502b, and a variety of thresholds which are utilized by the detection algorithm/control logic 216 to control and provide inspiration synchronous stimulation. Such thresholds include analog onset threshold 520 and ΔV (i.e. slope) onset threshold 522 used for detection of inspiration onset, analog offset threshold 524 and ΔV offset threshold 526 used for detection of inspiration offset (i.e. latched offset), Vref threshold 530 or zero crossing threshold used for validating or declaring a detected latched inspiration offset, and AGC amplitude threshold 528 used in updating gain of the respiratory signal from the sensor 60.

ΔV is representative of the slope of the respiratory effort waveform 500. For illustration, the ΔV values can be generated by sampling the sensor output during a sample period, such as for example every 10 to 70 ms. The sampled value is then compared to the previously sampled value to obtain the net change in voltage (i.e. change in intrathoracic pressure) over the sample period. The net change, ΔV, is thus the pressure signal slope and therefore, representative of slope of the respiratory effort waveform.

The normal respiratory effort waveform 500 shows the amplitudes and slopes which are characteristic of inspiration onset and offset. The polarity of the voltage respiratory effort waveform 500 in FIG. 14 is inverted with respect to the polarity of the actual physiologic pressure measured by sensor 60. Inspiration is represented as a positive going voltage which indicates a negative inspiration pressure. Expiration is shown as a negative going voltage which indicates a positive expiration pressure. The stimulation system 50 includes automatic gain control (AGC) that references or normalizes the respiratory effort signal. For example, the signal may be normalized such that the positive signal peak is 1.2 volts, baseline (Vref) is 0 volts (DC), and the negative signal peak is at approximately −1.2 volts. In other words, a 2.4 peak to peak signal is provided. The AGC is described in further detail below and is applicable to any variable input signal characteristic of a periodic physiological parameter and is not limited to only the respiratory effort pressure signal described herein. The normalization of such signals is particularly advantageous when used in systems where timing detection is based on comparison to signal thresholds.

Inspiration onset 501 is characterized as a rapid change in slope at an amplitude above a predetermined level, i.e. analog onset threshold 520 (FIG. 14), and is detected by the control logic of the present invention as a function of such characterization. Inspiration offset 502 is characterized by a negative change in slope above a predetermined amplitude, i.e. analog offset threshold 524 (FIG. 14). A sustained non-positive slope and an amplitude above the predetermined amplitude typically indicate an offset 502 and an offset is detected and latched by the control logic of the present invention as a function of such characterization.

Physiological artifacts caused by cardiac pressures and body motions add complexity to the respiratory effort waveform. Cardiac artifacts produce slope changes very similar to onset and offset slope changes. However, the slope is not typically sustained for the same duration. The respiratory amplitude level is typically not altered by the cardiac artifacts. Therefore, the combination of sustained slope and amplitude provides information to differentiate between inspiration events (onsets and offsets) and cardiac artifacts to avoid stimulation at the improper time. The control logic, for example, by using consecutive ΔV samples to detect offsets and onsets, utilizes such characteristics to prevent misdetection of valid onsets and offsets, i.e. offsets and onsets that are not artifact onsets and offsets.

Figure 15:
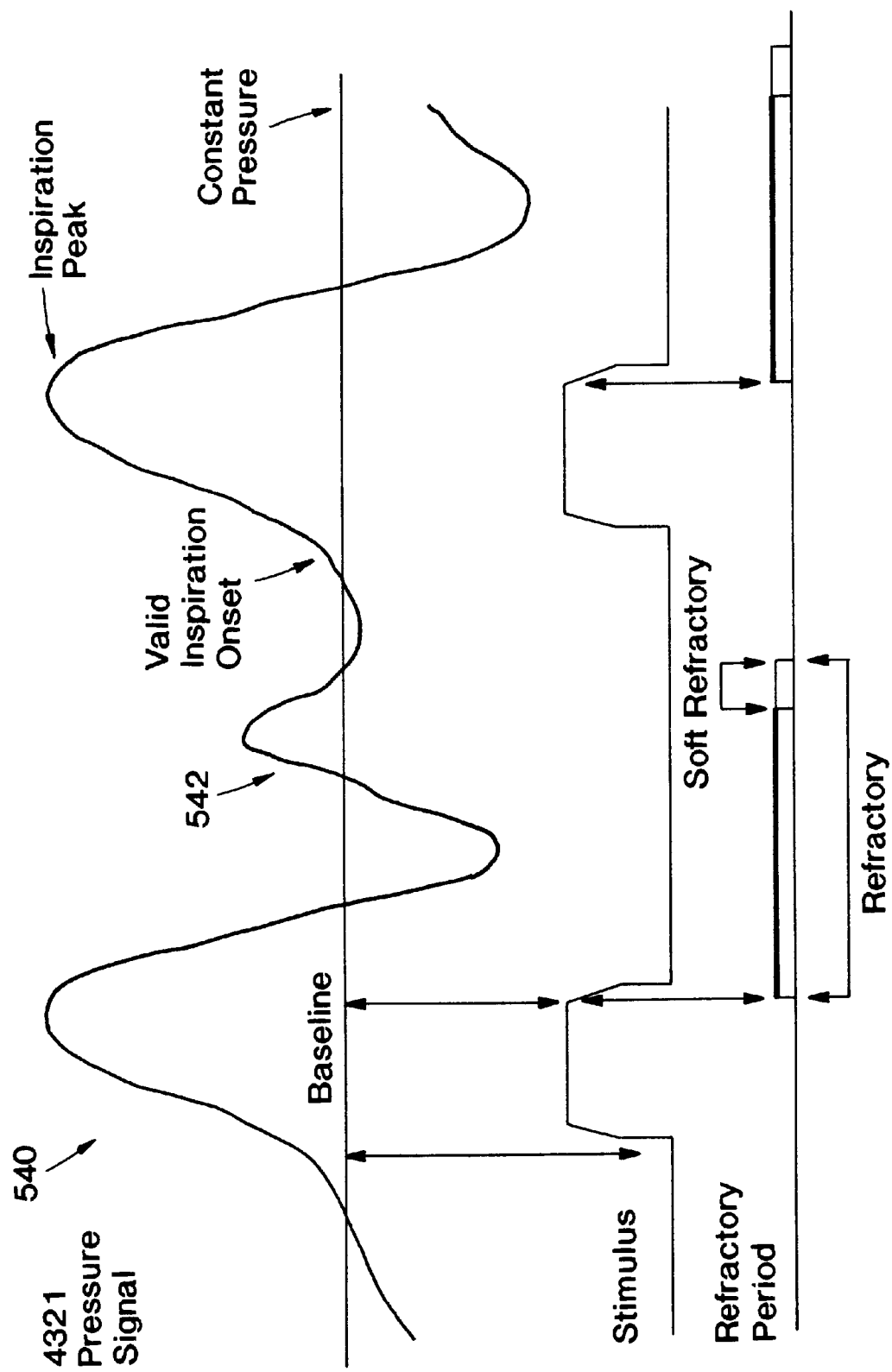
FIG. 15 is a graph showing a respiratory effort waveform having an artifact therein, a stimulus signal applied according to the present invention, and an illustration of the refractory period utilized to reject the artifact as an inspiration onset, all in accordance with the present invention.

Motion artifacts are similar to inspiration in both sustained slope and amplitude. FIG. 15 displays a motion artifact 542 on a respiratory waveform 540. Depending on the source of the artifact (slow or fast body movement, etc.) the slope and amplitude may be sufficient to satisfy the characteristics of either an inspiration onset and/or offset and stimulation based on such an artifact is to be avoided. As illustrated in FIG. 15, the control algorithm in accordance with the present invention utilizing a defined refractory period minimizes stimulation from occurring based on artifacts like artifact 542. Such distinguishing of the artifact from normal respiration will become apparent from the detail description of the control logic 216 below.

The techniques used by the algorithm or control logic 216 to distinguish motion artifacts are based on known physiological parameters of breathing during sleep. First, respiratory rate is known to be very stable and consistent during sleep. For example, a typical breath-to-breath rate variation of 15% has been established, with maximum variations as high as 35%. Periods of wakefulness will have more breath-to-breath variations, coughs, sighs, etc., but stimulation is not necessary nor desirable while the patient is awake. The detection algorithm establishes the presence of a stable respiratory rate or respiratory period in order for stimulation to occur when signal onset characteristics are present, i.e. stimulation is suspended if a stable respiratory rate or respiratory period is not detected. Second, as the ratio between time of inspiration/total respiratory period (TI/T) is generally known, such as for example, between 0.30 and 0.40, a refractory period (i.e. blanking period after inspiration has occurred), that includes both hard and soft refractory periods, is utilized to detect or predict onset at a time just prior to the next expected onset. These two ideologies, along with others as will become apparent from the further detail below, are utilized by the algorithm to reject motion artifacts.

The IPG 55, shown in FIG. 9, is any IPG or stimulator capable of being configured for control of stimulation as required herein for treatment of sleep apnea. The IPG 55 may be, for example, a Medtronic nerve stimulator sold under the trade designation ITREL II Model 7424 or a Medtronic nerve stimulator sold under the trade designation ITREL III Model 7425, both available from Medtronic Inc., Mpls., Minn., modified to include an input from the respiratory sensor 60 and modified to include all the signal processing capabilities as shown in FIG. 12a for control of stimulation as required herein. Each of these nerve stimulators include circuitry for providing a wide range of stimulation therapies which can be used with the present invention. The stimulator utilized should be capable of implementing the signal processing with minimum power consumption. Many various hardware configurations may be utilized to implement the described signal processing circuitry. For example, various designs incorporating hardware, software, processors, analog circuits, digital circuits, combinations of the aforementioned, etc. may be used to perform the necessary signal processing and the present invention is not limited to any particular configuration. Any IPG 55 utilized requires an energy source.

The IPG 55 is implanted in the patient at a location such as shown in FIG. 5. However, any location normally utilized for implanting an IPG can be used for the location of IPG 55 as would be readily apparent to one skilled in the art. A suitable implantable neurostimulator has advanced programmable features permitting mode changes by transcutaneous RF telemetry. The patient-controllable parameters of the IPG's operation, such as the amplitude of stimulation, can therefore be controlled by the patient through a small hand-held telemetry device, i.e. patient programmer 70, shown in FIG. 8. Likewise, the physician can preset additional operational parameters of the IPG 55 through a handheld telemetry device 81 of the physician programmer 80, as shown in FIG. 7, held over the implanted IPG 55.

As shown in FIG. 9, the IPG 55 includes two connector ports 58 and 59. The connector port 58 is for insertion of the sensor lead 57 and the connector port 59 is for insertion of the stimulator lead 52.

FIG. 12a is a first embodiment of a block diagram of the processing circuitry 200 that includes sensor input circuitry 201 necessary to acquire a respiratory signal from the pressure sensor 60 including means for biasing the sensor, filtering the sensor output and providing a normalized sensor signal. Processing circuitry 200 further includes monitoring circuitry 203 for monitoring the sensed signal to synchronize stimulation with respiration.

In this first embodiment, as shown in FIG. 12a, a combination of analog and digital circuits is used. Logic functions are provided without use of a microprocessor, i.e. purely analog and digital circuits. The analog front end or sensor input circuitry 201 for obtaining a respiratory effort signal includes sensor bias 202 required for biasing the pressure sensor 60. The pressure sensor 60, for example, the sensing element 126, requires a stable bias current in the range of 8.8 $\mu$A to 100 $\mu$A. One method of sensor bias 202 includes providing a static bias current in the range of, for example, 15 $\mu$A to 25 $\mu$A. Currents of this magnitude provide the best trade-off in terms of battery life and adequate immunity from noise. Alternatively, a second manner of sensor bias 202 includes providing a duty-cycled bias current. In this manner of operation, for example, a 80 $\mu$A to 100 $\mu$A bias is applied to the sensor just prior to the sampling the respiratory signal. Such duty cycling provides lower power operation, i.e. saves battery life, and provides noise immunity benefits.

The pressure induced AC voltage from the sensor 60 is AC coupled with a high pass filter pole at 0.1 Hz from the sensor bias current to a filter 204, for example, a 2pole, 3 Hz RC low pass filter. The filter 204 is for anti-aliasing the signal prior to providing the signal to the AGC amplifier 206 and to remove the higher frequency edges of non-respiratory artifacts, such as cardiac artifacts, and also motion artifacts.

The AGC amplifier 206 (FIG. 12a) may operate at a sampling frequency using switched capacitor techniques or may be operated continuously. The AGC amplifier 206 is responsible for normalizing the sensor output, such as, for example, to a consistent 2.4 volt peak-to-peak signal. The amplitude of this signal is then sampled and used by the analog threshold comparator 212 for comparison to various thresholds and is presented to the ADC 214 for conversion into digital delta voltage measurements ($\Delta$V's) via the $\Delta$V nulling amplifier 208 for providing an indication of the slope of the waveform. The outputs from the analog comparator 212 and ADC 214 are then utilized by algorithm/control logic 216 to provide inspiratory synchronous stimulation as further described below.

The AGC amplifier 206 compensates for patient-to-patient and inter-patient respiration amplitude variabilities. For example, pressure amplitudes will vary as a patient changes sleeping positions. The AGC amplifier 206 provides adaptivity to the variable amplitudes and thus the physician is not required to program a gain setting. The AGC amplifier 206 also makes the detection algorithm much easier to implement as the thresholds, as described above and also further below, become relative to the normalized peak-to-peak signal and will operate the same even as the true pressure varies throughout the night.

In the first embodiment of processing circuitry 200, the measurement of the pressure sensor signal amplitude is implemented in analog circuitry. The analog amplitude of the pressure signal is measured by comparison to various thresholds and digital outputs are provided to the detection algorithm 216 as a function of such comparisons. Because of the fixed nature of the AGC amplitude threshold 528, the signal amplitude is easily determined and readily comparable to the various analog thresholds in the analog domain. The one comparator 212 can be multiplexed between the onset analog reference 520, offset analog reference 524, Vref threshold 530, and AGC analog reference 528. As mention above, digital outputs are provided by the comparator 212 to the algorithm/control logic 216 to indicate the crossing of such amplitude thresholds.

The sampled signal amplitudes of the signal from AGC amplifier 206 are used by the $\Delta$V nulling amplifier 208 and ADC 214 to generate $\Delta$V values of a desired bit size, for example, a 7 bit or 8 bit $\Delta$V value. Configuring the amplifier prior to the ADC 214 and nulling the present amplitude sample value with the previous sample amplitude value allows for digitally converting a change in voltage (i.e. slope) to $\Delta$V's. The nulling amplifier 208 has a gain, for example, of 16, to restore amplitude to the differenced value. The ADC 214 sampling period is synchronized (non-overlapping) to the stimulus to avoid degrading the ADC sensitivity with stimulus circuitry noise. The stimulator frequencies of the IPG 55 may be, for example, and thus the sampling frequencies may be, for example, 20, 30, 33, and 40 Hz. One skilled in the art will readily recognize that the ADC 214 and ΔV nulling and amplification block 208 could be switched, with the ADC 214 digitally converting the sampled amplitude to a digital value and the digital values from the present sample and previous sample used to determine a digital ΔV value.

The ΔV values represent the change in amplitude over the sampling period. Several consecutive ΔV values can be evaluated to confirm the sustained slope characteristic of inspiration onset or offset as described further below with reference to the detection algorithm. By using several, for example, two or more, consecutive ΔV samples, short duration (higher frequency) noise or cardiac artifacts can be rejected and thus misdetection of a valid onset or offset is avoided. The tradeoff for considering more than one sample is that delay is added by waiting to use multiple samples for detection of an onset or offset.

As an alternative to using digital ΔVs for representation of slope of the respiratory waveform to the detection algorithm 216, an analog differentiator and peak detector could be utilized for slope measurement. However, the availability of the ΔV's in the digital domain allows for precise threshold settings and variation in bandwidth by choosing the number of samples to evaluate.

Figure 12B:
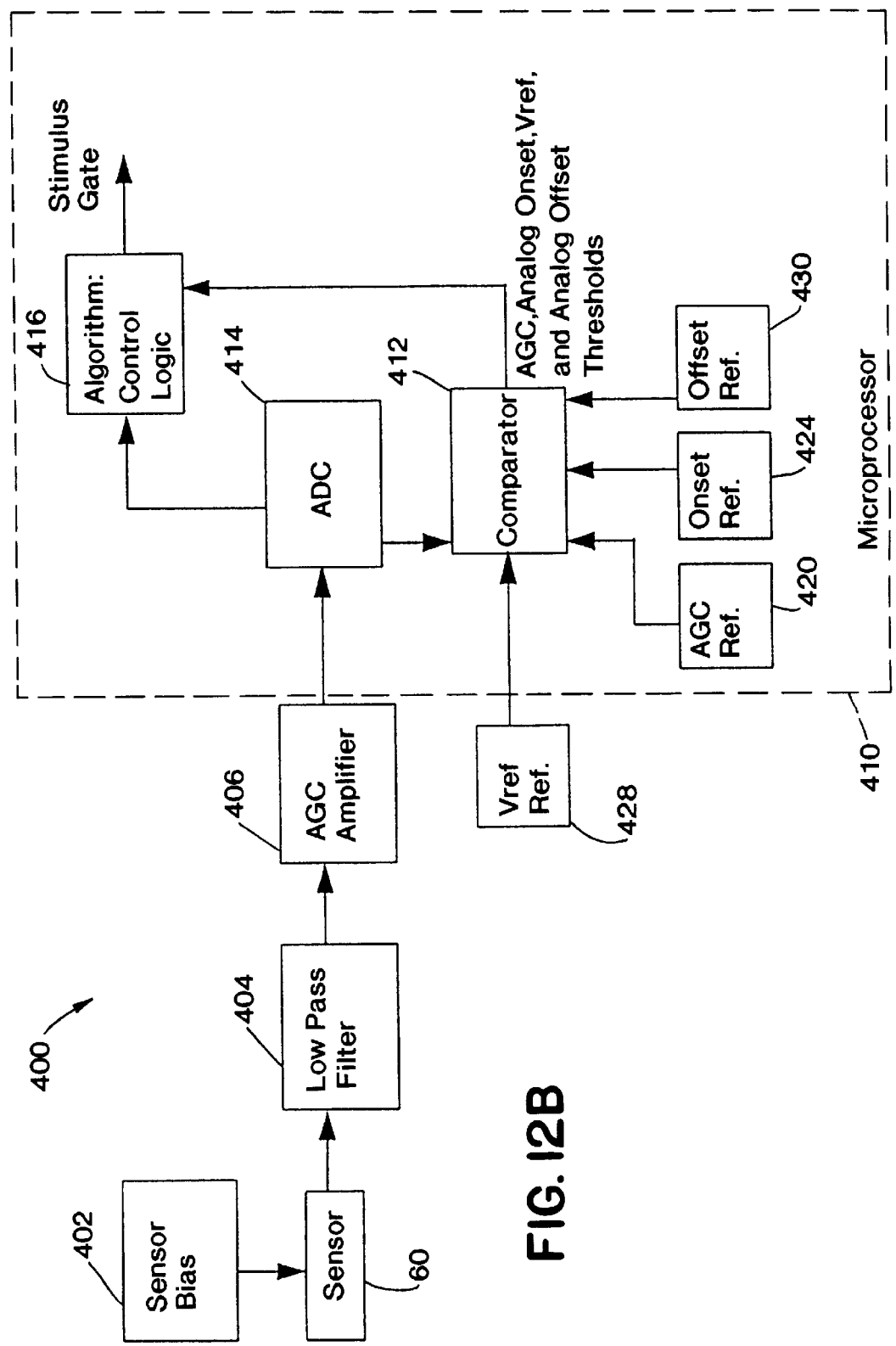
FIG. 12b is a second embodiment of a block diagram of the signal processing circuitry of the IPG/stimulator shown in block form in FIG. 6, implemented with a microprocessor, for receiving the respiratory effort signal from the sensor and providing an inspiration synchronized stimulation signal to the electrode in accordance with the present invention.

A second embodiment of signal processing circuitry 400 for performing the signal processing with substantially equivalent results to signal processing circuitry 200 is shown in FIG. 12b. The sensor input circuitry, including the sensor bias 402, low pass filter 404, and AGC amplifier 406, is substantially the same as previously described with respect to the first embodiment. However, the monitoring circuitry 203, as indicated by the dashed line in FIG. 12a, is performed with the use of a microprocessor 410 and associated code. The microprocessor 400 includes an internal analog to digital convertor (ADC) 414 which presents a converted sampled amplitude to the algorithm/control logic 416 and comparator 412, i.e. the logic and comparison are implemented in software. In this embodiment, ΔV's are still determined based on the sampled signal from the AGC amplifier representative of slope of the respiratory effort waveform, and sampled amplitude comparisons are still made with the various thresholds. However, the sampled amplitude of the respiratory effort signal is immediately converted to the digital domain by the ADC 414 and processed digitally by the algorithm to obtain the ΔV's. Further, the digitally converted sampled amplitude is digitally compared to digital thresholds 420, 424, 430, and 428 as necessary to carry out the functions as described further below. The algorithm 416 then processes the ΔV, i.e. slope, information which it generated, and the amplitude comparison information generated by digital comparison 412, as described further below. Also as described further below, the processor 400 can be powered down at certain times when it is not required; conserving energy. Although both the first and second embodiment may be utilized in accordance with the present invention, along with various other configurations of digital or analog circuits, whether with the use of a processor or without, the remainder of the description shall be made with reference to FIG. 12a for simplification, except as otherwise noted and for specific features which are particularly beneficial to the processor based configuration, such as processor power down.

The detection algorithm as shown in the flow diagrams of FIGS. 13a–13h shall now be described with reference thereto and with reference to other figures herein as required. The detection algorithm or algorithm logic 216 as shown in FIG. 12a resides in the IPG 55 of the implantable system 50 shown in FIG. 5. The detection algorithm 216 detects inspiration onset and offset using comparisons of sampled amplitude to multiple thresholds and ΔV values representative of the slope of the respiratory effort signal. As described previously with reference to FIG. 12a, in the first embodiment, the digital outputs used by detection algorithm 216 to track the respiratory effort waveform, are the onset and offset amplitude threshold comparison outputs from the analog comparator 212 and the digital ΔV slope value output from the ADC 214 (FIG. 12a). With respect to the second embodiment utilizing the microprocessor and associated code, the digital comparison of the digitally converted sampled amplitude to the various digital thresholds along with the ΔV values generated using the digitally converted sampled amplitude, all generated inside the microprocessor, are utilized by the processor control logic algorithm 416. This respiratory effort signal information concerning amplitude and slope and the knowledge of respiratory timing parameters during sleep are used by the algorithm to reject cardiac and motion artifacts and control stimulus of muscle in the treatment of sleep apnea.

Figure 13A:
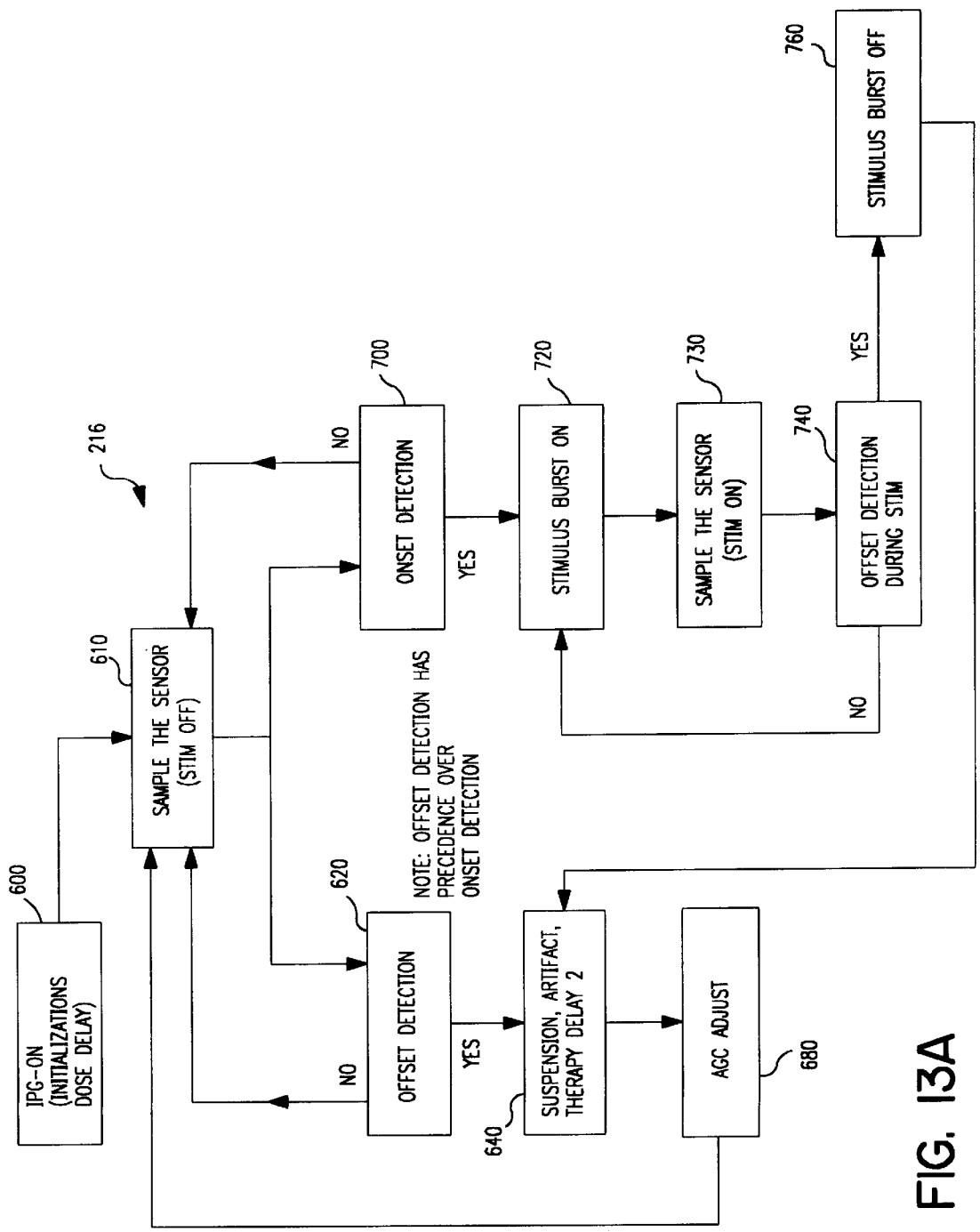
FIG. 13a is a top level flow diagram of the algorithm/control logic shown in block form in FIG. 12a and 12b in accordance with the present invention.

A top level flow diagram of the detection algorithm/control logic 216 is shown in FIG. 13a. Generally, the detection algorithm is initiated at IPG-ON (block 600). The sensor signal is then sampled (block 610) at a programmed sample rate and the appropriate outputs (i.e. ΔV's and analog threshold outputs) are generated by the associated components of the system. Offset detection (block 620) and onset detection (block 700) are then performed, with offset detection taking precedence over onset detection. If neither offset nor onset is detected then the sensor signal is further sampled and offset and onset detection repeated. If offset is detected, then various functions are performed such as determining whether suspension mode is to be entered, therapy delayed, or AGC updated (blocks 640, 680). If onset is detected (block 700), then stimulation is initiated (block 720). The stimulation is continued and the sensor sampled during stimulation (blocks 730) until an offset is detected (block 740) and stimulation is terminated (block 760). The various functions performed after an offset is detected (blocks 640, 680) are then performed.

The IPG ON command block 600 is a patient or physician controlled function, where he/she turns the IPG "ON" via the patient programmer 70 or physician programmer 80. The IPG 55 recognizes the IPG ON command (block 602) and begins a start-up sequence including dose control timer (block 603), a dose delay (block 604), a setting of initial conditions 606, and the entrance of suspension mode until a regular breathing pattern is recognized. The IPG ON command may also initiate a patient self stimulation test and/or a diagnostic self test, as described further below.

Dose control timer (block 603) is immediately started by the on command, i.e., IPG-ON state. Dose is considered the treatment time over which the IPG 55 is on and stimulation synchronous with inspiration can occur as the patient sleeps. A patient typically uses the system 50 during a regular night's sleep. A patient may sleep anywhere from, for example, 1 to 15 hours. The dose period is initiated by the patient programmer 70 or a physician programmer 80 transmitting an IPG-ON command to the IPG. Dose is terminated or dose timer timeout occurs by either reaching a maximum programmed dose time or the patient programmer 70 transmits an IPG-OFF command, i.e. IPG-OFF state. The dose time-out provides an automated method for turning off stimulation in the morning after a night's sleep. The maximum dose time is physician programmable and may be for example, from 1 hour to 15 hours in 1 hour increments.

The initial IPG-ON command also initiates the dose delay period (block 604). The delay waits a sufficient amount of time before starting stimulation to allow the patient time to fall asleep. Dose delay 604 is physician programmable from, for example, 0 to 75 minutes, in 5 minute increments. If stimulation were to start too soon, the patient may be disturbed and may have difficulty sleeping. The detection algorithm does not operate during dose delay 604 and minimal battery power is consumed during this delay period, for example, in a microprocessor based design, the microprocessor could be powered down.

At the end of the dose delay (block 604), the detection algorithm parameters are initialized (or reset). The initial conditions include: Onset Count=0, Offset Count=0, Artifact Count=0, Average Respiratory Period Weighted Sum (TWS) =1 second, Max Stimulation On Timer=OFF. In addition, the start AGC watchdog timeout timer as described further below is initialized to 1 second and AGC gain is initialized to a mid-gain setting as described further below. After initialization of the conditions (block 606), as indicated above, stimulus is indefinitely suspended, i.e. suspension mode is entered, until a regular breathing pattern is recognized (block 608).

Generally as will be explained further below, in suspension mode, stimulation is disabled in the presence of artifacts or non-periodic respiration. Suspension is defined as a state where stimulation is suspended due to the lack of a stable respiratory pattern. If the present measured respiratory period (T) is not within a specified minimum and maximum time or if it is not relatively equivalent, i.e. within a certain tolerance (Tvar) of, a stored weighted sum respiratory period (TWS), then stimulus is suspended or suspension mode is entered. The detection algorithm does not exit suspension mode until a measured respiratory period (T) is within the allowed variability from the weighted sum respiratory period (TWS).

As shown in FIG. 13a, during the sampling of the sensor 60 (block 610), the detection algorithm looks for a valid onset so that stimulation can be initiated (block 720). The onset of inspiration is characterized as a sustained increase in slope greater than a physician programmable ΔV onset threshold value and an amplitude greater than a physician programmable analog onset threshold as shown in FIG. 14. An offset detection takes precedence over onset detection, as reflected by Offset Latched & Analog Vref block 622 (FIG. 13c).

Figure 13B:
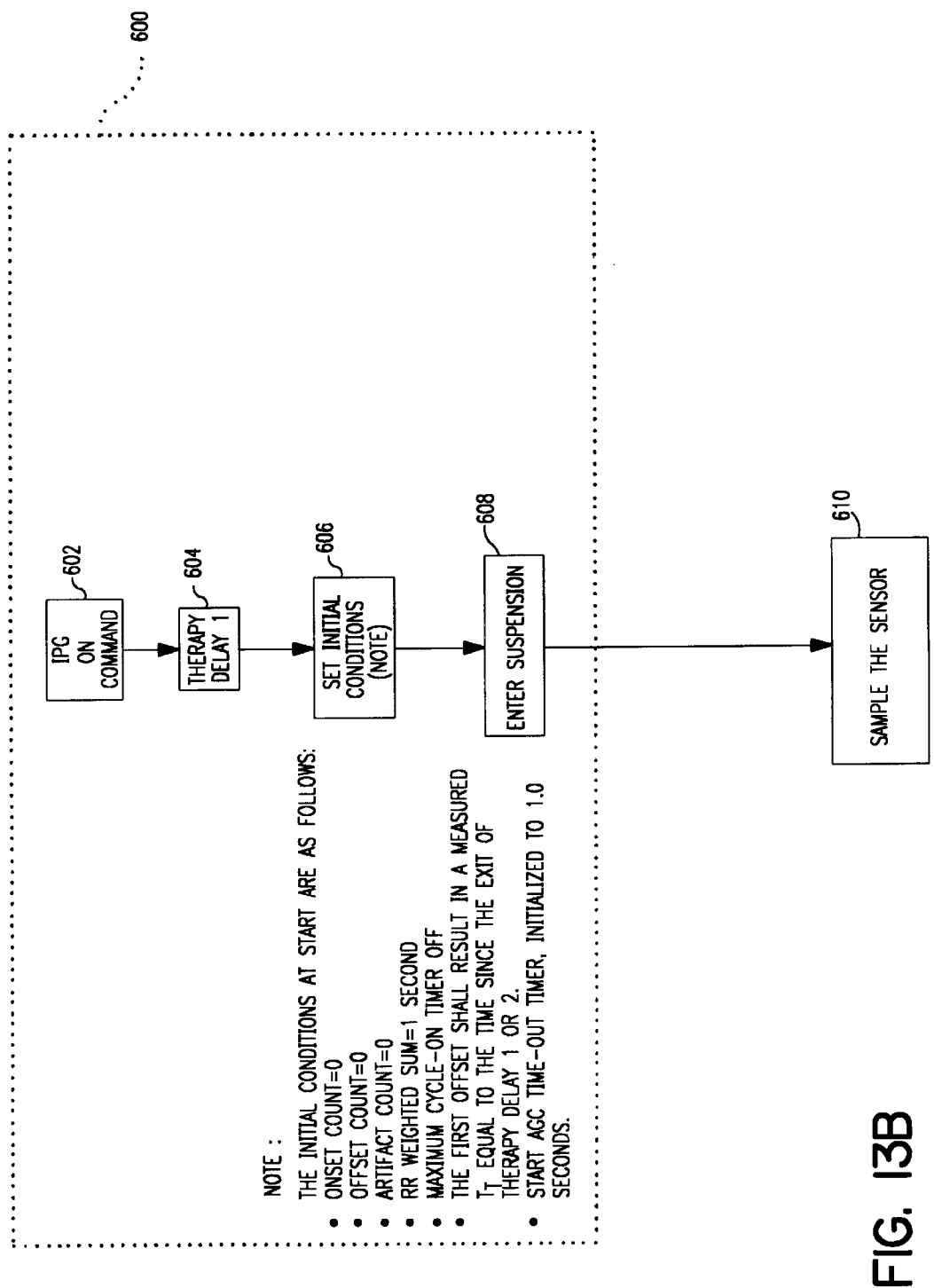
Figure 13C:
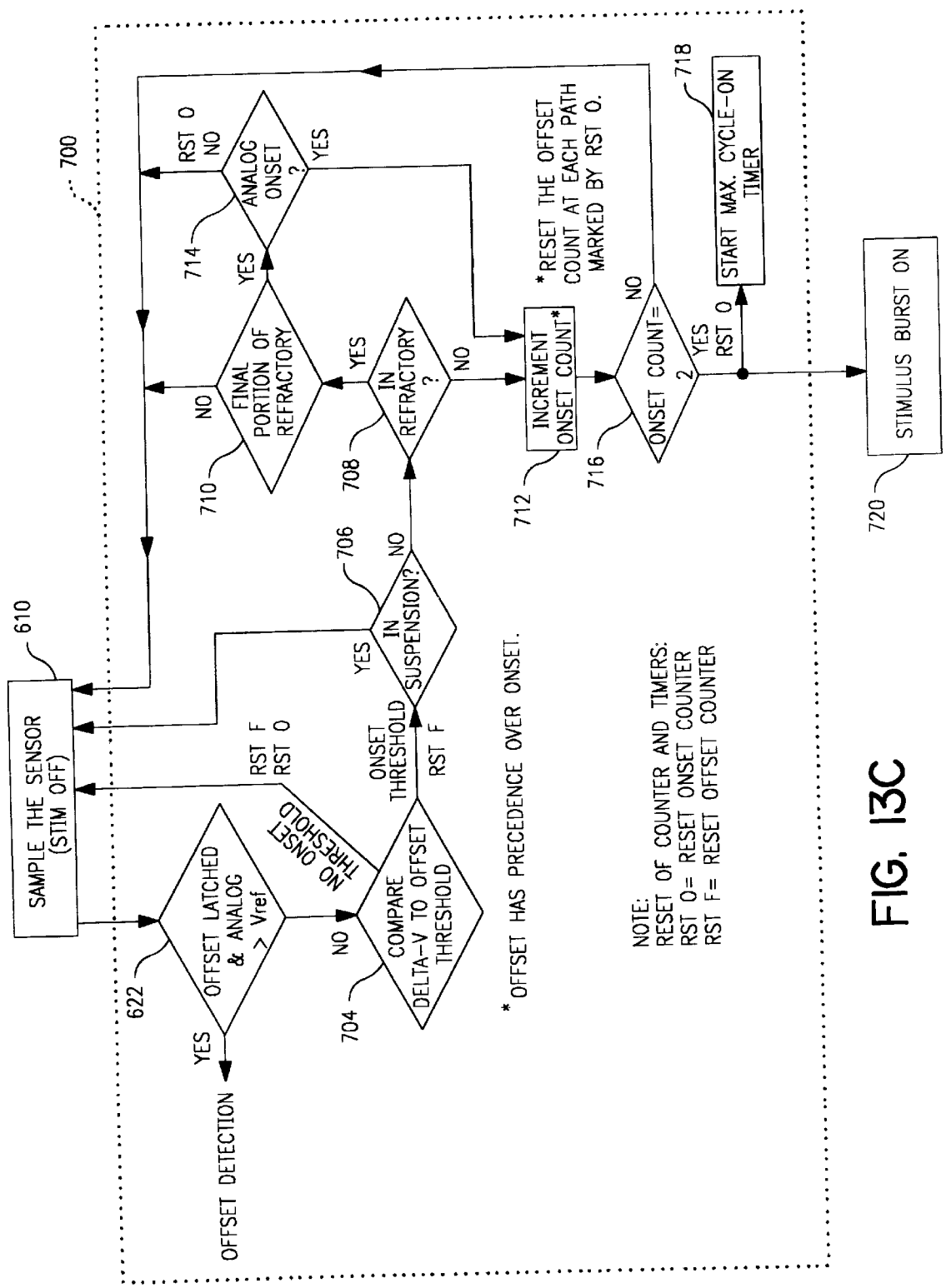

As shown in block 700 of FIG. 13c, two consecutive ΔV's greater than the physician programmed ΔV onset threshold value are required to indicate a sustained increase in slope. The comparison of sampled ΔV's to the ΔV onset threshold is shown as block 704. The time required to obtain the two samples, for example, may be between 40 ms and 80 ms, depending on the sampling rate; the stimulus rate and sampling rate being the same. The stimulus rate is programmed or fixed by the physician and the ΔV onset threshold can be adjusted at the same time to compensate for shorter or longer sampling rates. For example, a faster stimulus/sampling rate would result in smaller ΔV's since less change is seen over the shorter sampling period. Thus, a lower ΔV onset threshold may be appropriate.

As shown in block 704, if a ΔV does not exceed the ΔV onset threshold, the onset counter for counting the number of times the ΔV onset threshold is exceeded is reset. If the ΔV onset threshold is exceeded, it is determined whether the stimulation has been suspended (block 706). Although a valid ΔV onset threshold level was detected, if the IPG 55 is in suspension mode, the onset counter is not incremented. Further sampling and comparisons are then performed to detect offsets. The offsets are detected to determine if a stable respiratory signal is present. If the IPG is not in suspension mode then it is checked to see whether the IPG is in refractory, i.e., a period of time between offset declaration and onset as described further below. Refractory (R), as shown in FIG. 14, includes both a hard refractory (HR) and a soft refractory (SR), i.e. a final portion of refractory (R). Refractory (R) is a processed time, based on a preprogrammed percentage of measured patient respiratory periods (T), during which time the patient is typically denied access to stimulation, except possibly in soft refractory.

As shown in block 708, if the IPG is in refractory (R), then it is checked to see whether it is in hard refractory (HR) or soft refractory (SR) (block 710). If the IPG 55 is in hard refractory (HR), the onset counter is not incremented and more ΔV comparisons are made. If the respiratory effort signal is in soft refractory (SR), then the amplitude of the signal is compared to the programmed analog amplitude onset threshold (block 714). If the signal does not exceed the analog onset threshold, the onset counter is not incremented but rather reset to zero and sampling is continued. If the signal exceeds the analog onset threshold, then the onset counter is incremented (block 716). Also as shown by blocks 708 and 712, if the ΔV onset threshold is exceeded and the IPG is not in the refractory period, then the onset counter is also incremented (block 712). If the onset counter is equal to a count of two, a valid onset is declared (block 716), the counter is reset to zero, a stimulation timer is initiated for controlling the maximum stimulation length (block 718) as described further below, and stimulation is initiated (block 720).

The illustrative 200 ms onset previously described is obtainable, particularly by adjusting the programmable ΔV and analog amplitude onset thresholds along with refractory (R) and soft refractory (SR) discussed further below. By such adjustment, the algorithm can be made to be 'trigger happy' or predictive such that onset detection is not late and the refractory (R) is maximized to save battery life. For example, with use of the soft refractory period, the analog threshold may be set lower to allow a lower signal to exceed the threshold and increment the onset counter. This still, however, blocks motion artifacts from being detected as an onset is detected only if both slope and amplitude thresholds are exceeded during soft refractory, as opposed to just slope out of refractory (R).

Generally, to declare an onset and thus start stimulation, in addition to the ΔV onset threshold being exceeded by two consecutive samples, the algorithm must be out of refractory (R) during the two consecutive ΔV samples above threshold or the pressure signal amplitude must be greater than the analog amplitude onset threshold and the algorithm must be in soft refractory (SR). Further, the algorithm must be out of dose delay, therapy delay, and suspension for stimulation to occur.

It should be apparent to one skilled in the art, that variations of onset detection may provide suitable detection. For example, the number of counts may vary, the sampling rate may vary, more ΔV values may be used alone to detect onset in soft refractory as opposed to the use of both ΔV and amplitude information in soft refractory and other variation as would be readily apparent to one skilled in the art.

During stimulation, the sensor signal is still being sampled (block 730). Offset detection (block 740) is being performed using the sampled signal during stimulation (block 740). If an offset is detected and latched while stimulation is on, stimulation is terminated (block 760) when the latched offset is validated or declared a valid offset. If offset is not detected, stimulation proceeds until a maximum stimulation period is reached as timed by max-stimulation on timer (block 718), at which time an offset is automatically declared.

Therefore, maximum stimulation time is used in the event that an offset of the inspiratory phase is not detected. A maximum stimulation time shall terminate the stimulation and algorithm functions which typically occur at a regularly detected and validated offset are initiated. In other words, if maximum stimulation time is reached, an offset is declared and functions such as calculating weighted sum, starting refractory, etc. are initiated. When an offset is detected and latched (block 740) and stimulation is terminated (block 760) after the latched offset is validated, the algorithm proceeds to suspension, artifact, therapy delay block 640 as will be described further below.

The detection and declaration of an offset during stimulation (block 740) and when stimulation is off (block 620) shall be described together, as the flow of both blocks is substantially similar with the exceptions as noted. Such description shall be set forth with reference to FIGS. 13*d* and 13*e*.

Inspiration offset is the most reliable and repeatable signal characteristic to detect as the respiratory waveform slope changes from a positive slope to a sharp negative slope and the amplitude of the respiratory waveform signal reaches a peak value which is controlled by the AGC, for example, the 1.2 volts. Therefore, detection algorithm operation and timing is centered around the detection of offsets, although other periodic events in the respiratory signal may also be used.

Respiration timing, AGC control, and the accuracy, for example, of the prediction of the next onset are all dependent on offset detection. Generally, the detection of offset requires three consecutive $\Delta V$ samples below the physician programmed $\Delta V$ offset threshold 526 (FIG. 14) and the first of the three $\Delta V$ samples is required to have an amplitude greater than the analog amplitude offset threshold 524 (FIG. 14). Once these requirements are achieved, an offset is detected and latched. The algorithm then waits for the respiratory effort signal level to fall below the Vref or zero crossing threshold 530 before validating the latched offset, i.e. declaring a valid offset and terminating stimulation. Waiting for the signal to fall below the Vref threshold 530 discriminates against cardiac artifacts riding on the signal, which may cause another offset to be prematurely detected. Alternatively, the offset could also be validated at any amplitude after the offset requirements are met, such as for example, onset threshold or even immediately upon latching the offset.

Figure 13D:
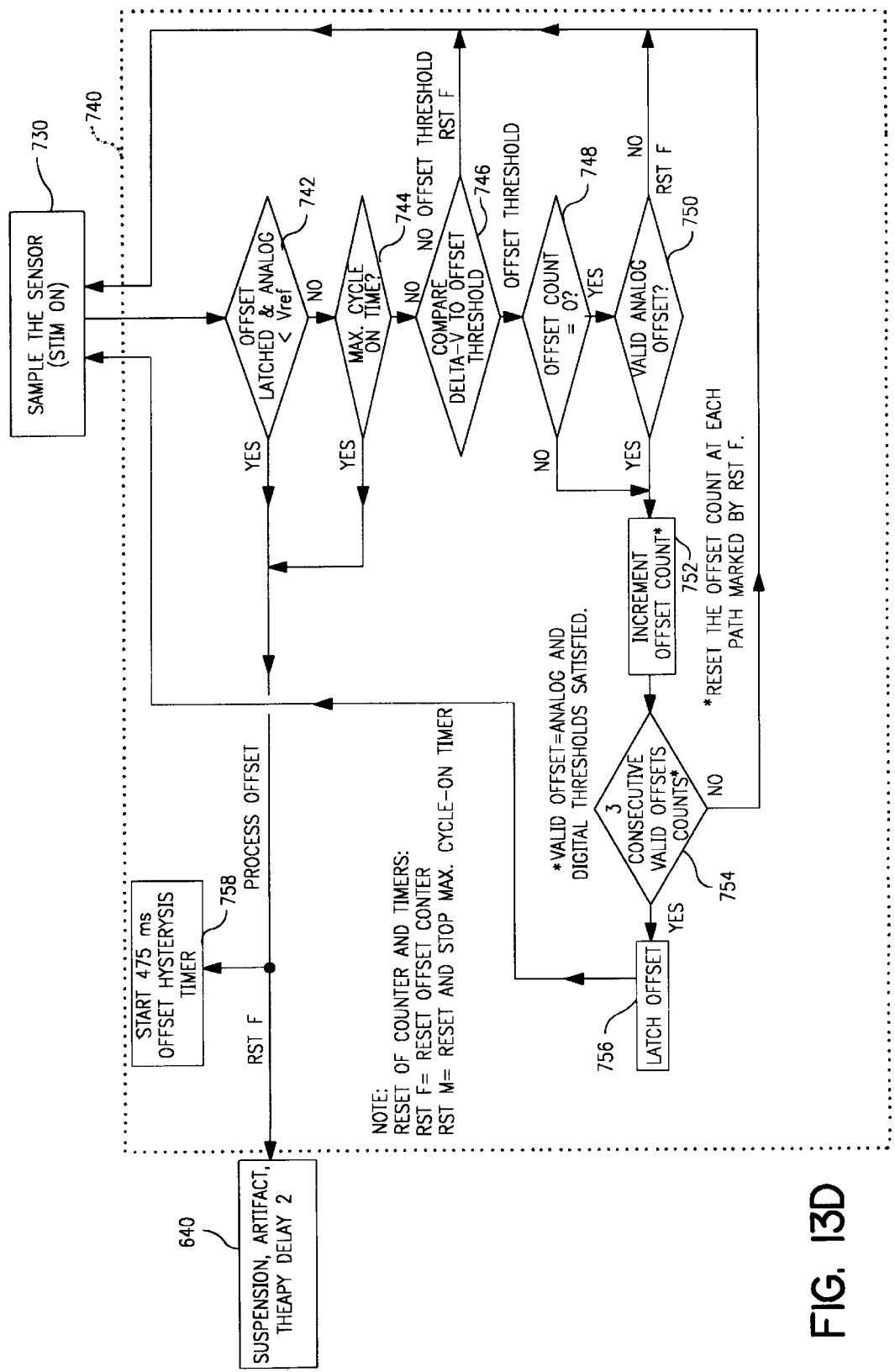
Figure 13E:
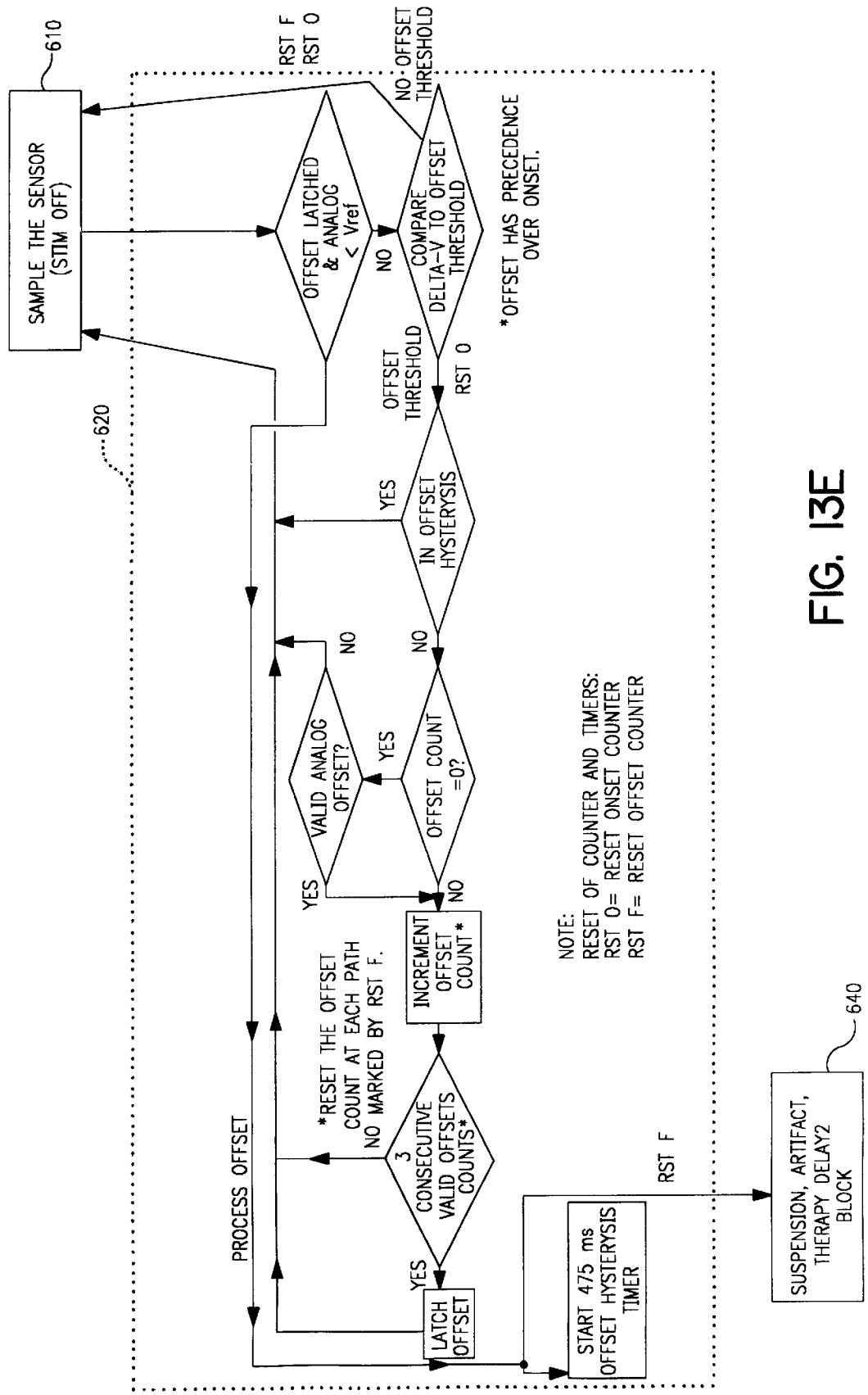
FIG. 13e is a flow diagram of the Offset Detection block of the flow diagram of FIG. 13a when stimulation is not occurring.

With reference to the flow diagram of FIG. 13*d*, as the sensor signal is sampled during stimulation (block 730), if an offset has not been declared or validated (block 742) and the maximum stimulation on time for stimulation has not been reached (block 744), a comparison of $\Delta V$ samples to the programmed $\Delta V$ offset threshold 526 is performed (block 746). If the programmed $\Delta V$ offset threshold is not met, then the algorithm resets the offset counter to zero and sample and comparison continues. If the programmed $\Delta V$ offset threshold is met, then the state of the offset counter is queried (block 748). If the offset count is at zero and the analog respiratory effort signal is not greater than the analog offset threshold to produce a first offset count (block 750), then the offset counter is reset to zero, the offset counter is not incremented and sampling and comparison is continued to detect an offset. If the offset count is equal to zero and the analog respiratory signal is greater than the analog offset threshold, then a first count is made (block 752). If the offset count is not equal to zero (i.e., a first offset count has been made), then such consecutive $\Delta V$ samples that meet the $\Delta V$ offset threshold increment the offset counter (block 752). If the counter registers three consecutive counts during three consecutive sample periods (block 754) with the first offset crossing the analog offset threshold 524, an offset is detected and latched. Once the amplitude falls below Vref (block 742) the latched offset is validated and stimulus is terminated. If the three consecutive offset count requirement is not met, then the offset counter is reset, and sampling and comparison is continued for detecting offsets.

The offset declared or validated is then processed further by Suspension, Artifact, Therapy Delay block 640 and an offset hysteresis timer is started (block 758). Offset hysteresis is utilized to prevent artifacts from declaring two offsets in a very short period of time. For example, if the offset slope was too shallow, multiple offsets could be triggered by artifacts in the signal waveform (e.g., if 6 consecutive $\Delta V$'s satisfied the $\Delta V$ offset threshold and the analog offset threshold was met for at least the first of each set of three, then two offsets could be declared). Therefore, offset hysteresis provides a blanking period, for example, about 475 ms, after an offset has been declared during which no other offset can be declared. The blanking period is to provide a form of hysteresis such that the algorithm will only 'see' one offset per respiratory cycle. The offset hysteresis should be sufficiently short to resume the detection of possible artifact signals for proper suspension mode and artifact counting operation.

Various alternatives to the offset detection portion of the algorithm can be made. For example, the number of counts necessary for an offset to be detected may be modified, the analog threshold may be required to be satisfied for all three $\Delta V$ samples as opposed to just one, the sampling rate may be different, different levels of analog thresholds may be used for declaration or validation of an offset to terminate stimulus and any other variation may be made that would be apparent to one skilled in the art.

The offset detection when stimulation is off (block 620) is substantially the same as described above with the exception that maximum stimulation on time does not need to be checked (block 744) as stimulation is off.

As mentioned previously, the detection algorithm/control logic 216 uses at least two ideologies including that the respiratory period (T) of respiration is known to be stable and consistent during sleep and that the ratio of the time of inspiration (TI) to the respiratory period (T) is typically known or can be evaluated with statistical measures. The detection algorithm 216 uses at least these two ideologies and also respiratory timing statistics of sleeping humans to make the algorithm robust and exclusionary of misdetecting artifacts for onset and offset. As part of implementing the ideologies, the weighted sum respiratory period (TWS) is used to build a running average of measured patient respiration periods (T) and is utilized in connection with various algorithm functions to control stimulation and reject artifacts. The various functions which employ the use of TWS include refractory (R)/soft refractory (SR) function, suspension function, AGC control, and the artifact counter function. After a general discussion of the these functions, the suspension function, AGC control and artifact counter function will be described further with reference to the flow diagram of FIG. 13f and 13g. The use of refractory (R)/soft refractory (SR) function has been previously described with reference to the flow diagram for onset detection (FIG. 13c).

The detection algorithm 216 evaluates the equivalence of every patient respiration period (T) by comparison of measured periods (T) to the continuously calculated weighted sum respiratory period (TWS) and to bounds for a respiratory period to evaluate whether respiration is stable. The detection algorithm having knowledge of the weighted sum respiratory period (TWS) and a substantially constant inspiration time (TI), also approximates the time between each offset and onset such that onsets can be predicted.

The geometric-series weighted sum used to generate the weighted sum respiratory average (T) is weighted more heavily by the most current measured T periods. The algorithm adds the present weighted sum to the present T period and then divides by 2. The result is expressed in the following equation: T Weighted Sum (n)=[T Weighted Sum (n−1)+T Interval (n)] /2. The maximum number of T periods contained in one sum is ten, but the T periods beyond the fifth have an insignificant contribution to the sum. Not all measured T periods are utilized in determining TWS. The algorithm measures the patient respiratory period (T) at each offset. If T falls out of the predetermined bounds set for T, i.e. min and Tmax, for example, in the range of 1 second to 16 seconds, indicating nonperiodic respiration, then the algorithm will consider the T period invalid. The invalid T periods are not added to the weighted sum (TWS).

With the weighted sum average respiratory period (TWS) calculated, the refractory period (R) can be approximated as described below. Onsets (and thus stimulation) can be kept from occurring for a period of time in the refractory period (R) following the declaration of offset of inspiration. This time frame is in the expiration phase of respiration. Any physiologic or sensor disturbances (artifacts, noise, etc.) during this time period can be rejected as onsets. Stimulation is thus inhibited during at least a portion of refractory (R), but sampling continues in order to detect the presence of artifacts and enter suspension mode, if necessary.

The refractory period (R) begins at the offset of inspiration (i.e. the end of stimulus) and continues almost until when the next inspiration onset is expected. A percentage of the weighted sum (TWS) is used to calculate the refractory (R) duration. For example, with TI/T ranges known from, for example, statistical analysis, the expiration portion of respiration and thus the refractory period (R) can be calculated as a fraction of the weighted sum (TWS). For example, the calculated refractory period (R) may be implemented based on the weighted sum by multiplying a physician programmable refractory multiplier of 0.375, 0.50, 62.5, or 0.75 times the weighted sum: refractory (R)=(Refractory Multiplier×Respiratory Period Weighted Sum (TWS)). Such particular refractory multipliers are for illustration only and any portion of T may be designated as refractory, such as from 0.1 to 0.75, particularly depending upon the individual patient's respiratory cycle.

The weighted sum respiratory period (TWS) is initialized upon the on command for the IPG 55 to be 1 second. The algorithm remains in suspension mode as described further below until the TWS is equivalent to the present measured T, i.e. periodic respiration is determined. The algorithm does not use refractory (R) to blank onsets until suspension mode is exited. This insures that the weighted sum (TWS) will have established a valid value and thus the refractory (R) will also be a valid duration for predicting onsets and blanking artifacts.

Refractory (R) is limited to a minimum time. This is achieved by only updating the weighted sum (TWS) for T periods greater than 1 second and therefore the weighted sum (TWS) has a minimum of 1 second. As such the refractory (R) minimum time is given by: Minimum Refractory=(Refractory Multiplier×1 second). The establishment of a minimum refractory time is a safety guard against over stimulation by establishing some minimum of blanking time.

Soft refractory (SR) is implemented in the final portion of the refractory period (R). The other portion of refractory (R) is referred to as hard refractory (HR) and is shown in FIG. 14. In hard refractory (HR), stimulation is not allowed, i.e. onsets are not responded to. In the soft refractory (SR) period of refractory (R), as shown in FIG. 14, an onset (i.e. stimulation) is allowed if the analog onset threshold and the ΔV comparison as described with reference to FIG. 13c both indicate an onset. The soft refractory (SR) portion of refractory period (R) may be a sum (TWS). Therefore, for 12.5% of the weighted sum (TWS). Therefore, for illustration, if refractory (R) is 75% of the weighted sum, then the soft refractory (SR) is during the 62.5% to 75% portion of refractory (R).

Alternatively, the soft refractory (SR) could be a function or percentage of refractory (R). Further, the refractory functions may be based on stimulus duration as opposed to respiratory rate. With this alternative, the algorithm would measure the duration of the previous stimulus interval and multiply the interval by a predetermined value. A further alternative for refractory could be based on both stimulus duration and the respiratory period (T) or any other alternative respiratory timing parameter that would be suitable for defining a refractory, hard refractory, and/or soft refractory period following offset detection, such as TI.

Suspension mode, which also utilizes TWS, provides several benefits. For example, the suspension function keeps the patient from being overly stimulated, i.e. patient comfort. Further, this technique also conserves energy to increase battery life. In suspension mode, stimulation is disabled in the presence of artifacts or non-periodic respiration. Suspension is defined as a state where stimulation is suspended due to the lack of a stable respiratory pattern. If the present measured patient respiratory period (T) is not within a specified minimum and maximum time or if it is not relatively equivalent to, i.e. within an allowed variability of, a stored weighted sum respiratory period (TWS), then stimulus is suspended, i.e. suspension mode is entered. The detection algorithm does not exit suspension mode until a measured patient respiratory period (T) is within the allowed variability from the weighted sum respiratory period (TWS) . The programmable values of allowed T variability (hereafter referred to as Tvar) may be for example, 25%, 33%, 50%, and infinite. Each and every offset is considered as a measure of the respiratory period (T) and/or the presence of artifacts. While in suspension mode, the algorithm continues all other signal processing tasks such as threshold comparisons, AGC adjustments, and weighted sum calculations.

Generally, suspension is entered by the algorithm under the following conditions indicative of nonperiodic respiration. First, upon initialization of the IPG 55, the algorithm is in the suspension state, as shown in FIG. 13b, block 608, after the IPG 55 is turned ON and dose delay (block 604) is completed. Second, if the presently measured respiratory period (T) is less than the minimum or greater than the maximum bounds programmed for T, suspension mode is entered, i.e. the bounds of 1 second and 16 seconds as previously mentioned. Third, if the present respiratory period (T) is not within a programmed allowed variability, i.e. Tvar, suspension mode is entered. And last, suspension is entered after the completion of a therapy delay initiated with use of the artifact counter as described below. It should be readily apparent to one skilled in the art that the number of respiratory violations of, for example, Tmin, Tmax or Tvar, which are required for suspension mode to be entered may vary. For example, more than one violation may be required to enter suspension.

The above described suspension mode technique disables stimulus in the presence of physiologic artifacts such as arm movements and head movements. Such movements occur only when the patient is in shallow sleep or awake. An example of the benefit of suspension mode is the case of a sleeping patient awakening to a phone call. Suspension mode will be entered as the patient moves about and stimulation will be inhibited while the patient speaks on the phone. Suspension mode is also intended to disable stimulus in the presence of non-physiologic and environmental noise sources. During suspension mode, the algorithm continues to evaluate the signal and will exit suspension mode and return to stimulus as soon as a periodic respiratory signal is re-established. established. Therefore, only the prevention of stimulus conserves energy as the sensor must still be operated.

As mentioned above, an artifact counter is used to initiate a therapy delay during which time stimulation is disabled. This is technique also conserves energy, lengthens battery life, and rejects artifacts. If the respiratory waveform continues to be too variable or multiple motion artifacts are occurring while in suspension mode, then the artifact counter will cause the algorithm to enter therapy delay. While in suspension mode, the number of offsets are counted by the artifact counter, in which case an offset is defined as the falling peak of either a respiratory or artifact event. If a maximum number of offsets are counted during suspension mode, then the algorithm enters a therapy delay period. The maximum artifact count is physician programmable, for example, to 10, 20, 40, or 80. During therapy delay, initiated by the artifact counter, the algorithm does not process the respiratory waveform signal and therefore, energy is conserved by turning the pressure sensor off and by preventing stimulation. Upon completion of the therapy delay period, the algorithm resets to an initial state (AGC gain and weighted sum reset, etc.) like when the IPG 55 was first turned on. Sampling the signal in the suspension mode is then resumed.

The counting of offsets during suspension mode is a simple method for determining the extent of non-respiratory activity. If frequent offsets are occurring, then this indicates that extensive movement exists and the algorithm shall transition quickly into therapy delay. If suspension mode occurs due to a short duration event, the offset artifact count will not reach the maximum, and stimulus will resume after the steady respiration rate has been re-established. If suspension mode is maintained by a variable respiratory rate, the offset artifact count will eventually lead to a maximum artifact count and therapy delay from counting of offsets. It should be noted that the artifact count is reset to zero upon exiting suspension mode.

The artifact counter function also provides the patient a method to quickly terminate stimulation without the use of the patient programmer 70. This is accomplished by tapping in the proximity of the pressure sensor to induce artifact counts. Such tapping allows the patient to terminate stimulus for the duration of therapy delay in the event that the patient programmer 70 is lost or fails during the night. Such termination could also be accomplished by use of a magnet being passed over a reedswitch built into the IPG 55.

Offset hysteresis, as previously described, is also used to conserve energy, as during this period of time the sensor can be shut down. Further, although some functions described herein may depend on the sensor functioning during refractory, with some modifications to the algorithm, the sensor may also be shut down during refractory, particularly hard refractory, as stimulation is prohibited. Thus, energy can also be conserved by shutting down the sensor whenever the respiratory waveform is not needed by the remainder of the system.

Figure 13F:
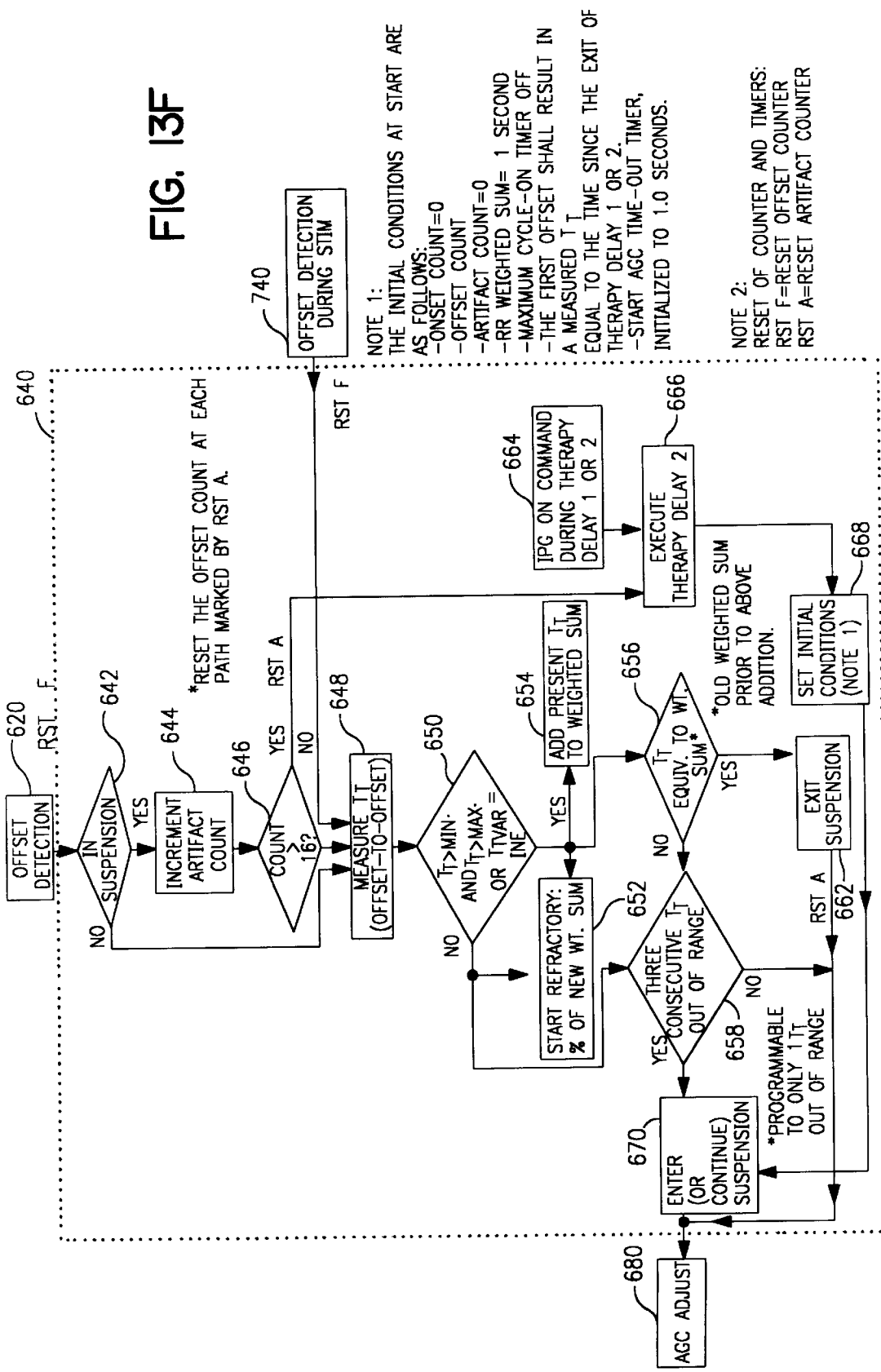

With reference to FIG. 13*f,* the flow of the suspension and artifact counting techniques in the detection algorithm shall be described. If offset is detected while stimulation is off (block 620), then it is determined whether the algorithm is in suspension as described above. If the unit is in suspension mode, artifacts (i.e. offsets, both inspiratory and artifact) are counted to determine if the algorithm should go into therapy delay (block 644). If the count exceeds some predetermined number, such as, for example, 16 counts, then the artifact counter is reset to zero, suspension mode is exited and activation of programmed therapy delay is entered (block 666). The therapy delay time is also started upon receiving the IPG on command during either an already occurring therapy delay (block 666) or dose delay (block 604) (FIG. 13*b*). After the therapy delay is exited, the initial conditions are set, substantially the same as when the IPG is turned on with the patient programmer (FIG. 13*b*).

If an offset has been detected either during stimulation or when stimulation is off, respiratory period (T) is measured (i.e. offset-to-offset or the time from the last offset to the current offset) (block 648). The current measured respiratory period (T) is then compared to Tmin and Tmax (block 650). If the current respiratory period (T) is not greater than Tmin and less than Tmax, then refractory (R) is started (block 652) based on a percentage of the previous weighted sum respiratory period (TWS). Further, if three consecutive current respiratory periods (T) measured do not meet these requirements, then the algorithm goes into suspension mode and stimulation is not allowed, otherwise, artifact counter is reset to zero and suspension mode is exited.

If the current respiratory period (T) is greater than Tmin and less than Tmax, then the current measured respiratory period (T) is added to the weighted sum average respiratory period and a weighted sum (TWS) of the previous breaths is calculated to determine a new average weighted sum respiratory period (block 654). Refractory is started (block 652) based on a percentage of the new average weighted sum, as updated. Further, the current respiratory period (T) measured is compared to the weighted sum from the previous offsets (i.e. the old weighted sum prior to the addition of the current T) (block 656). If the current T is equivalent, i.e. meets Tvar, indicating periodic respiration, then the artifact counter is reset to zero and suspension mode is exited. Otherwise, it is once again determined if three current respiratory periods (T) measured do not meet the Tmin, Tmax and Tvar requirements (block 658). As before, if three consecutive T's do not meet the Tmin, Tmax, and Tvar requirements, then the algorithm goes into the suspension mode or suspension mode is continued (block 670) and stimulation is not allowed, otherwise, artifact counter is reset to zero and suspension mode is exited (block 662).

The number of consecutive out of tolerance T's necessary to enter suspension mode is programmable. For example, the number can be set at one or other suitable values. Further, Tvar can be set to infinity which overrides the suspension feature and suspension is never entered.

In either case, whether suspension mode is entered or exited, the automatic gain control (AGC) is continually utilized or adjusted (block 680) as shall be described with reference to FIG. 13g. However AGC is not operational during treatment delays, i.e. dose delay or therapy delay, as the pressure sensor need not be operated during this delay time, conserving battery life. The AGC control described herein is applicable to the provision of any signal characteristic of a periodic physiological parameter for use in a therapy system. For example, the normalization provided by the AGC control is particularly applicable to systems which perform functions based on comparing the signal to the thresholds.

The AGC amplifier 206 (FIG. 12a), as described previously, is required to normalize the pressure sensor output to a consistent peak to peak signal, for example, 2.4 volt peak-to-peak signal. The operation of the AGC for the system 50 is dependent on the detection algorithm for synchronizing gain increment and decrements. The AGC consists of a plurality of gain steps, for example, 64 gains steps. Gain is incremented exponentially such that each gain step increases by the same percentage, for example, about 5.3%. However, gain may be performed by other than exponential techniques, such as, for example, techniques that produce equivalent increases as opposed to equivalent percentage increases.

Generally, the AGC functions in the following manner. The gain is incremented or decremented once per respiratory period (T). The AGC gain is changed immediately following detection of a periodic event in the waveform, i.e. a 'true' offset. True offset is defined here so as to indicate those offsets which are likely to be from an actual, stable inspiration offset and not a motion artifact or irregular breathing. The algorithm determines an offset is true if it does not occur during refractory (R) (including both soft refractory and hard refractory), as during refractory (R) it is assumed that the offset is an artifact offset. Offsets resulting in a respiratory period (T) outside of the predetermined bounds set for the periods, such as, for example, less than 1 second or greater than 16 seconds, are also considered invalid.

It is desirable to not change gain during refractory as the offsets which occur in this period may be of large amplitude, due to a motion artifact, and gain may be unnecessarily updated. Also, the refractory sets a limit on how fast the gain can be changed. Thus, if a rapid burst of artifacts occurs during refractory (R) then there will be no rapid change in gain. If a burst of artifacts occurs while the algorithm is not in refractory (R), then the first artifact will be considered an offset and subsequent artifacts will not change the gain as they will be in refractory (R). Thus, rapid offsets can only change the gain once during a respiratory cycle, i.e. increment or decrement once. AGC control is performed during suspension mode, along with offset detection and refractory, as only stimulus is inhibited and an exceeding of the artifact counter results in a therapy delay while in suspension mode.

An AGC watchdog timer also forms a part of AGC control. The AGC watchdog timer is reset each time a valid offset occurs resulting in the AGC gain being updated. The watchdog timer will otherwise time-out at, for example, 1.5 times the respiratory period weighted sum (TWS) or in other words, the watchdog timer time-outs at 50% beyond the point where an offset is expected. At time-out an AGC threshold is used to determine if the AGC gain should be incremented or decremented by one step. The watchdog timer will continue to time-out and increment or decrement until offsets begin occurring. The offsets then take control of the AGC operation. Therefore, the watchdog timer gets the gain to a level such that offsets can be detected and normal AGC control via offsets can be established, particularly when the IPG 55 is first turned on.

The AGC is initialized to a mid-range setting. If this initial gain is too low, the watchdog timer may have to cycle several times before offsets begin to occur and equilibrium is reached. The watchdog timer is loaded with a predetermined time, for example, 1 second at the initialization of the algorithm. Thus, the gain will increment one step per second until offsets are achieved, unless the initialized gain is too high, in which case each offset and/or the watchdog timer will decrement the gain until equilibrium is reached. The AGC is reset or reinitialized at each exit of therapy delay or dose delay.

Generally, therefore, gain is updated when an offset is detected following onset, even while in suspension mode or gain is updated when a watchdog time out occurs if an offset is not detected within a predetermined period of time. However, offsets detected while in refractory (R), whether or not in suspension mode, do not initiate gain update. Further, since offsets are not even looked for in dose delay or therapy delay, AGC is not updated during this time period. Typically, after initialization, the gain is incremented with use of the watchdog timer until valid offsets can be detected. Thereafter, the AGC typically controls the gain by toggling between increments and decrements to keep the gain at a particular level, i.e. the AGC threshold 528 (FIG. 14) and the waveform is normalized.

Figure 13G:
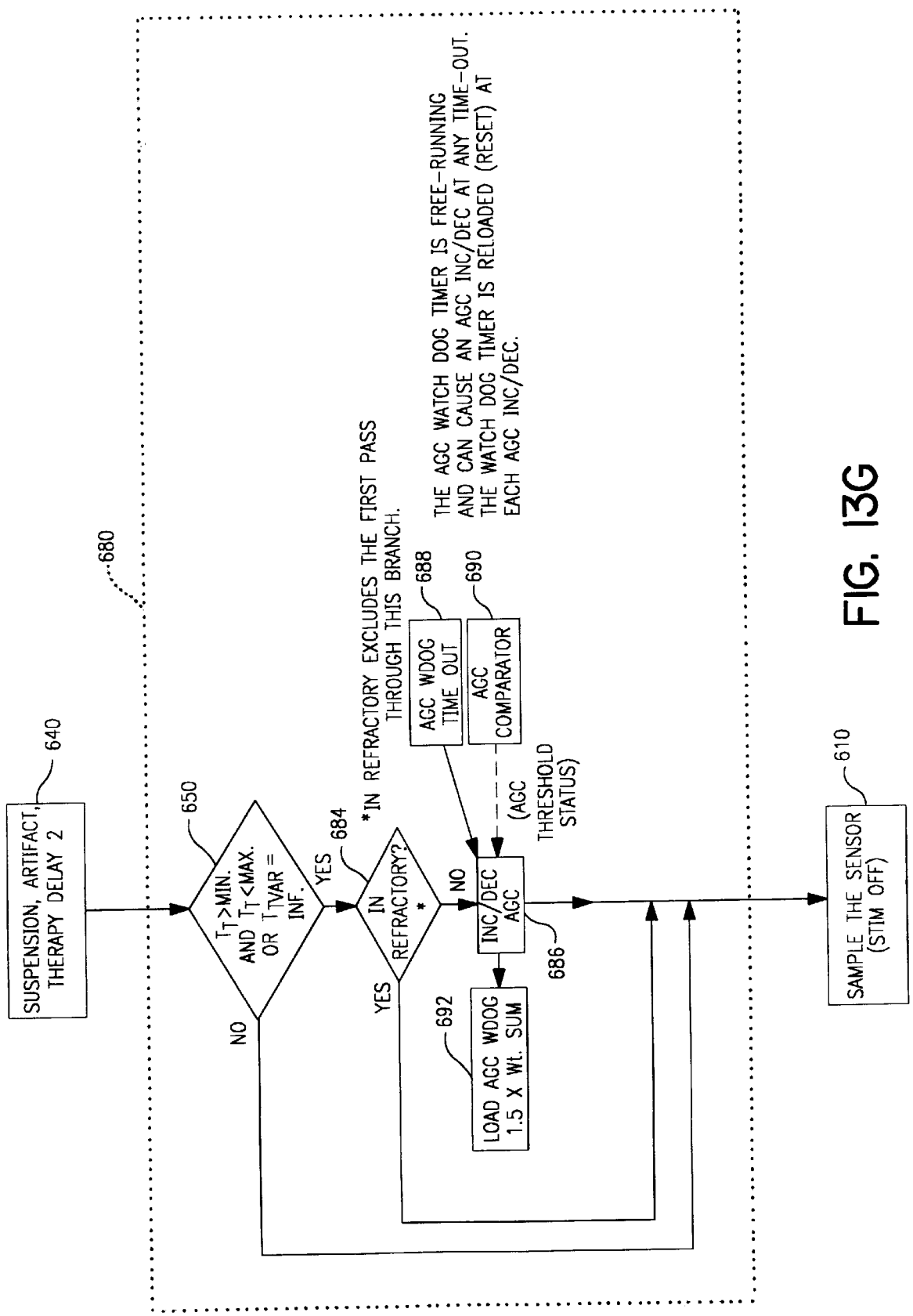

The flow of AGC control 680 is shown in FIG. 13g. AGC is run virtually simultaneously with the determination after an offset is detected of whether the algorithm should be in suspension or not as described previously with reference to FIG. 13f. As such, block 650 (FIGS. 13f and 13g) appears in both flow diagrams. AGC is not performed until the current measured respiratory period (T) meets the requirements of being greater than Tmin and less than Tmax (block 650), i.e. a somewhat stable periodic signal is sensed. Further, AGC update is performed if Tvar is set to infinity (block 650), regardless of the Tmin and Tmax requirements, i.e. if Tvar is set to infinity then all requirements for T are disabled for suspension and AGC functions. If the gain is not updated the sensor is continued to be sampled (block 610) and offset and onset detection is performed (blocks 620 and 700). If such requirements are met, then it is determined whether the algorithm is in refractory (R). If the algorithm is in refractory (R), then the gain is not updated (block 684). If the algorithm is not in refractory, then gain is either incremented or decremented based on a comparison with a predetermined AGC amplitude threshold (FIG. 14) (blocks 686 and 690). If the amplitude of the respiratory effort signal is less than the AGC threshold at any time since the previous update, then gain is incremented at, for example, offset, watchdog timeout or any other periodic event in the respiratory cycle. If the amplitude of the signal is greater than the threshold at any time since the previous update, then the gain is decremented at offset, watchdog timeout or any other defined periodic event in the cycle. The watch dog timer is reset at each and every AGC increment or decrement. However, at any time when no offsets are detected in a specified period of time, then the gain is incremented or decremented using the watchdog timer, i.e. a time based on the weighted sum respiratory period (block 692).

Generally, therefore, for a signal characteristic of a periodic physiological parameter, such as respiration, which include multiple periodic cycles, gain is updated when a periodic event is detected. The gain, however, is updated only once during a periodic cycle. Further, a watchdog timeout occurs if the periodic event is not detected and gain is updated even though a periodic event is not detected. Thus, the gain will be adjusted once per periodic cycle upon detection of a periodic event or at a watchdog timeout.

Other alternative methods of AGC implementation may be utilized with the present invention. For example, the AGC may adjust the amplifier gain after each amplitude sample has been taken. The magnitude of the sample would then be processed digitally to adjust the gain such that the amplifiers operate in mid-dynamic range. This technique has the advantage of quick gain adjustments and continuous digital knowledge of the signal amplitude. However, the AGC would not provide normalization and thus relative threshold measurements are not possible.

In general, the algorithm must be in the following state for stimulation to occur. A valid onset consisting of a certain number of ΔV's, for example, two ΔV's, above ΔV onset threshold must be detected. The refractory period (R) must be complete or the analog onset threshold must be crossed if the algorithm is in soft refractory (SR). The algorithm must not be in suspension mode and the algorithm must not be in either dose delay or therapy delay.

Further, any one of the following events will terminate stimulation: a predetermined consecutive number of ΔV's, for example, three consecutive ΔV's, below ΔV offset threshold with the first ΔV sample below the ΔV offset threshold satisfying the analog offset threshold (the offset must also be validated by comparison to another threshold level such as zero crossing); maximum stimulation time is reached; a patient initiates therapy delay by giving another IPG on command when treatment is on; end of the dose timer period after a night's sleep; and an IPG-OFF command.

Moreover, in general, implantable stimulation system 50, operates in the following manner. At some point following the IPG 55 implant, the patient will undergo a sleep laboratory evaluation where algorithm parameters, such as those programmable parameters described herein (onset and offset thresholds, refractory, dose times, etc.) are optimized to achieve proper stimulation for the individual patient. The stimulation parameters (amplitude, rate, and pulse width) are also adjusted to achieve the muscle stimulation necessary to overcome respiratory obstructions. After being programmed by the physician, the patient is provided with a hand-held patient programmer 70 which is primarily used to turn the IPG ON and OFF each evening and morning, respectively. The patient programmer 70 also may provide the patient with display indications regarding system information such as battery life warnings, failed stimulus components, etc., and further may be used to automatically initiate other diagnostic and stimulation testing as described further below. The implanted stimulation system 50, upon initialization of treatment, then utilizes the sensed respiration effort waveform to detect critical points in the waveform to provide inspiration synchronous stimulation for treating respiratory disorder in accordance with the algorithm as described above.

Figure 16A:
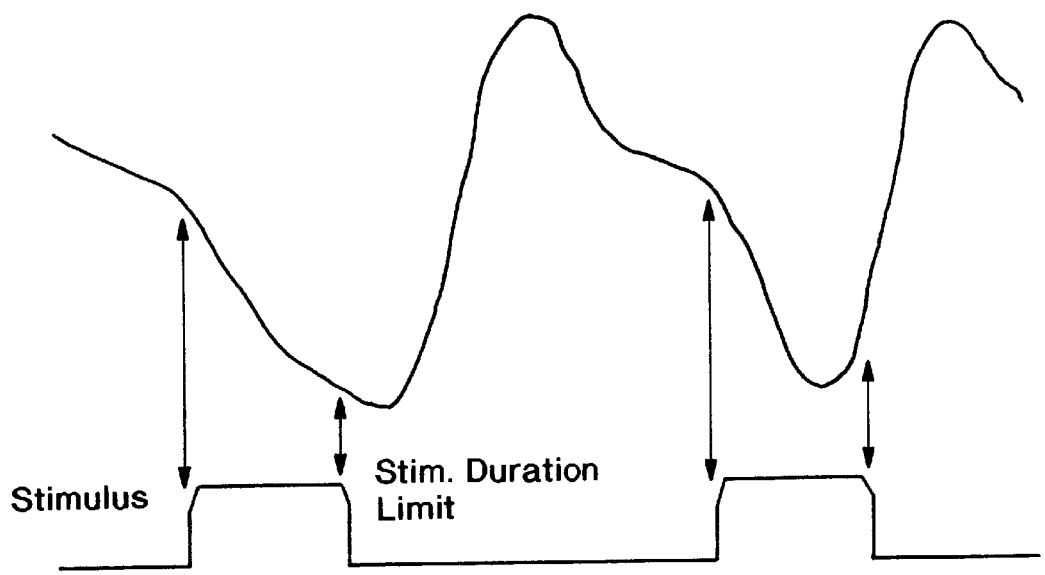
FIG. 16a shows a normal respiratory effort waveform and stimulus applied according to the present invention.
Figure 16B:
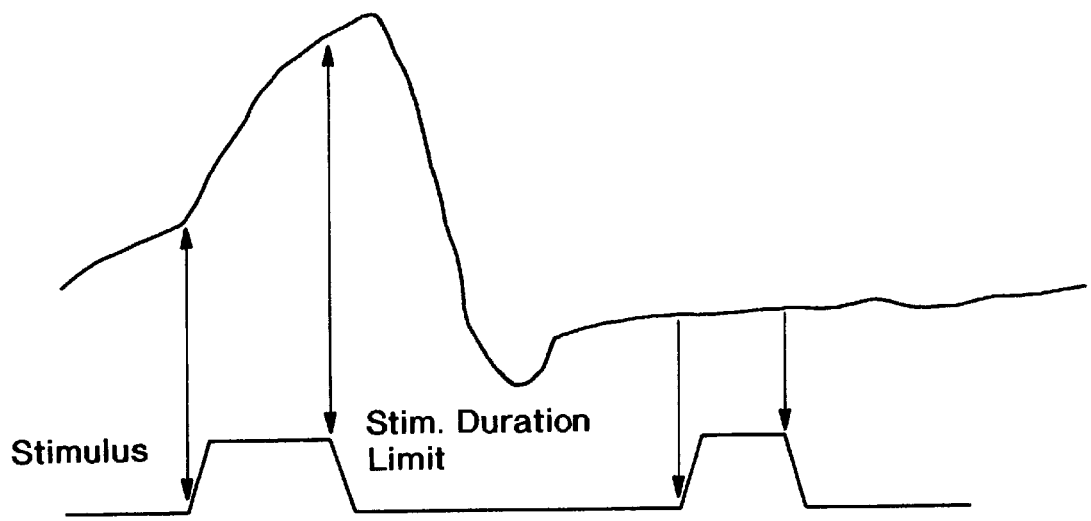
FIG. 16b shows a respiratory effort waveform of a patient with central sleep apnea and a stimulus applied according to the present invention utilizing a maximum stimulation time limit in accordance with the present invention.

The system 50 can also be used for patients with central apnea, or patients whose central nervous system provides no drive to breath. Central apneas often occur in obstructive sleep apnea patients in what are call mixed apneas. To ensure effective therapy, the patient must be stimulated over the first breaths following the central apnea, in order to prevent obstructive apneas. Patients with such conditions generate a respiratory effort waveform somewhat as shown in FIG. 16b or FIG. 16c as compared to a normal respiratory waveform (FIG. 16a). Because of the relative flatness of the waveform, offset and onset detection is difficult and almost unusable for providing stimulation to treat the upper airway condition. However, the detection algorithm can be adjusted to continue stimulation asynchronously when the signal amplitude becomes small. By making the ΔV and analog onset thresholds sensitive to flat sensor signals, stimulation can be maintained for such a patient. Although offsets are not detected, the maximum stimulation time can be used to terminate stimulation. Further, stimulation occurs, i.e., turns on, either at the end of hard refractory (HR) or refractory (R). The average respiratory period weighted sum (TWS) is approximately maintained by the repetitive stimulation occurring based on the maximum stimulation time and asynchronous stimulation will continue until the patient's periodic respiration returns. Further, the maximum stimulation time can be adjusted to forego overstimulation.

A central sleep apnea is shown in FIG. 16c. For example, the central sleep apnea 802 may occur over a time period of 5 seconds to 30 seconds. As shown in FIG. 16d, stimulation is synchronized to inspiration during the first and second cycles of respiration prior to central apnea occurring. Stimulation, in accordance with the present invention, then occurs for the maximum stimulation time 804 as offset is not detected during central apnea. The offset is then due to maximum stimulation time being reached. Refractory then occurs after the maximum stimulation time, during which time no stimulation is allowed. This particular refractory period 806 is shown by the time period between the two maximum stimulation times during the central sleep apnea. During this time, i.e. central sleep apnea, the AGC is operating by means of the watchdog timer and/or the maximum stimulation time offsets which update gain when no inspiration offsets are detected for a particular period of time. This operation of the AGC, increases the signal amplitude, and allows the algorithm to detect an onset with use of a smaller amplitude respiratory signal. Once a first onset is detected (or offset) then stimulation can be continued synchronous with inspiration as opposed to stimulating based on maximum period of stimulation and refractory. This ability to increase gain to detect offsets or onsets of a smaller respiratory signal is important because the first breaths 800, FIG. 16c after central apnea are typically shallow (low effort) and thus the algorithm compensates for the low effort by increasing the gain of the signal using the watchdog timer. The increase in gain 810 during the central apnea is shown in FIG. 16e.

Figure 17A:
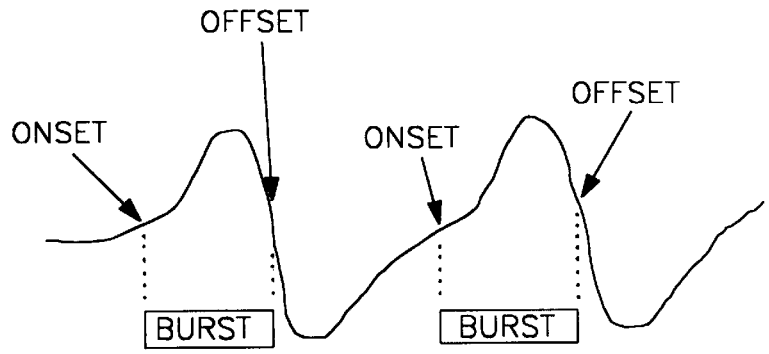
FIGS. 17a–c are graphs of one embodiment of a stimulation burst used for stimulating the patient according to the present invention.

The stimulation control using the detection algorithm described above and synchronized to the respiratory effort waveform allows for the provision of a preprogrammed train of pulses, i.e., voltage, current, power, to the electrode 65 (FIG. 5) as shown in FIG. 17a. This train of pulses, also referred to as a burst, stimulate the nerve/muscle, such as a muscle in the upper airway, the diaphragm, or any other muscles which are suitable for use in treatment.

Figure 17B:
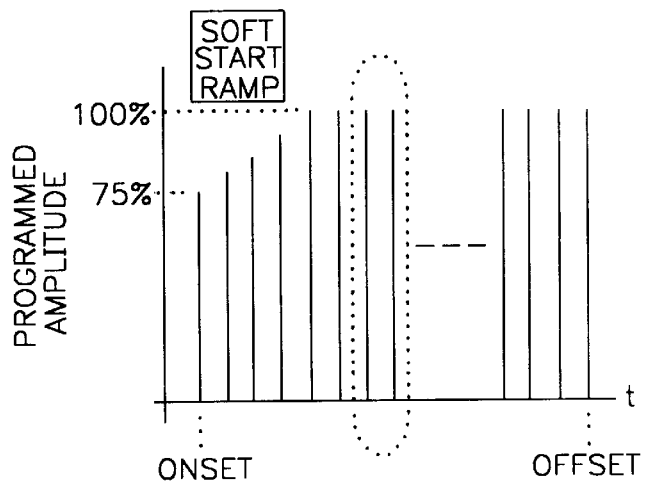

FIG. 17b shows characteristics of a typical train of pulses that is initiated upon onset detection as previously described. The train of pulses is shown to begin upon onset at an amplitude of about 75% of the programmed value. The amplitude is then ramped to 100% of the programmed value. This ramped function provides added comfort during the nerve stimulation. However, alternatively, the train of pulses may be started at any percentage of the programmed value or any percentage of the programmed value, i.e. 100%, 110%, 150%. The train of pulses ends upon the declaration of an offset, when maximum stimulation time is reached or the IPG off command is entered as described previously.

Figure 17C:
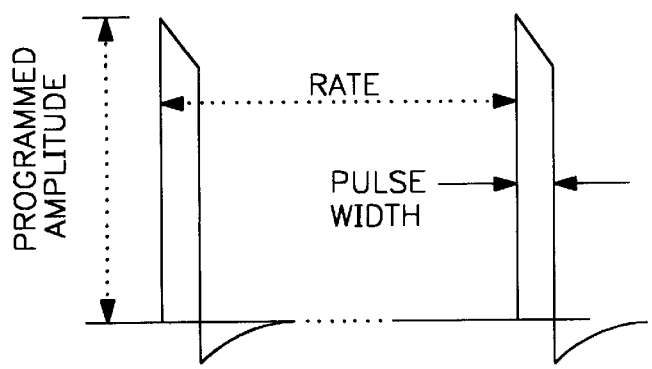

FIG. 17c shows the characteristics of the individual pulses within the train of pulses. Amplitude, the rate at which the pulses are delivered and the width of the individual pulses all impact the stimulation of the muscle. Minimizing the programmable amplitude, pulse width and rate of stimulation increases the longevity of the system. As one of ordinary skill in the art will recognize there are various manners of providing the train of pulses or a single pulse, and the present invention is not limited to any particular manner of generating such pulses. Any suitable circuit configuration for providing such pulses may be utilized, such as those available with the ITREL platforms.

Figure 18:
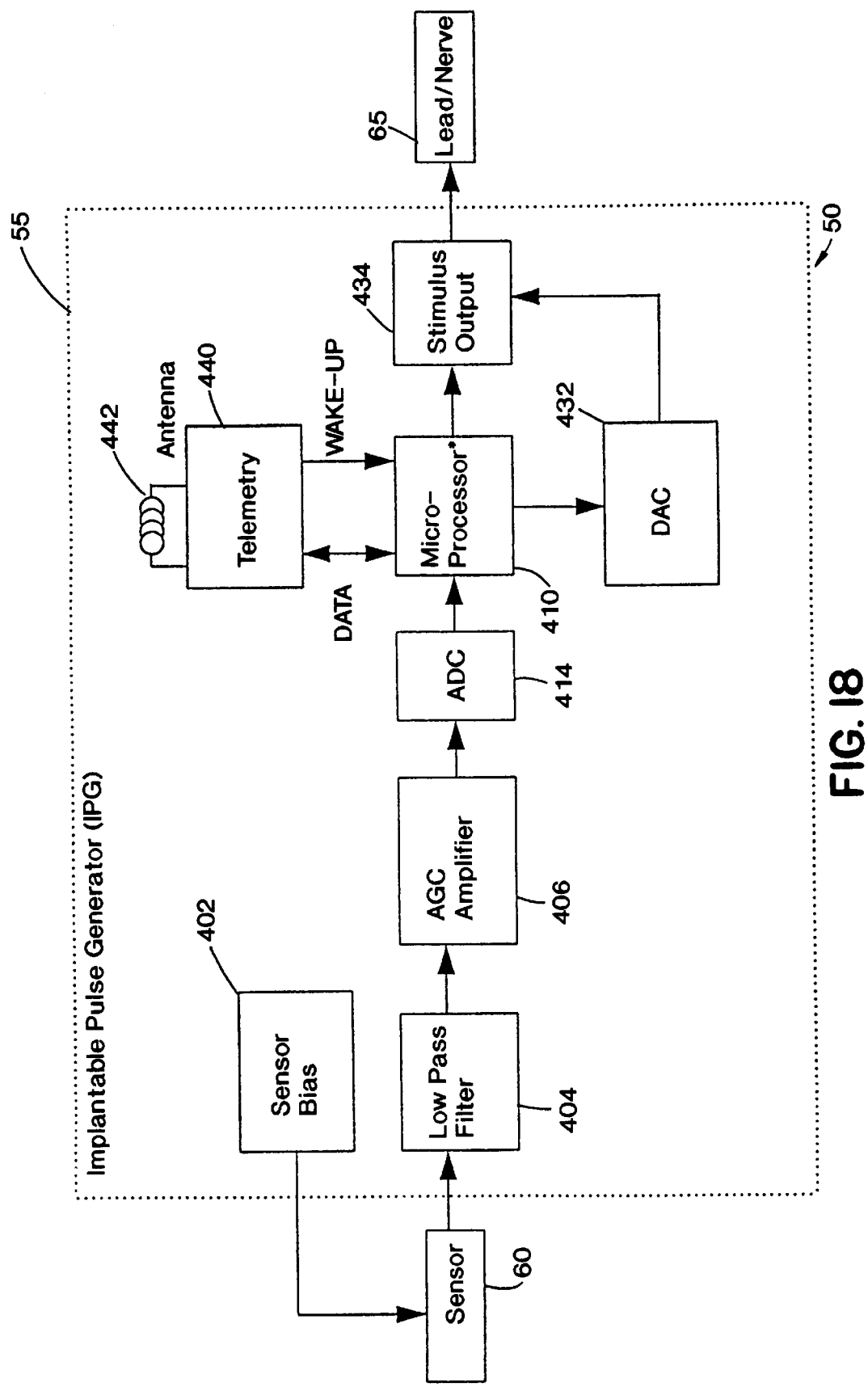
FIG. 18 is a block diagram of one embodiment of a microprocessor based stimulation system.

FIG. 18 shows the system 50, as shown in FIG. 5, including the IPG 55 which is a processor based IPG such as shown in FIG. 12b, sensor 60, and lead/electrode 65. The microprocessor 410 as previously described internally includes ADC 414. The IPG also includes the other components previously discussed including sensor bias 402, low pass filter 404, and AGC amplifier 406. Further included in the IPG 55 are telemetry components 440 coupled to antenna 442, stimulus output circuit 434 and digital to analog convertor (DAC) 432 which is used to produce the correct stimulus output amplitude for the system. The microprocessor 410, in addition to controlling stimulation, also controls the sensor bias 402, AGC amplifier 406 and diagnostic self test functions as described further below.

With reference to the system of FIG. 18, an energy conserving technique shall be described which is not only applicable to this particular system, but also to other implantable therapy systems, such as, for example, drug delivery systems, other stimulation systems, and any other systems which could benefit from such an energy conservation technique. The processor based IPG 55 enters an off state, i.e. a treatment period is not occurring, as a result of various events. For example, the off state in the system 50 is entered when the patient programmer 70 is used to send an IPG off command via telemetry using the telemetry circuitry and antenna 442. Further, the treatment period may end as a result of a dose timer timing out at the end of a dose period, such as in the morning after a nighttime treatment period, or the treatment period may end as a result of some other event. In such cases, the microprocessor 410 goes through a shut-down sequence and enters an off or 'sleep' mode during which it is not required to function.

The shut down sequence includes turning off power to all non-essential circuits of the system 50. Such non-essential circuits during the sleep mode include the amplifier 406, sensor bias 402, ADC 414, DAC 432, and stimulus output circuits 434. In the microprocessor based system, the microprocessor can also enter the sleep mode or stop mode where very little current is consumed, but the microprocessor will awake when an interrupt line is toggled. The telemetry block 440 remains on to listen for telemetry communication, such as from the patient programmer 70, and then wakes the microprocessor 410 when the external communication, i.e. telemetry command, is received. During operation of the sleep mode, energy is conserved.

This sleep mode can also be used with the IPG having processing circuitry that is not microprocessor based. For example, the logic circuits could be shut down or powered down. Further, methods other than telemetry could be used to wake up the processor. For example, a patient held magnet and a reedswitch trigger located in the IPG could be used, or a background timer in the IPG could be used to automatically turn the IPG on at a certain time. Further, as previously indicated above, this sleep mode could be used with other implantable therapy systems. For example, a blink stimulation system could enter sleep mode at night when essential circuits are not used or a drug delivery system could use sleep mode when there is a period of time that the essential components are not needed.

The patient programmer 70, FIG. 8, and the physician programmer 80, FIG. 7, communicate with the IPG 55 via telemetry. The physician programmer 80 allows the programmable parameters of the system to be adjusted by the physician to conform to the needs of the patient. Such programming devices are readily known to those skilled in the art. Examples of such devices are described in U.S. Pat. No. 4,236,524 to Powell et al., U.S. Pat. No. 4,250,884 to Hartlaub et al., U.S. Pat. No. 4,305,397 to Weisbrod et al., U.S. Pat. No. 4,323,074 to Nelms, U.S. Pat. No. 4,432,360 to Mumford et al., and U.S. Statutory Invention Registration No. H1347 to Greeninger et al., all incorporated herein by reference in their entirety. For example, all the programmable parameters mentioned with respect to the detection algorithm and also the stimulus pulse amplitude, stimulus pulse duration, stimulus pulse frequency, and stimulus ramp on/off times can be adjusted through the physician programmer 80. In addition, the physician programmer 80 can be used to access any stored data and retrieve such data stored in the implanted system. For example, the patient's name, the code number of the hospital or clinic, the prescription date, and the last follow-up date could be stored in hardware of the system. Further, patient compliance data, system performance data, diagnostic testing data could be accumulated by the system and read out through use of the programmer 80. For example, the total time the power is on, total stimulation time for the patient, the number of power cycles or reset cycles, the average battery voltage and fault detection could be stored and retrieved through the physician programmer 80.

FIG. 8 shows the patient programmer 70 for patient control of the system 50. The control panel of programmer 70 includes on and off switches 71, 75 which allow the patient to turn the system on or off. Turning switch 71 on initializes the treatment period using the above described control logic. The buttons 73 allow the patient to adjust the amplitude of stimulation for comfort level and other controls could be added to allow the patient to control other parameters such as, for example, pulse rate, pulse width, delay times.

The power on switch 71 also may be utilized to initiate various self test functions as well as initiating a dose delay (block 604) if the device is already operating. One self test function initiated by the power on switch is a patient stimulation self test function, wherein when the patient turns the stimulation system on with the patient programmer 70 for a treatment period, i.e. before going to bed, the stimulator immediately thereafter automatically provides stimulation to the patient, such as to the hypoglossal nerve. This stimulation may be based on the maximum stimulation time or any other predetermined time period. Such power on stimulation, gives the patient the ability to verify that the system is capable of stimulating properly. For example, the stimulation verifies that the nerve/muscle was captured, that the lead placement is correct, that the lead from the IPG 55 to the electrode 65 is operative, and also that the IPG stimulator output circuits for providing the pulse are functioning properly. At any time during the treatment, if the patient did not think that the system 50 was functioning properly, the patient could, by pushing the power on switch, provide a stimulus to check the device. Further, the stimulation self test could be performed at IPG-OFF.

The patient stimulation self test is not only applicable to respiratory treatment systems as described herein, but is equally applicable to any stimulation systems that provide patient treatment. For example, such a self test could be used with a muscle therapy or conditioning system, a blink electrode stimulation system, or any other neuromuscular stimulation system. With respect to the respiratory disorder treatment system described herein which, for example, stimulates the hypoglossal nerve, the stimulation automatically provided provides stimulation sufficient to evoke tongue protrusion, which the patient senses and thus can verify that the stimulator is on and stimulation is functional.

Any faults detected by the stimulator using the stimulation self test or by any of the other tests described herein, such as the diagnostic self tests, can be reported to the patient via the patient programmer 70. Further, since the patient by the power on stimulus has tested the adequacy of the stimulation, the patient can adjust the amplitude of stimulation by buttons 73, for example, within certain bounds set by the physician. This adjustment would allow the patient to increase stimulation amplitude if capture of the nerve was not occurring or decrease amplitude of stimulation if adequate capture was occurring, in order to increase battery longevity. Such patient adjustment may be used for any other physician programmable parameters that the physician would want the patient to be able to control. For example, stimulus rate, pulse width, therapy delay periods, etc. Moreover, if the system is not functioning properly, a visit to the physician can be made for evaluation of the system, i.e. such as by accessing test data or fault data stored in the system.

The power on switch 71 may also be utilized to initiate an internal diagnostic self test for testing the system to determine whether the components and circuit functions, along with the detection algorithm are operating properly. However such diagnostic self test can also be run whenever the system is not interactive with the patient. For example, a diagnostic self test of the system described with reference to FIG. 18 could be run during a dose delay, a sleep mode, a therapy delay, at IPG-OFF or anytime during the day when the patient is awake. During the diagnostic self test, components and functions of the system can be tested, for example, with reference to the system of FIG. 18, the amplifier 406, the filter 404, and all the rest of the components can be tested as described further below. Typically, such testing is performed at the physicians office using the physician programmer 80. However, since this treatment is performed during the sleep period of a patient's day, it may not be known whether the system is functioning properly or not as the patient is asleep when it is operating. Therefore, a diagnostic self test during a period of time when the system is not interacting with the patient, i.e. stimulation or sensing, or in other words when the patient is not dependent on the treatment, is beneficial. With, for example, a fault indication sent to the patient programmer 70 when faults are detected, the patient has some assurance that the system is functioning properly.

Figure 19:
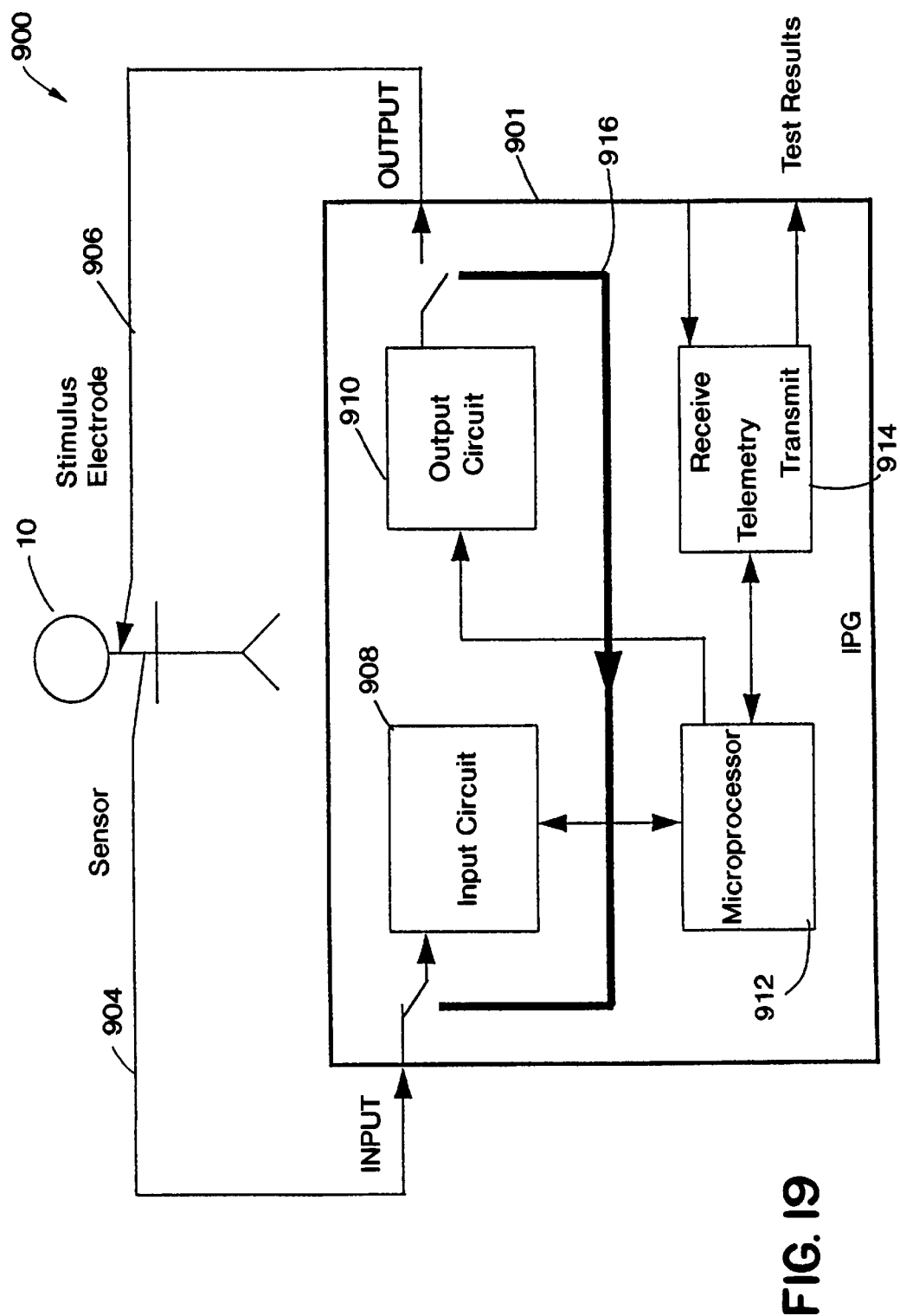
FIG. 19 is a block diagram illustration of one diagnostic self test strategy for a therapy system.

The diagnostic self test strategy as shown in FIG. 19, is applicable to many different therapy systems. For example, as shown therein, a typical therapy system 900 includes a therapy device 901, i.e. IPG 55, having an input circuit 908 for receiving an input such as a sensed signal 904 of a patient 10. The device 901 further includes a microprocessor or some other logic circuitry 912 for processing the sensed signal and generating an output 906 via output circuit 910. Further, the device may include telemetry circuitry 914 for receiving and transmitting information from and to an external source.

The general diagnostic test strategy for such a generally described therapy system, includes applying the generated output 906 from the output circuit 910 to the patient 10. The result of the therapy due to the generated output 906 is sensed via the input circuit 908 to verify operation of the system. For example, a stimulus output, i.e. a cardiac pace, could be applied to the patient and the input circuit could sense whether the cardiac pace resulted in a physiological response in the patient. Further, for example, the stimulus output could be a train of pulses to the genioglossus muscle to treat sleep apnea. The input circuit would then provide the sensed signal characteristic of respiratory effort to the microprocessor to verify that a correct respiratory response was achieved with the stimulus of the genioglossus muscle, i.e. open airway and proper respiratory action. If a correct response is not indicated, the system could be further tested. An internal attenuated feedback output 916 (shown as a thicker line than the lines of system normal configuration) from the output to the input can be used to determine if the input or output circuits are operating properly. This general test strategy will detect faults internal and external to the device 601. For example, a broken stimulus or sense lead could be detected or a faulty output circuit could be detected.

Figure 20B:
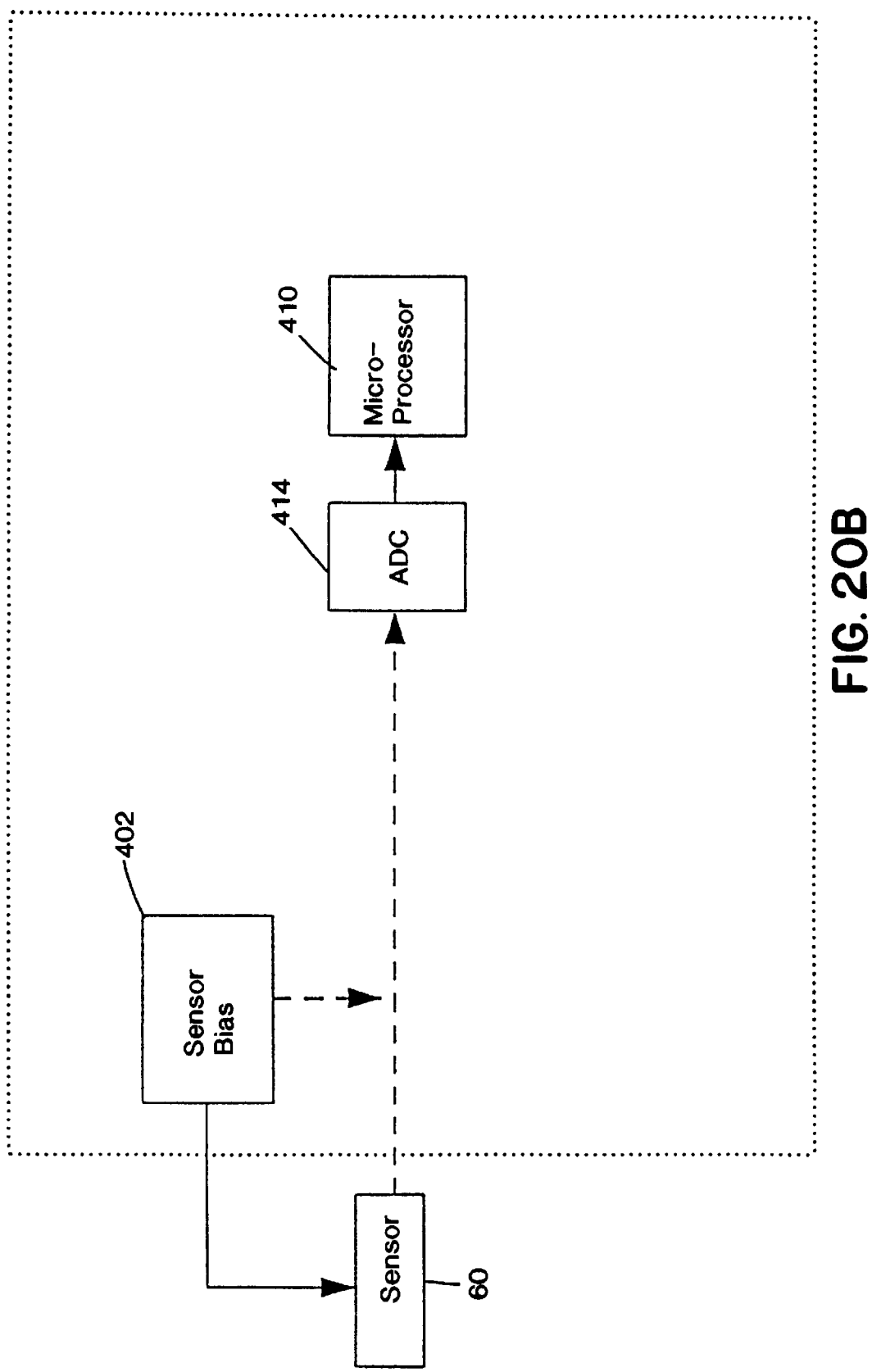

FIGS. 20a–d show various block diagrams of other more specific internal diagnostic self tests for testing various components of the system shown in FIG. 18. FIG. 20a shows the blocks of FIG. 18 involved in a front end amplifier self test. The DAC 432 sends a voltage or voltage pulse to the input of filter 404, amplifier 406, or ADC 414. The microprocessor 410 then verifies the correct response. The DAC 432 is also verified by its participation in these loops.

FIG. 20b shows the blocks involved in a sensor bias self test. A bias signal from sensor bias 402 is directed to the ADC 414 and measured and compared to set references by the microprocessor 410. A sensor signal from sensor 60, for example, a DC static voltage resulting from sensor bias, can also be directed to the ADC 414, measured and compared to set references by the microprocessor 410 for verification.

Figure 20C:
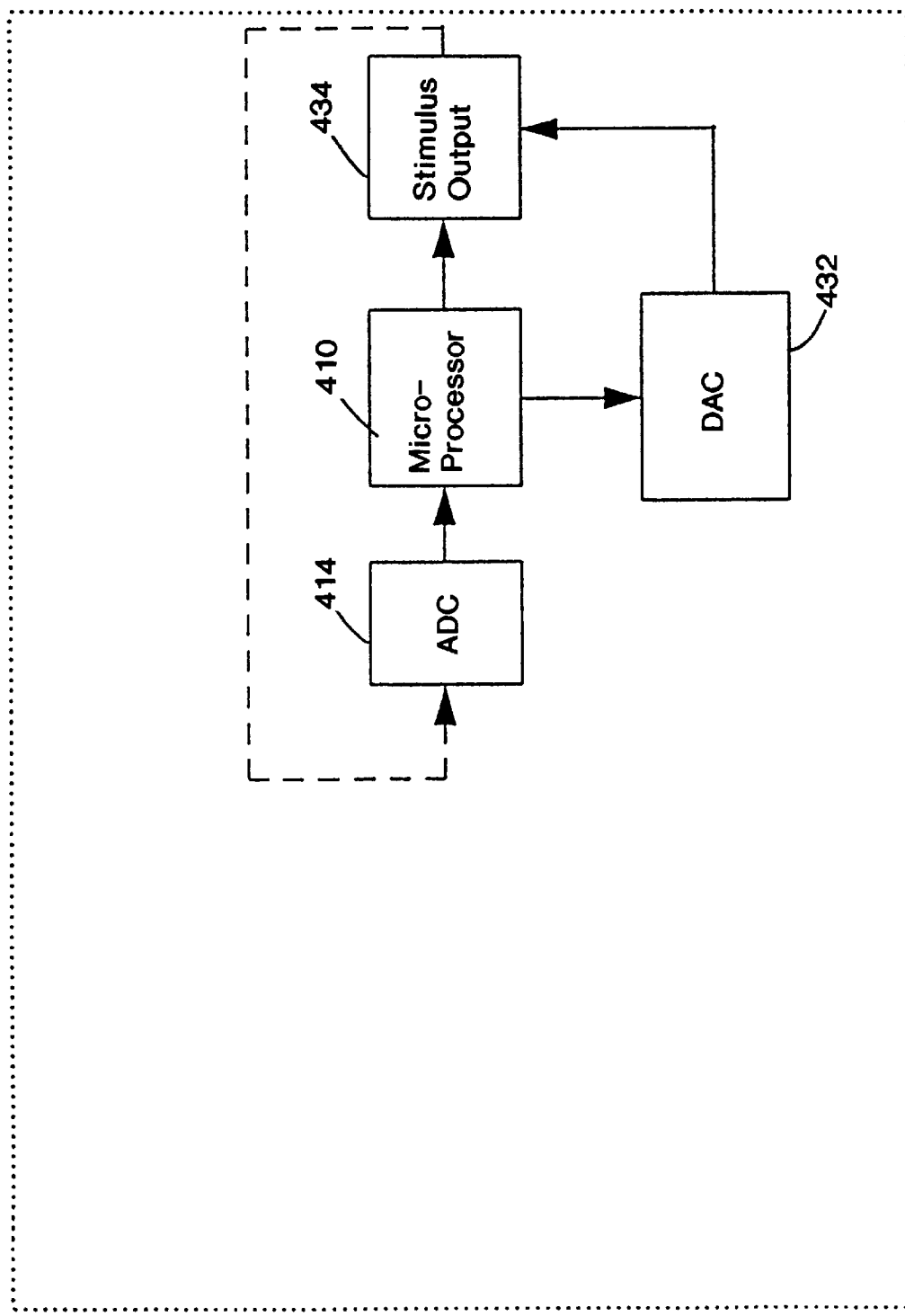

FIG. 20c shows the blocks involved in a stimulus output self test. The output from the stimulus output 434 with its amplitude under control of DAC 432 is directed to the ADC 414 and verified by the microprocessor 410. The output can be ramped to its maximum stimulus and then attenuated for input to ADC 414 for measurement.

Figure 20D:
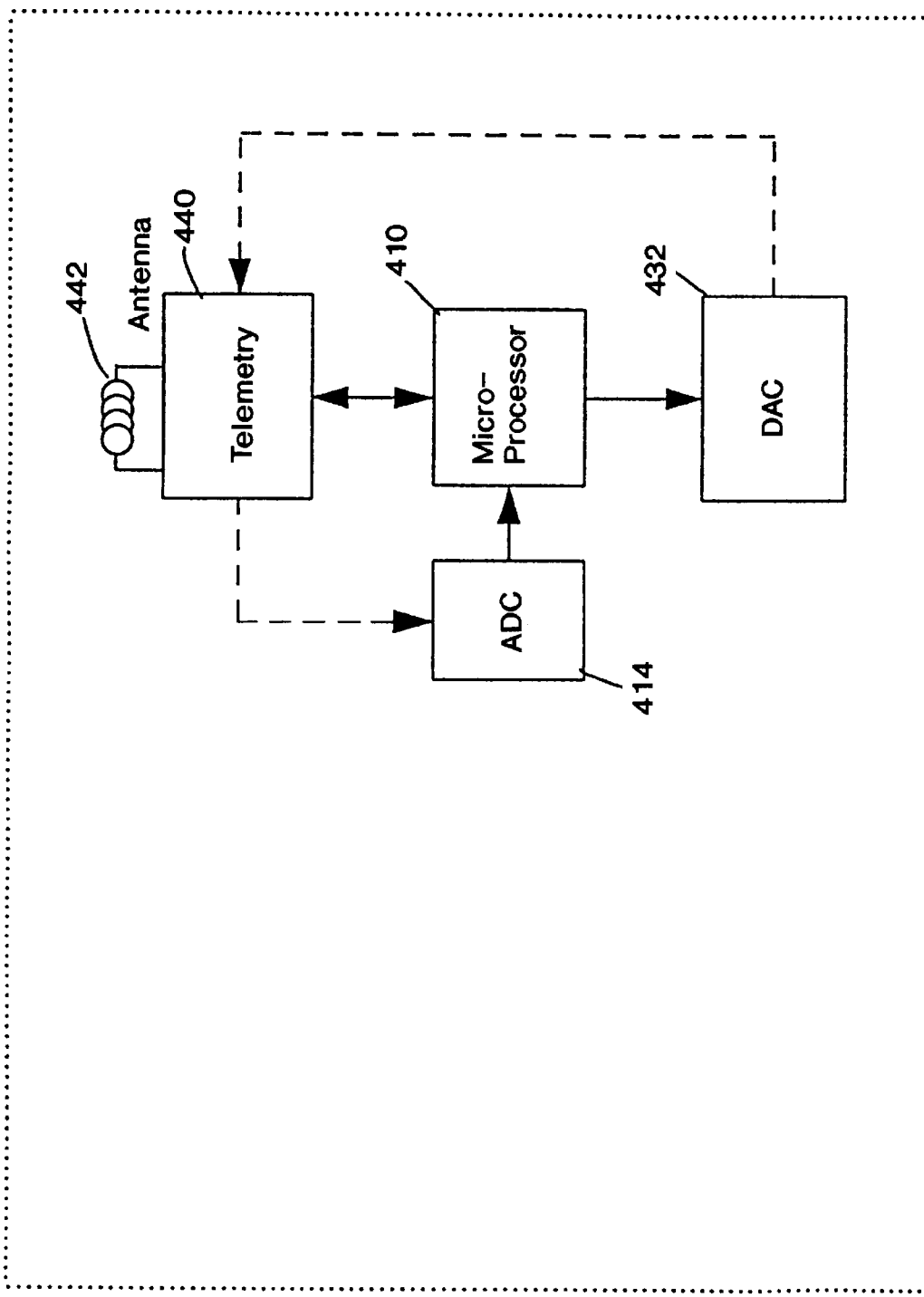

FIG. 20d shows the blocks involved in a telemetry self test. The telemetry circuitry 440 can be tested in a couple of ways. First, known voltage pulses are applied to the telemetry circuit 440 via the DAC 432 to drive the circuit, i.e. simulate a received ping, and telemetry reception is verified via the microprocessor 410 and a demodulated voltage measured on the ADC 414. Likewise, the microprocessor 410 could initiate a telemetry uplink, i.e. ping on antenna, and the ADC 414 will verify the signal on the antenna 442. Second, a telemetry uplink can be initiated with the microprocessor 410, i.e. ping the antenna, and then immediately enable the telemetry demodulator of circuitry 440 to detect the ringing of the antenna 442 with verification of the detection performed by the microprocessor 410. This second test would not use the ADC 414 or the DAC 432.

Further tests could be performed to verify other components and functions. For example, the AGC could be calibrated by switching in a known signal, analog offset and onset detection could be verified by a DAC generated signal, and lead and battery measurements could be made. Further, diagnostic self test results can be stored and uplinked to allow quick fault identification at either a patient or a physician programmer.

It will be appreciated by those skilled in the art that while the invention has been described above in connection with particular embodiments and examples, the invention is not necessarily so limited and that numerous other embodiments, examples, uses, modifications and departures from the embodiments, examples and uses may be made without departing from the inventive concepts.

We claim:

1. A testing method for use with an implantable patient stimulation system, comprising the steps of:
   providing a stimulation system including an implantable stimulator and a patient control unit which uses telemetry for initiating and terminating treatment periods; and
   testing the stimulation system by automatically providing at least one period of stimulation to stimulate the patient upon initiating a treatment period;
   in which a length of any period of stimulation is based upon a maximum stimulation time defined for the system.

2. The method according to claim 1, in which the patient control unit further allows the patient to adjust at least one characteristic of stimulation.

3. The method according to claim 2, in which the system allows the patient to adjust at least one characteristic chosen from the group consisting essentially of amplitude, rate, and pulse width.

4. The method according to claim 1, in which the stimulation system treats respiratory disorders, and does not permit patient stimulation for a predetermined period of time after the automatic provision of stimulation.

5. A stimulation system, comprising:
   an implantable stimulator to stimulate a patient during a treatment period; and
   a patient control unit, which comprises a transmitter/receiver element for communication with the implantable stimulator, for initiating and terminating treatment periods, the stimulator automatically providing at least one period of stimulation upon initiation of a treatment period;
   in which a length of any period of stimulation is based upon a maximum stimulation time defined for the system.

6. The system according to claim 5, in which the control unit further allows the patient to adjust at least one characteristic of stimulation.

7. The system according to claim 6, in which the system allows the patient to adjust at least one characteristic chosen from the group consisting essentially of amplitude, rate, and pulse width.

8. The system according to claim 5, in which the stimulator comprises a stimulation control device for generating the stimulation and at least one electrode connected between the stimulator and the patient, in which the stimulation indicates that at least the placement of the electrode is adequate and functional.

9. The system according to claim 5, in which the system treats respiratory disorders by prohibiting stimulation after the automatic provision of the period of stimulation for a predetermined period of time.

10. A system test method for use with a therapy system, the method comprising the steps of:
    providing a therapy system, comprising an implantable stimulation system to treat respiratory disorders of a patient substantially only during periods when the patient is asleep, having a plurality of components including a patient control unit for at least initiating therapy to the patient during a treatment period; and
    performing, internally to the system, a diagnostic self test of a component of the therapy system to determine if the component is functioning properly at a time when the therapy system is not interacting physiologically with the patient, in which the diagnostic self test of the component is automatically performed upon initiation of the treatment period by the patient.

11. The method according to claim 10, further including the step of communicating a fault to the patient if a failure of the component is determined.

12. The method according to claim 10, in which the therapy system includes an input circuit for receiving a sensed signal characteristic of a physiological parameter of the patient and an output circuit for generating a therapy output for physiological treatment of the patient, and further in which the performing step includes the step of using a feedback signal from the output to the input to perform the self test of the component.

13. The method according to claim 10, in which the therapy system includes an input circuit for receiving a sensed signal characteristic of a physiological parameter of the patient and an output circuit for generating a therapy output for providing therapy to the patient, and further in which the performing step includes the steps of:
    generating a therapy output for providing therapy to the patient;
    measuring an effect of the therapy on the patient due to the therapy output using the sensed signal; and
    verifying that the effect resulting from the therapy output was correct.

14. The method according to claim 10, in which the performing step includes the steps of:
    applying a known signal to an input of the component and measuring an output generated as a function of the component; and
    verifying the accuracy of the output.

15. A system for use in testing a therapy system, comprising:
    a therapy system, comprising an implantable stimulation system to treat respiratory disorders of a patient substantially only during periods when the patient is asleep, having a plurality of components including a patient control unit for at least initiating therapy to the patient during a treatment period; and
    a diagnostic circuit internal to the system for automatically performing, upon initiation of the treatment period by the patient, a self test of a component of the therapy system to determine if the component is functioning properly at a time when the therapy system is not interacting physiologically with the patient.

16. The system according to claim 15, in which the diagnostic circuit communicates a fault to the patient if a failure of the component is determined.

17. The system according to claim 15, in which the therapy system includes an input circuit for receiving a sensed signal characteristic of a physiological parameter of the patient and an output circuit for generating a therapy output for physiological treatment of the patient, and further in which the diagnostic circuit generates a feedback signal from the output circuit to an input of the input circuit for use in performing the self test of the component.

18. The method according to claim 17, in which the output circuit generates a therapy output resulting in a physiological effect on the patient, the input circuit receives a sensed signal characteristic of the physiological effect, and the diagnostic circuit verifies that the physiological effect resulting from a particular therapy output is a correct physiological effect.

19. The system according to claim 15, in which the diagnostic circuit:

applies a known signal to an input of the component;

measures an output generated as a function of the component acting on the known signal; and verifies the measured output to determine correct performance of the component.

* * * * *